US005576480A

United States Patent [19]
Hopkins et al.

[11] Patent Number: 5,576,480
[45] Date of Patent: Nov. 19, 1996

[54] SYSTEM AND METHOD FOR TESTING THE INTEGRITY OF POROUS ELEMENTS

[75] Inventors: Scott D. Hopkins, Dryden; Daniel W. Spencer, Cortland; Charles P. Lipari, Port Jefferson; George A. Altemose, Stony Brook, all of N.Y.

[73] Assignee: Pall Corporation, East Hills, N.Y.

[21] Appl. No.: 249,373

[22] Filed: May 25, 1994

Related U.S. Application Data

[63] Continuation-in-part of PCT/US93/10691, Nov. 8, 1993, and Ser. No. 971,605, Nov. 6, 1992, abandoned.

[51] Int. Cl.$^6$ .............. G01N 15/08; G01N 29/14
[52] U.S. Cl. ............................... 73/38; 73/587
[58] Field of Search .................. 73/38, 40, 597, 73/579, 587, 592

[56] References Cited

U.S. PATENT DOCUMENTS

| | | | |
|---|---|---|---|
| 4,059,008 | 11/1977 | Torstensson | 73/38 |
| 4,327,576 | 5/1982 | Dickey et al. | 73/40.5 A |
| 4,384,474 | 5/1983 | Kowalski | 73/38 |
| 4,449,392 | 5/1984 | Huschke | 73/38 |
| 4,492,392 | 1/1985 | Woods | 285/119 |
| 4,511,471 | 6/1985 | Müller | 210/323.2 |
| 4,557,603 | 12/1985 | Oehler et al. | 356/418 |
| 4,571,994 | 2/1986 | Dickey et al. | 73/40.5 A |
| 4,583,406 | 4/1986 | Dimeff | 73/592 |
| 4,614,109 | 9/1986 | Hofmann | 73/38 |
| 4,622,845 | 11/1986 | Ryan et al. | 73/24 |
| 4,676,092 | 6/1987 | Tuttle | 73/38 |
| 4,701,861 | 10/1987 | Kauke | 364/502 |
| 4,718,270 | 1/1988 | Storr | 73/38 |
| 4,744,240 | 5/1988 | Reichelt | 73/38 |
| 4,779,448 | 10/1988 | Gogins | 73/38 |
| 4,872,974 | 10/1989 | Hirayama et al. | 210/90 |
| 4,881,176 | 11/1989 | Kononov | 364/500 |
| 4,909,937 | 3/1990 | Hoffmann et al. | 210/315 |

(List continued on next page.)

FOREIGN PATENT DOCUMENTS

| | | | |
|---|---|---|---|
| 392158 | 7/1990 | Austria . | |
| 0139202 | 9/1984 | European Pat. Off. | 15/8 |
| 0314822 | 11/1987 | European Pat. Off. | 11/28 |
| 0248218 | 12/1987 | European Pat. Off. | 87/50 |
| 0640822 | 8/1994 | European Pat. Off. | 3/24 |
| 2582809 | 12/1986 | France | 19/00 |
| 8212094 | 8/1982 | Germany . | |
| 3147421 | 6/1983 | Germany | 29/02 |
| 224936 | 6/1984 | Germany . | |
| 3306647 | 8/1984 | Germany . | |
| 3312729 | 10/1984 | Germany . | |
| 3726585 | 2/1989 | Germany | 3/24 |
| 3917856 | 12/1989 | Germany | 15/8 |
| 3911648 | 10/1990 | Germany | 3/18 |
| 57-102212 | 6/1982 | Japan | 35/14 |

(List continued on next page.)

OTHER PUBLICATIONS

Reichelt, G. "Bubble point measurements on large areas of microporous membranes," Journal of Membrane Science 60 (1991) 253–259.

"LabView Analysis VI Reference Manual"; Nov. 1992 Edition Part No. 320538-01; pp. National Instruments Corp.; pp. 3–36 to 10–37; 1992.

"Particulate Retention by Bacteria Retentive Membrane Filters"; David B. Pall et al.; Colloids and Surfaces 1(1980) 235–256; Elsevier Scientific Publishing Company, Amsterdam.

Primary Examiner—Hezron E. Williams
Assistant Examiner—Rose M. Finley
Attorney, Agent, or Firm—Leydig, Voit & Mayer

[57] ABSTRACT

An apparatus for detecting defects in porous elements including systems and methods for quantifying acoustic signal data. A transducer receives acoustic signals generated within a test chamber by a porous element. A signal processing device may be included for analyzing the acoustic signals received, for quantifying the acoustic signals, and for correlating the acoustic signals with physical attributes of the porous element.

200 Claims, 32 Drawing Sheets

U.S. PATENT DOCUMENTS

| | | | |
|---|---|---|---|
| 4,958,296 | 9/1990 | Saitoh et al. | 73/40.5 A |
| 4,972,730 | 11/1990 | Camp et al. | 73/865.5 |
| 5,005,430 | 4/1991 | Kibler et al. | 73/863.01 |
| 5,052,215 | 10/1991 | Lewis | 73/40.5 A |
| 5,064,529 | 11/1991 | Hirayama et al. | 210/90 |
| 5,161,408 | 11/1992 | McRae et al. | 73/40.7 |
| 5,353,630 | 10/1994 | Soda et al. | 73/38 |
| 5,417,101 | 5/1995 | Weich | 73/38 |
| 5,477,155 | 12/1995 | Proulx et al. | 324/71.1 |

FOREIGN PATENT DOCUMENTS

| | | | |
|---|---|---|---|
| 0109074 | 8/1917 | United Kingdom. | |
| 1568968 | 6/1980 | United Kingdom | 3/249004445 |
| 2127559 | 4/1984 | United Kingdom | 15/8 |
| 2140163 | 5/1984 | United Kingdom. | |
| 2132366 | 7/1984 | United Kingdom. | |
| 8404593 | 11/1984 | WIPO | 15/8 |
| 9004445 | 5/1990 | WIPO | 29/24 |
| 9411721 | 5/1994 | WIPO | 15/8 |

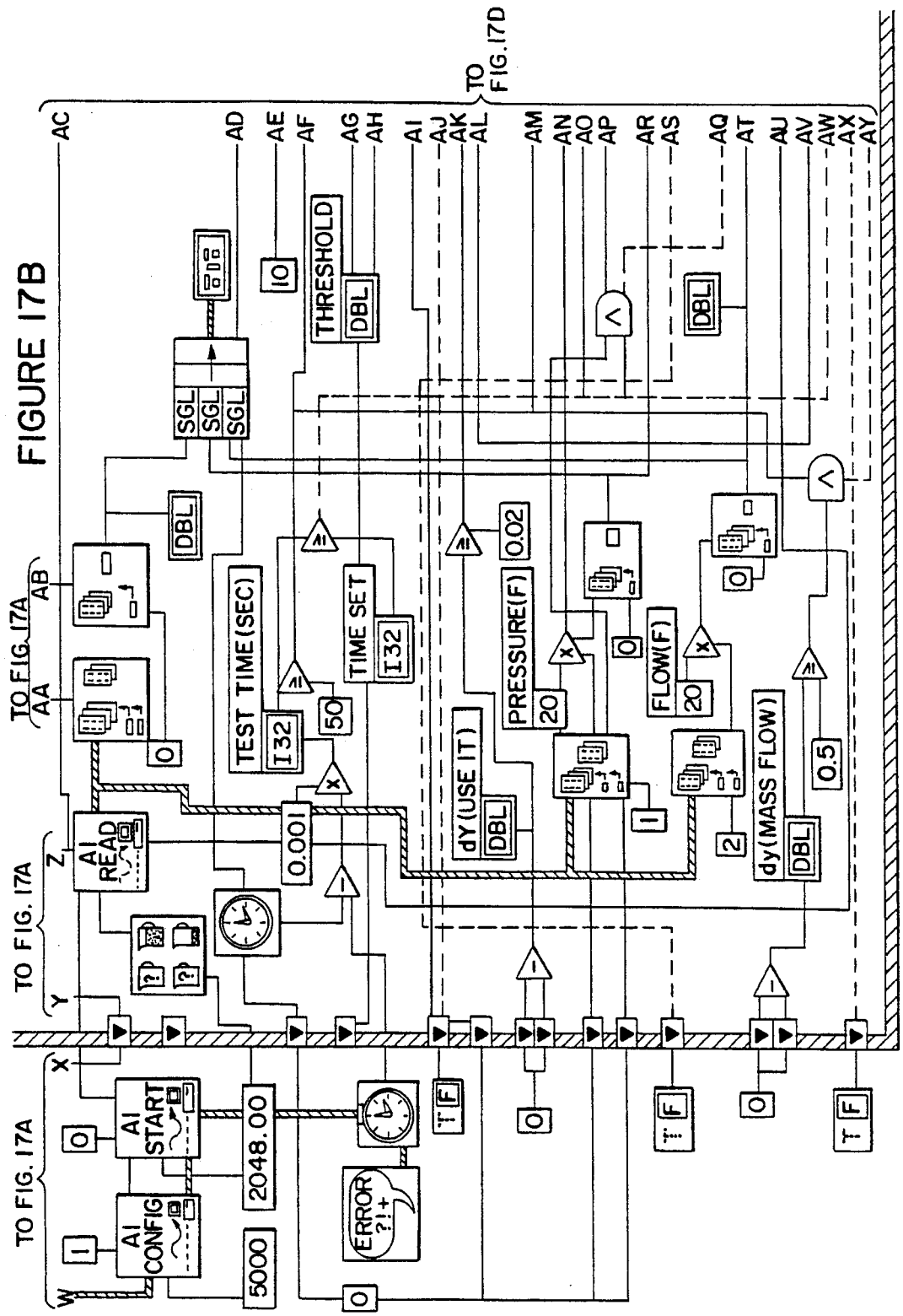

FIGURE 19

STEP IIa
```
COLLECTING ULTRASONIC POROUS ELEMENT
RESPONSE DATA FOR A SINGLE POROUS
         ELEMENT
-e.g., COLLECTING A/D SAMPLES FOR
      FOR A GIVEN INTERVAL
```

STEP IVa
```
ANALYZING THE RESPONSE DATA
-e.g., CALCULATING A STANDARD
DEVIATION FOR THE A/D SAMPLES
         COLLECTED
```

STEP VIa
```
INTERPETING THE DATA:
-e.g., COMPARING THE STANDARD
DEVIATION TO A KNOW INDEX
```

STEP VIIa
```
INDICATING PASS/FAIL
```

FIGURE 24

STEP IIb
```
COLLECTING ULTRASONIC POROUS ELEMENT
RESPONSE DATA FOR A SINGLE POROUS
         ELEMENT
```

STEP IIIb
```
QUATIFYING PULSES
-e.g., DETERMINING THE NUMBER OF
PULSES FOR A GIVEN INTERVAL
```

STEP VIb
```
INTERPRETING THE DATA:
-e.g., COMPARING THE PULSE
COUNT TO A KNOWN INDEX
```

STEP VIIb
```
INDICATING PASS/FAIL
```

FIGURE 25

QUANTITATIVE CHARACTERISTICS OF ACOUSTIC PULSES

* EACH A/D OUTPUT VALUE FOR THE ENTIRE PULSE
* INITIAL/FINAL MINIMUM VOLTAGE VALUE FOR EACH PULSE
* PEAK VOLTAGE VALUE FOR EACH PULSE
* AMOUNT THE PEAK VOLTAGE OF EACH PULSE EXCEEDS A MINIMUM VOLTAGE VALUE
* DIFFERENTIAL VOLTAGE OF EACH PULSE ABOVE A BASELINE VOLTAGE
* AVERAGE VOLTAGE (USING ANY SUITABLE AVERAGING TECHNIQUE)
* FREQUENCY SPECTRUM OF EACH PULSE
* WIDTH BETWEEN PEAKS OF SUCCESSIVE PULSES
* WIDTH BETWEEN INITIAL/FINAL MINIMUM VALUES OF EACH PULSE
* WIDTH OF EACH PULSE AT ARBITRARY VALUES ALONG THE PULSE SUCH AS, FOR EXAMPLE, AT 80% OF THE PULSE PEAK.
* WIDTH OF EACH PULSE AT A PREDETERMINED THRESHOLD VOLTAGE VALUE
* RISE TIME OF EACH PULSE
* FALL TIME OF EACH PULSE
* INSTANTANEOUS OR AVERAGE SLOPE OF THE RISING EDGE OF EACH PULSE
* INSTANTANEOUS OR AVERAGE SLOPE OF THE FALLING EDGE OF EACH PULSE
* INTEGRAL OF EACH PULSE OR A PLURALITY OF SUCCESSIVE PULSES (AREA UNDER EACH PULSE)

FIGURE 28

SYSTEM AND METHOD FOR TESTING THE INTEGRITY OF POROUS ELEMENTS

This application is a continuation-in-part application of International Application Serial No. PCT/US93/10691, filed Nov. 8, 1993 and U.S. application Ser. No. 07/971,605, filed Nov. 6, 1992, now abandoned.

TECHNICAL FIELD OF THE INVENTION

The present invention relates to systems and methods which permit the integrity of a porous element, such as a filtration element, to be quickly and reliably tested. In particular, the present invention relates to testing porous elements by detecting sound, for example ultrasound, produced when a wetted porous element is exposed to a differential pressure.

BACKGROUND OF THE INVENTION

In many fluid processing systems involving filtration, there is a requirement to achieve the highest possible assurance of filter integrity and removal efficiency. Examples of such applications include sterilization of parenterals, biological liquids, and fluids used in fermentation processes. Conventional methods utilized to verify the integrity of porous filter media include: microbiological challenge tests, effluent cleanliness tests, particle challenge tests, forward flow tests (including pressure decay tests), and reverse bubble tests. The microbiological challenge, particle challenge and effluent cleanliness tests are destructive tests, and cannot be performed in a production environment. The industry-accepted non-destructive tests used to verify the integrity of porous elements are the forward flow test or the reverse bubble test. Both of these tests are performed by applying a predetermined gas pressure to a wetted filter.

Reverse bubble testing has been utilized since the 1950s to determine the size and location of the largest pore in a filter element. See, for example, D. B. Pall (U.S. Pat. No. 3,007,334, filed Nov. 30, 1956). A reverse bubble test (sometimes referred to as a first bubble test) detects defects by looking for bubbles while a wetted filter is submersed in a liquid. With the filter wetted and liquid covering one side of the filter, a gas at constant and/or variable pressure is directed against the other side of the filter.

At a certain pressure, the gas is just able to force the liquid from some of the largest pores in a filter having a homogenous pore structure, and the gas forms bubbles in the liquid covering the filter. This pressure is known as the bubble point of the filter. Of course, as the pressure increases above the bubble point, more and more of the liquid is forced from increasingly smaller pores of the filter and the flow of gas through the filter increases.

The bubble point of the filter depends on many factors, but pore size is a dominant factor. Filters having larger pores have a bubble point that occurs at lower pressures when using the same type of wetting solution. If the pressure of the gas is below the bubble point of the filter, very little gas passes through the filter. However, if there are defects in the filter, the gas will pass through the defects in the filter and bubbles will form in the liquid.

Bubbles rising in the liquid can be detected either visually or electronically using a passive sonar device which monitors a sudden increase in the sound intensity caused by bubbles rising and/or collapsing in the liquid. A device which ultrasonically detects a sudden increase in the sound intensity at the bubble point as bubbles rise/collapse in the liquid is, for example, shown by Reichelt, U.S. Pat. No. 4,744,240. Reichelt is utilized for determining the bubble point pressure of the largest pores in a homogeneous, non-defective filter. Reichelt is directed to determining the pressure at which a sudden increase in sound volume resulting from an applied pressure at a level in which gas is forced through a plurality of pores in a in-tact filter element having a relatively homogenous pore structure. The apparatus disclosed in Reichelt does not detect defective filters having pin-hole defects. Another problem with the apparatus disclosed in Reichelt is that the liquid media in which the ultrasonic transducer is disposed couples the microphone to sounds down stream of the filter element and throughout the fluid flow system. In this configuration, noise produced by bubbles from, for example, pin-holes becomes lost in the ambient noise of the system and sources of noise outside of the system. Additionally, the Reichelt device only detects a sudden rise in the noise level produced at the bubble point. It was found that many defective filters cannot be detected simply by measuring the sudden rise in the noise level.

Reverse bubble testing has a number of limitations. For filters having a cylindrical configuration, the filter must be rotated as it is observed for the formations of bubbles. The observation of bubbles is hindered by the fact that bubbles may be trapped by the filter as it is placed in the liquid, particularly where the filter has closely spaced pleats. Additionally, depending on the geometry of the filter, type of wetting solution, and the applied pressure, diffusional flow may produce several bubbles per second. Trapped bubbles and the bubbles from diffusional flow may provide a false indication that the filter is defective.

Reverse bubble testing is not well suited for testing a high volume of filters because the test takes a significant amount of time to complete and is subject to observer limitations. Further, it is exceedingly difficult and of limited value to simultaneously conduct a bubble test and a forward flow test. Additionally, it is impractical to reverse bubble test a filter in two different directions because of the limitations of the test apparatus and the filter construction (e.g., cartridge filters). Reverse bubble testing of a filter in an operational environment (on-line testing) is extremely difficult, and impractical under most circumstances. In addition to the above disadvantages, reverse bubble testing does not provide a quantitative assessment of the filter.

As a result of the limitations of reverse bubble tests, in the early 1970's Pall Corporation developed a filtration test known as the forward flow test. See, for example, Dr. D. B. Pall, 1973, "Quality Control of Absolute Bacteria Removal Filters", Parenteral Drug Association, Nov. 2, 1973. Conventional forward flow tests detect defects in a filter by measuring gas flow through a wetted filter. The forward flow test quantitatively measures the sum of diffusive flow and flow through any pores larger than a predetermined size.

In forward flow testing, the filter is typically placed in a test housing. The filter is wetted by immersing the filter in a liquid, such as water or alcohol, until all of the pores of the filter are filled with the liquid. The filter may be wetted by, for example, directing deionized water through the filter for a predetermined period of time. A gas is then directed under pressure against one side of the filter and gas flow through the wetted filter is measured by a flow meter, such as a mass flow meter.

If the filter has no defects, the gas at low pressures is unable to force the liquid from the pores of the filter, so there is very little gas flow, and typically only diffusive gas flow, through the filter. The wetted filter medium behaves like a sheet of wetting solution whose thickness is equal to that of the filter medium. The gas dissolves in the wetting solution, diffuses through it, and then is released downstream of the filter. At lower pressures, the flow per unit of applied pressure remains substantially constant. The flow measured at the lower pressures can be calculated for a given liquid from the known diffusion constant of the applied gas through the liquid.

At a certain higher pressure, known as the bubble point, the gas is just able to force the liquid from some of the largest pores in the filter, and a sudden increase in the flow of gas through the filter can be detected. Of course, as the pressure increases above the bubble point, more and more of the liquid is forced from the pores of the filter and the flow of gas through the filter increases. The slope of the curve after reaching the bubble point provides a measure of the uniformity of the pore sizes in the filter element. A more accurate measure of the "bubble point", is the quantity "$K_L$", coined from the term Knee Location, used to indicate the pressure at which the mass flow curve in a forward flow test bends.

Although the forward flow test is extensively used and is very reliable, it nonetheless has certain drawbacks. For example, the test takes a significant amount of time to complete. A large amount of time is required for gas flow to stabilize before testing can even begin. Once the test does begin, it must be conducted over an extended period of time in order to accurately measure the very small flow rates associated with modern filtration devices. Additionally, there may be a loss of accuracy for on-line testing using forward flow when several dozen filters are tested in parallel without isolating the individual flows through each of the parallel connected filter elements.

SUMMARY OF THE INVENTION

A principal object of the present invention is to alleviate the above-mentioned disadvantages and provide a reliable, economical, and easy-to-operate system and method for testing porous elements. Another principal object of the present invention is to have a relatively short test time and increased accuracy.

Other objects of the present invention include detecting the sound of gas passing through a wetted porous element and analyzing the sound of the gas to discriminate between a defective porous element and a porous element without defects; providing a pass/fail indication for a porous element based on predetermined characteristics of the porous element; discriminating between acoustic signals which indicate that a porous element is defective and acoustic signals which do not indicate that a porous element is defective; minimizing acoustic noise from sources external to the porous element testing system and minimizing electrical noise from circuits contained within the porous element testing system; providing a porous element testing system or method which is compatible with conventional forward flow testing techniques; and detecting defective porous elements regardless of the direction that the porous element is pressurized.

Accordingly, the present invention provides a sonic bubble point test conducted by detecting sound, for example ultrasound, produced when a wetted porous element is exposed to a differential pressure that is less than the bubble point (i.e. a pressure less than the pressure at which the liquid if forced from the largest pores of a homogeneous pore structure). In a preferred embodiment, the sound may be detected while a fluid in a gaseous phase is disposed over both upstream and downstream surfaces of the wetted porous element. Methods and apparatuses are provided for analyzing the sound detected to provide a quantitative measure of the integrity of the porous element. In a preferred embodiment, sonic signals (preferably air-borne sonic signals) from known non-defective filter elements are compared with sonic signals from known defective filter elements to determine test parameters by which a testing apparatus can discriminate between non-defective and defective filter elements. Defects can be detected at differential pressures substantially below the bubble point so that the methods and apparatuses according to the present invention can be conducted simultaneously with forward flow tests. The sonic bubble point test is not subject to the traditional false positive failures attributable to conventional bubble point tests, and is thus capable of being automated.

The present invention provides a porous element testing system including a housing divided into first and second sides by the porous element and a differential pressure generator for generating a differential pressure across the porous element. A transducer is disposed in the vicinity of the porous element for receiving acoustic signals generated within the housing. A signal processing device quantifies acoustic signal data detected by the transducer.

A method for carrying out the invention includes determining whether a porous element is defective by quantifying acoustic signal data.

The present invention may also provide a porous element testing system including a housing divided into first and second sides by the porous element. A differential pressure generator for generating a differential pressure across the porous element. A transducer, disposed in the vicinity of the porous element, for receiving acoustic signals generated within the housing. A signal processing device receives the acoustic signals, and correlates the acoustic data with other non-acoustic system response data, to discriminate between defective and non-defective filters.

A method for carrying out the invention includes quantifying acoustic data, quantifying non-acoustic system response data, and using both the acoustic data and the non-acoustic system response data to discriminate between defective and non-defective filters.

BRIEF DESCRIPTION OF THE DRAWINGS

FIGS. 16 and 17A–F are graphical representations of typical software programs employed by the embodiment of the testing apparatus illustrated in FIG. 12.

FIG. 19 is graphical representations of typical front panel screen displayed during a dynamic pressure test of a non-defective porous element according to the embodiment of the testing apparatus illustrated in FIG. 12.

FIGS. 24 and 25 are flow charts of exemplary test sequences for determining whether a porous element is defective.

FIG. 28 is a tabular representation showing typical characteristics of an acoustic pulse which may be quantified.

DESCRIPTION OF EMBODIMENTS

Systems and methods embodying the present invention may be used to quickly and reliably test the integrity of a wide variety of porous elements. For example, the porous element may comprise a porous medium such as a porous membrane, a porous fibrous sheet or mass, porous, hollow fibers, a woven or non-woven mesh, and/or a porous sintered or non-sintered structure. The porous element may also comprise a cartridge or module having one or more of the following components: a porous medium, a porous support, drainage material, a support plate, an end cap, a core, and a cage. Further, the porous element may comprise an assembly including, for example, a housing containing a porous medium and one or more conduits or fittings associated with the housing. The porous element may have any desired geometry; for example, it may be configured as a solid or hollow cylinder, a disk, or a flat or non-flat sheet. In addition, the porous element may have any desired pore size and distribution; for example, it may be microporous or ultraporous and it may have a uniform or graded pore distribution.

Systems and methods embodying the present invention may be used to determine the presence of a wide variety of defects in porous elements. These defects include not only pin holes or tears in a porous medium but also irregularities in the porous medium such as uncommonly large pores. These defects also include faulty bonds, for example, between a porous medium and an end cap, cracks or holes, for example, in an end cap or a housing, and other flaws through which gas may pass.

Figure 1:
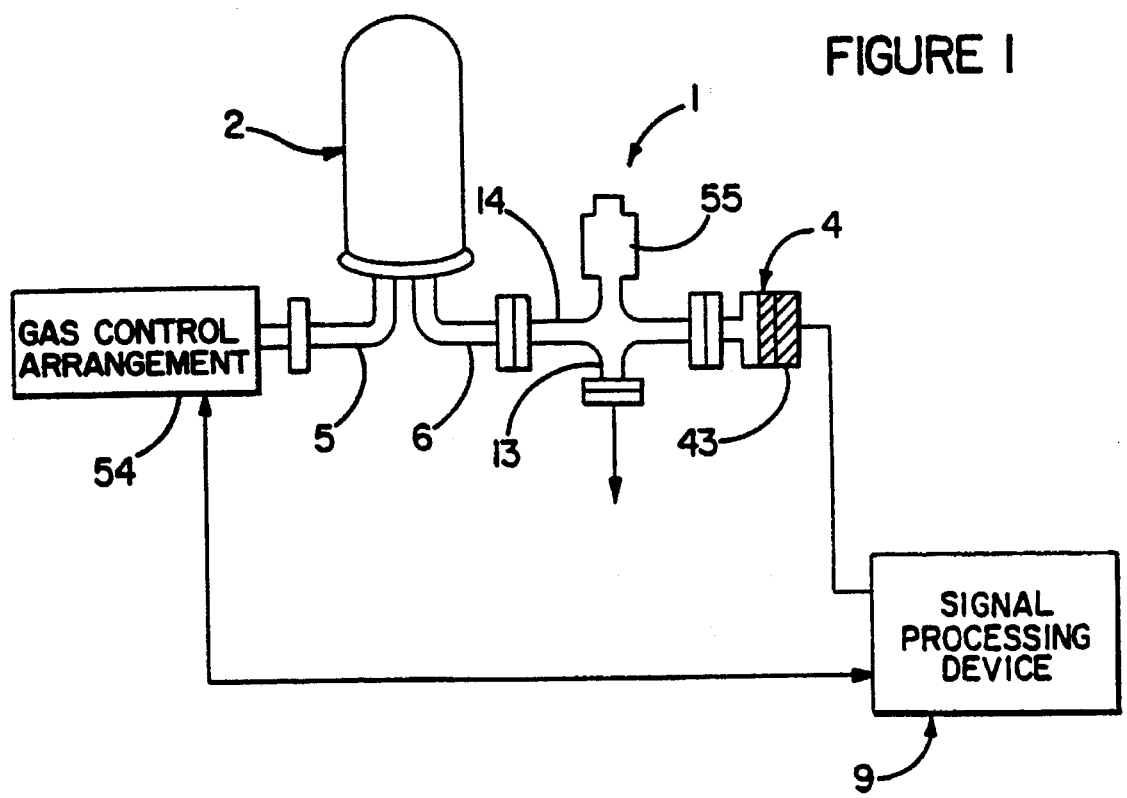
FIG. 1 is a plan/block diagram of the porous element testing system according to one embodiment of the invention.
Figure 2:
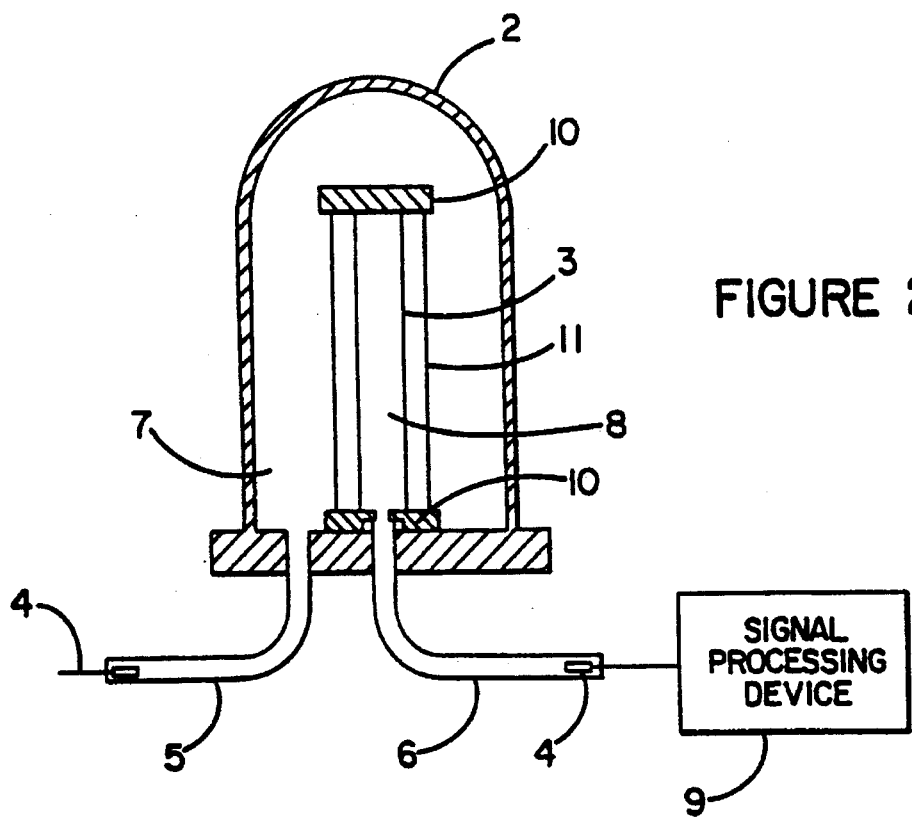
FIG. 2 is a sectional view of one embodiment of the test housing shown in FIG. 1.

As shown in FIGS. 1 and 2, one example of a porous element testing system 1 embodying the invention incorporates a housing 2 coupled to an inlet tube 5 and an outlet tube 6. The housing may be the housing normally containing the porous element during routine filtration operations. Alternatively, the housing may be a housing used solely for testing and having a geometry suitably adapted to the geometry of the particular type of porous element to be tested. For example, the housing may simply comprise two impervious plate-shaped pieces between which a sheet of a porous element is sandwiched. Using this arrangement, bulk filtration material can be tested during the manufacturing process. In the illustrated porous element testing system 1, the housing 2 has a generally cylindrical geometry and is adapted for testing a hollow, cylindrical filter 3 having a porous medium 11. The outlet tube 6 may incorporate a fitting 14 that has a first tube which is connected to the outlet tube 6, a second tube which may be coupled to a microphone 4, a third tube which provides a drain 13, and an optional fourth tube coupled to a flow meter 55. The fitting 14 may include an elastomeric fitting 43 in which the microphone 4 is placed, and serve to acoustically isolate the microphone 4 from external acoustic signals. The fitting 14 may also seal the microphone to the outlet tube to prevent gas bypass. The microphone 4 is preferably coupled to a signal processing device 9.

The filter 3 is preferably first wetted and placed in the housing 2. The filter 3 is positioned such that it separates the housing 2 into an inlet side 7 and an outlet side 8. A gas control arrangement 54 may be coupled to an inlet tube 5. The inlet tube 5 is, in turn, coupled to the inlet side 7 of the housing 2. The outlet tube 6 is coupled to the outlet side 8 of the housing 2. Although the illustrated microphone 4 is coupled to the fitting 14, it may alternatively or additionally be placed in any number of locations. For example, the microphone may be placed within the outlet tube 6, preferably near the junction of the outlet tube 6 and the outlet side 8 of the housing 2, in the outlet side 8 of the housing 2, in the inlet side 7 of the housing 2, and/or in the inlet tube 5. In many embodiments it is preferable to locate the microphone 4 within a line-of-sight of the porous element. Placing the microphone 4 within a line-of-sight of the porous element reduces distortions and increases the sound pressure level at the microphone. In the most preferred embodiment, the microphone is located in the inlet tube or the outlet tube to provide improved discrimination between defective and non-defective porous elements.

The signal processing device 9 analyzes the sound pressure level detected by the microphone in order to perform a variety of desirable functions. For example, the signal processing device 9 most preferably discriminates between defective porous elements and porous elements without defects. It also may be used to determine characteristics of the porous element, such as pore size, or characteristics of the defect, such as size, or other anomalies such as improper wetting.

Figure 3:
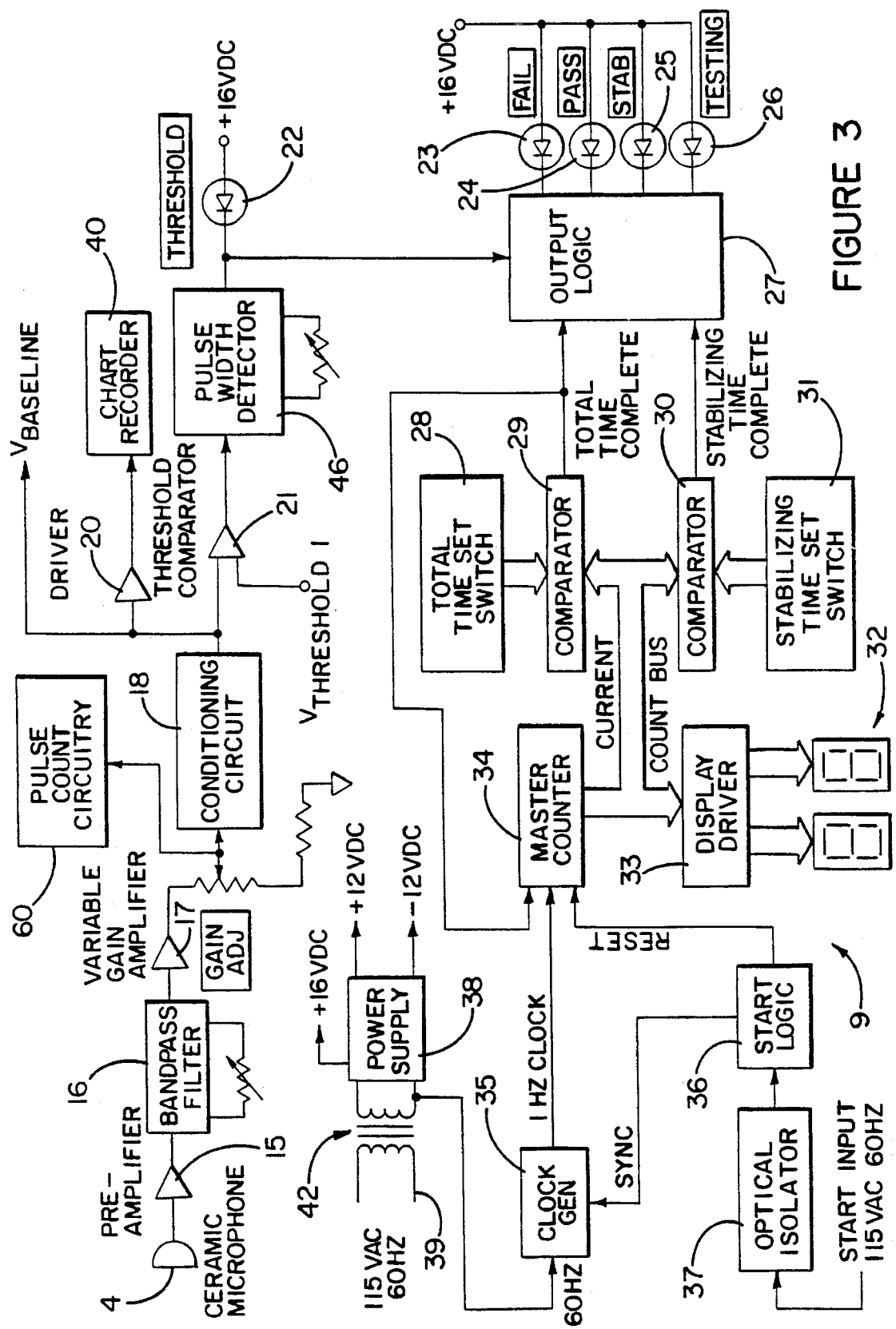
FIG. 3 is a partial block/partial schematic diagram of one embodiment of the signal processing device shown in FIG. 1.
Figure 10:
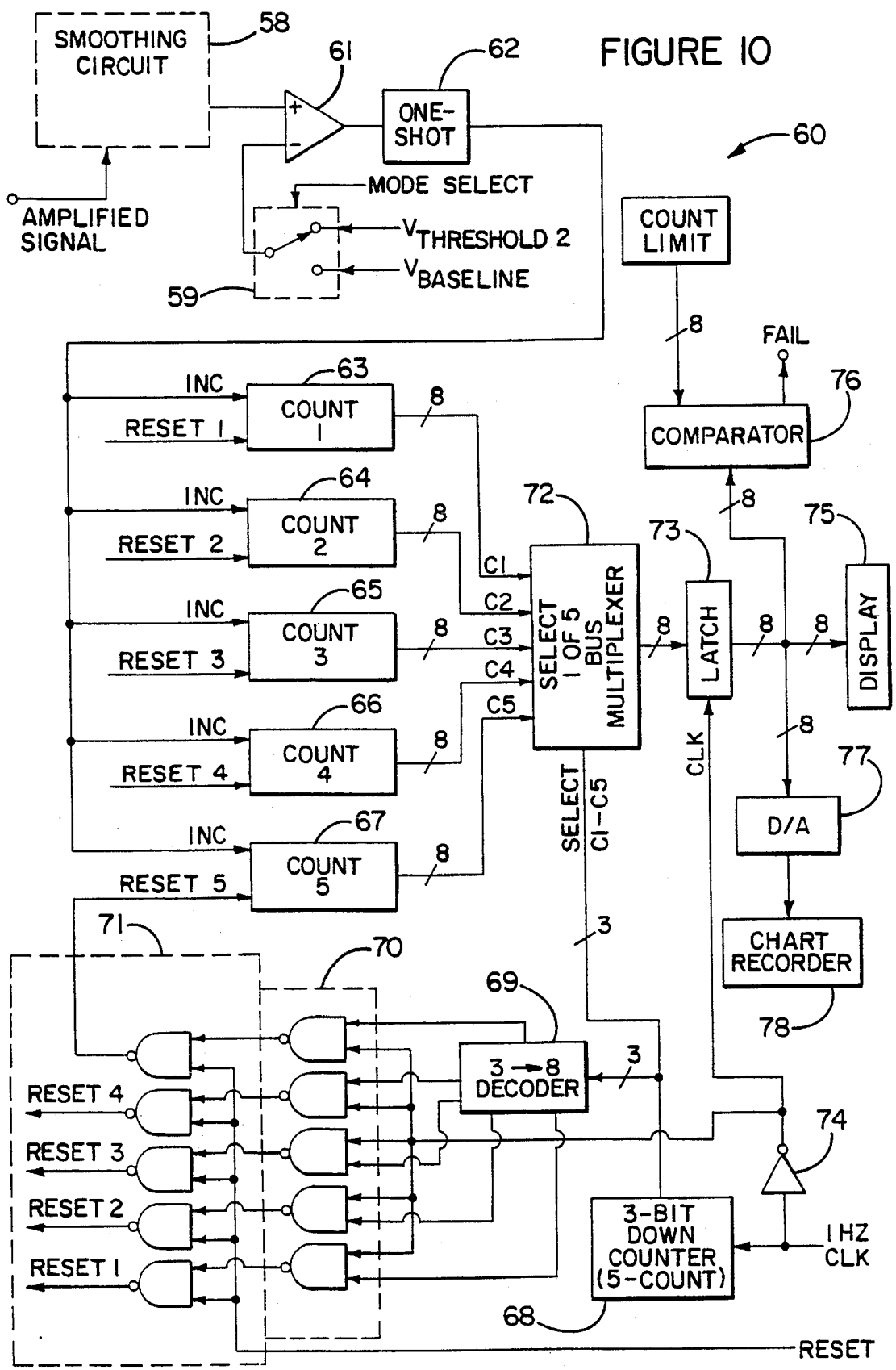
FIG. 10 is a partial block/partial schematic diagram of one embodiment of the pulse count circuitry shown in FIG. 3.

Although the signal processing device 9 may be configured in a variety of ways, one example of the signal processing device 9 is shown in FIG. 3. The microphone 4 detects sound pressure levels within the housing 2 and outputs a signal indicative of the sound pressure level detected. The signal from the microphone 4 is amplified by a pre-amplifier 15 and output as a pre-amplified signal. An adjustable bandpass filter 16 operates to condition the pre-amplified signal. In one embodiment, the bandpass filter 16 filters the pre-amplified signal so that a narrow frequency band is output as a filtered signal. A variable gain amplifier 17 may be provided to amplify the filtered signal to output an amplified signal. The amplified signal is received by a conditioning circuit 18 and by pulse count circuitry 60. An example of one embodiment of the pulse count circuitry 60 is shown in FIG. 10 and discussed in more detail below. The conditioning circuit 18 reshapes the amplified signal and outputs a conditioned signal to an output driver 20 and threshold comparator 21.

The output driver 20 couples the conditioned signal to a visual display device such as a chart recorder 40. The chart recorder 40 may enable an operator to visually detect defects. However, operator analysis of charts produced by the chart recorder require a substantial amount of time and sophistication on the part of the operator and, therefore, the chart recorder is a less preferred embodiment. Additionally, in many circumstances, an operator may not be able to distinguish a faulty filter from an operational filter because of noise without the assistance of additional processing of the signal. A chart recorder may not be sufficiently precise to display low amplitude or short duration responses caused by small defects; however, the chart recorder is certainly adequate to display a response associated with the bubble point of the porous element.

Figure 5:
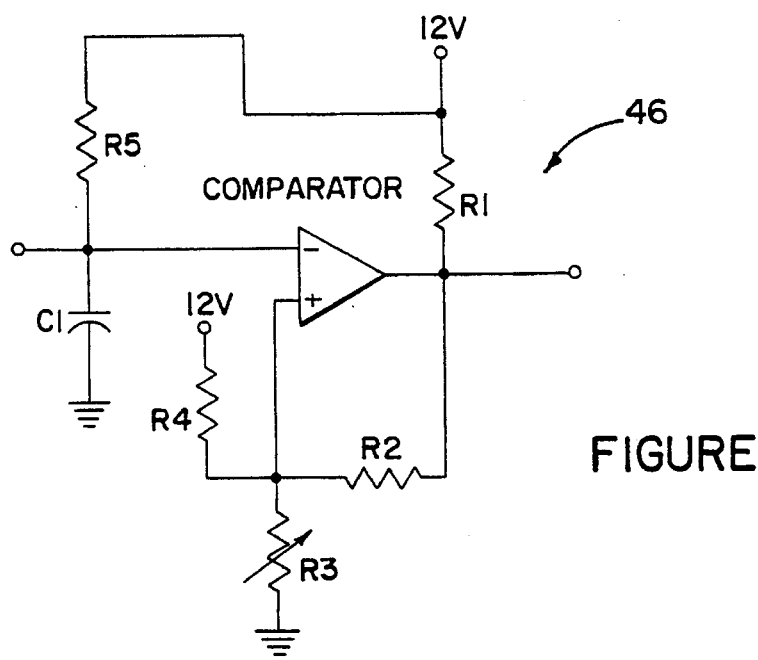
FIG. 5 is a schematic diagram of an embodiment of the pulse width detector of FIG. 3.
Figure 6:
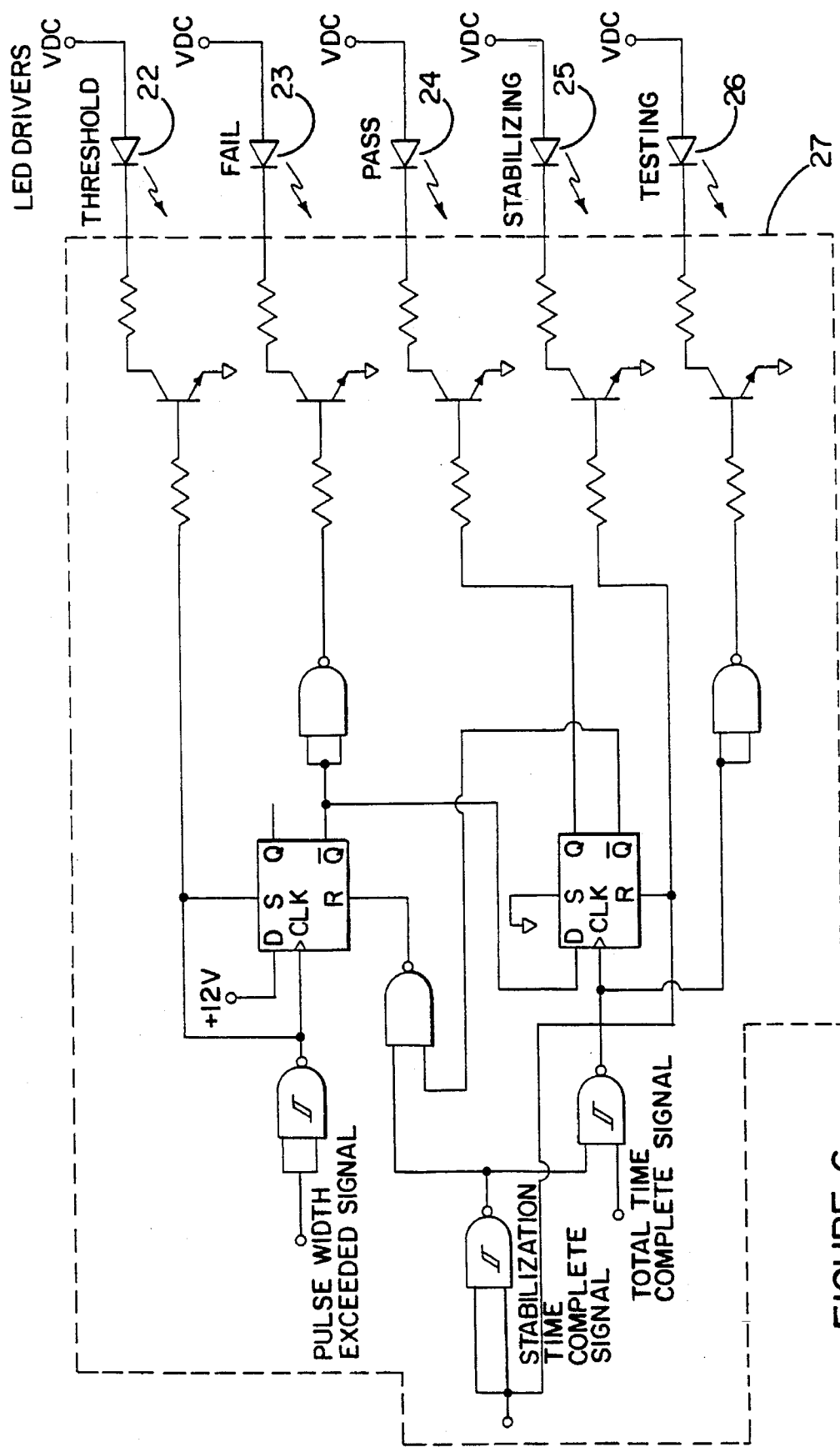
FIG. 6 is a schematic diagram of one embodiment of the output logic of FIG. 3.

The conditioned signal is input into a first input of the threshold comparator 21. A user-variable threshold voltage is input into a second input of the threshold comparator 21. The threshold comparator 21 is coupled to a variable pulse width detector 46 which detects when a signal from the threshold comparator 21 is activated for a predetermined period of time. An example of one embodiment of a pulse width detector 46 is shown in FIG. 5. The variable pulse width detector 46 may output a pulse width exceeded signal to a threshold indicator 22 and output logic 27. The output logic 27 may, for example, be constructed as shown in FIG. 6. Output logic 27 may be coupled to a fail indicator 23, a pass indicator 24, a stabilization indicator 25, and a testing indicator 26.

Any suitable control circuitry for the signal processing device 9 may be provided. In the embodiment illustrated in FIG. 3, a 115 volt power source 39 supplies power to a power supply 38 via a voltage transformer 42. The power supply 38 may provide operational voltages to the components in the signal processing device 9. A 60 Hz input signal from the voltage transformer 42 may be coupled to a clock generator circuit 35. The clock generator may, for example, input the 60 Hz (or 50 Hz) input signal, divides the input signal by 60 (or 50), and produce a 1 Hz clock signal. The 1 Hz clock signal may be input into a master counter 34. Alternatively, the master counter may receive a constant or variable clock having any suitable frequency from a standard oscillator circuit.

A start input may be coupled to start logic 36 via an optical isolator 37. In the illustrated embodiment, the start logic 36 is coupled to the master counter 34 via a reset signal and coupled to the clock generator 35 via a sync signal. The master counter 34 may be coupled to a display driver 33, a total test time comparator 29, and to a stabilization time comparator 30 via a current count bus signal. The display driver 33 is coupled to a display 32. The total test time comparator 29 has a first input connected to the current count bus, a second input connected to a total test time set switch 28, and an output connected to the output logic 27 and the master counter 34. The stabilization time comparator 30 has a first input connected to the current count bus, a second input connected to a stabilization time set switch 31, and an output connected to the output logic 27.

In a preferred mode of operation, the porous element, e.g., the filter element 3, is wetted with a suitable wetting solution such as water and/or alcohol. A preferred wetting solution for many hydrophobic filters is a mixture of water (75 parts by volume) with tertiary butyl alcohol (25 parts by volume), known by the trade designation Pallsol. The filter 3 may be wetted before or after it is placed in the housing 2. With the wetted filter 3 sealed within the housing 2, a gas is then introduced into the housing 2 through either the inlet tube 5 or the outlet tube 6. For many tests, the gas is preferably introduced through the inlet tube 5. Alternatively, the filter may be pressurized from the inside out by introducing the gas into the housing 2 through the outlet tube 6.

In one embodiment, the gas is introduced into the housing 2 by the gas control arrangement 54, which may be coupled to or independent of the signal processing device 9. In a preferred embodiment, the gas control arrangement may be part of a forward flow test system and the porous element testing system may be coupled to and function in conjunction with the forward flow test system. In any event, the housing 2 may be pressurized gradually, e.g., by ramping the pressure, or, more preferably, it may be stepped to a predetermined value. The predetermined value may range from 50% to 95%, or preferably from 60% to 90% or more preferably from 75% to 85%, or most preferably the predetermined value is 80% of the predicted bubble point of the filter 3.

At pressures below the bubble point, only a small amount of gas should diffuse through the porous medium 11 of the filter 3 and the microphone 4 should not detect the sound of the gas passing through either the pores of the porous medium 11 or a defect in the filter 3. If the sound of gas passing through the pores or a defect is detected by the microphone 4 at pressures below the bubble point, then the filter 3 is likely to be defective. For example, the porous medium itself may be defective due, for example, to abnormally large pores, a hole, or a tear. Alternatively, the filter 3 may be defective due, for example, to a defective bond between the porous medium and the end caps or due to a crack in the end caps.

In the embodiment shown in FIG. 3, the start logic 36, in response to the start input, operates to reset the master counter 34, and subsequently enables the clock generator 35 to supply the 1 Hz clock to the master counter 34. The start input may be provided manually by the user or occur automatically as the housing 2 is pressurized. For example, the start input may be received from a 115 volt power source which is energized once the gas control arrangement 54 pressurizes the housing 2. The master counter 34 may count up in one second intervals, or at a lessor or greater interval. In the preferred embodiment, the current count bus signal output by the master counter 34 is indicative of the number of seconds that have been counted since the test was initiated by the start logic 36. The display driver 33 receives the current count bus signal indicative of the number of seconds elapsed, and displays the number of seconds elapsed on the display 32. The display 32 may provide a visual indication of the progress of the ultrasonic test.

The stabilization comparator 30 receives the current count bus signal from the master counter 34 and compares the current count against a stabilization time indicated by the stabilization time set switch 31. The time indicated by the stabilization time set switch 31 may vary depending, for example, on characteristics of the porous element such as pore size, the size and physical configuration of the porous element, etc. Exemplary stabilization times may be in the range up to about 15–20 seconds. When the stabilization comparator 30 detects that the predetermined stabilization time has been reached, the stabilization comparator 30 outputs a stabilization time complete signal to the output logic 27. The stabilization complete signal causes the output logic 27 to begin monitoring the pulse width exceeded signal for indicating a failure whenever this signal is activated after the stabilization period.

The total test time comparator 29 receives the current count bus signal from the master counter 34 and compares the current count against a total test time indicated by the total test time set switch 28. The time indicated by the total test time set switch 28 may also vary depending, for example, on the characteristics of the porous medium and the desired parameters of the test. Exemplary total test times may be in the range up to about 45–50 seconds. When the total test time comparator 29 detects that the predetermined total test time has been reached, the total test time comparator outputs a total time complete signal to the output logic 27 and the master counter 34. The master counter 34 may then inhibit further counting in response to receiving the total test time complete signal so that counting will not resume until the master counter 34 has been again reset by the start logic 36.

Throughout this timing sequence, the microphone 4 outputs a signal responsive to the sound detected by the microphone 4. The microphone 4 may be any suitable transducer for converting sound pressure into electrical energy. If the microphone 4 is of the piezo-ceramic type, then the microphone 4 will only be resistive at the resonant frequency and at an anti-resonance frequency. To optimize electrical to mechanical efficiency for transmitting, a piezo-ceramic transducer is preferably operated at the resonance frequency. To optimize mechanical to electrical efficiency for receiving, the piezo-electric transducer is preferably operated at the anti-resonance frequency.

The microphone 4 is preferably a piezo-electric crystal transducer and the optimum mechanical to electrical frequency of the microphone 4 is preferably in the range of about 30 to about 50 KHz and more preferably about 40 KHz. A frequency above 30 KHz avoids ambient acoustic noise and a frequency below 50 KHz avoids inherent electrical noise generated by high frequency circuity. Under normal test conditions, the signal from the microphone is on the order of 1 microvolt (1 uV) at a frequency of about 40 KHz.

It has been found that drops of liquid on the microphone 4 may reduce the sensitivity of the microphone 4. Therefore, it is desirable to shield the microphone 4 from the wetting solution or other liquids by, for example, placing the microphone 4 downstream from the drain 13, heating the microphone 4 by means of a heating element (not shown) in order to evaporate the liquid, polishing the microphone dome to a highly smoothed surface, and/or by applying a voltage to the microphone to vaporize any liquid on the microphone by sonic vibrations.

The microphone may be constructed with a highly smoothed or polished surface obtained, for example, by electro-polishing the dome of an ultrasonic transducer. The polished surface prevents liquids from being trapped in pores or depressions on the surface and results in a hydrophobic microphone. By hydrophobic it is meant that any wetting fluid which comes in contact with the microphone beads and rolls off without wetting the surface of the microphone. The highly polished surface preferably has no more than 10 micro inches of discontinuity (Ra=10), or more preferably no more than 8 micro inches of discontinuity (Ra=8), or even more preferably no more than 6 micro inches of discontinuity (Ra=6), or most preferably no more than 4 micro inches of discontinuity (Ra=4). In one embodiment, electro-polishing of the microphone is continued until the microphone 4 is optimized to maximize the mechanical to electrical efficiency at a predetermined frequency of, for example, at about 40 KHz. In a preferred embodiment, the dome of the microphone is manufactured using stainless steel. A stainless steel microphone may be used in on-line testing applications without danger of contamination or leaching into the system being tested. The microphone 4 is also safely used in a gaseous environment containing volatile solvents and/or wetting solutions since the microphone 4 contains no stored energy.

The pre-amplifier 15 amplifies the signal received from the microphone to a voltage preferably on the order of 1 V. The signal-to-noise ratio (S/N) of pre-amplifier 15 is limited by the self-generated noise of the pre-amplifier itself. The noise is determined by the source resistance, the type of active circuit, and the bandwidth of the signal. It is desirable to maximize the signal-to-noise ratio for the pre-amplifier 15 to increase the sensitivity of the system.

The preferred pre-amplifier 15 may be an operational amplifier commercially available from Precision Monolithics Incorporated (PMI), Santa Clara, Calif., or Motorola, under the trade designation OP-27. The OP-27 operational amplifier is an ultra-low noise operational amplifier. In a preferred embodiment, a preamplifier with a S/N of 5.0 or more is preferred for use in pre-amplifier 15.

The adjustable bandpass filter 16 is preferably designed to have a center frequency corresponding to the optimum mechanical to electrical conversion frequency of the microphone 4. In a preferred embodiment, the bandpass filter has a bandwidth of 2 KHz and a Q of approximately 20, and is implemented using a biquadratic filter, also known as a state-variable bandpass filter. This filter was found to provide adequate performance with minimum costs, and therefore is a preferred embodiment. It was also found to provide a high probability of detecting a defective porous element, while at the same time minimizing the probability that a properly functioning porous element would be detected as defective (i.e., a false positive result). A filter with narrower bandwidth (higher Q) could be implemented with increased cost and complexity, resulting in improved S/N. Conversely, a simpler filter or no filter could be utilized, but this may result in an increased S/N and is therefore not preferred for time domain analysis of the signal from the microphone 4.

The adjustable bandpass filter 16 has an adjustable center frequency and bandwidth. It has been found that a center frequency of over 35 Khz is preferable because there is much less ambient noise generated by outside environmental factors in this frequency range.

It has been found that the reliability of the system can be greatly increased by reducing the internally generated noise of the pre-amplifier 15 and narrowing the bandwidth of the adjustable bandpass filter 16 around a center frequency corresponding to a frequency at which the porous element generates the largest signal. The frequency at which the porous element generates the largest signal may be the frequency of the sound generated by the largest pores in the porous element. It was found that for some porous elements, the frequency having the maximum amplitude occurs at about 40 KHz.

The variable gain amplifier 17 has a gain that can be varied in response to the position of the microphone relative to the porous element or in response to the characteristics of porous element being tested. The variable gain amplifier 17 allows a plurality of porous element testing systems to be calibrated so that a single set of test criteria is valid for each of the porous element testing systems.

The conditioning circuit 18 may be constructed to discriminate between noise spikes (having a low voltage and/or infrequent occurrence) and a signal produced by a truly defective porous element. The characteristics of the conditioning circuit 18 may be set such that an isolated short noise spike will not appreciably alter the signal output from the conditioning circuit 18. However, if a plurality of short noise spikes are received within a relatively short period of time, the voltage of the conditioned signal may be conditioned to track the average voltage (baseline) of the noise spikes. In one embodiment, the conditioning circuit has a rise time of 0.5 milliseconds and a fall time of 2.5 milliseconds.

Figure 4A:
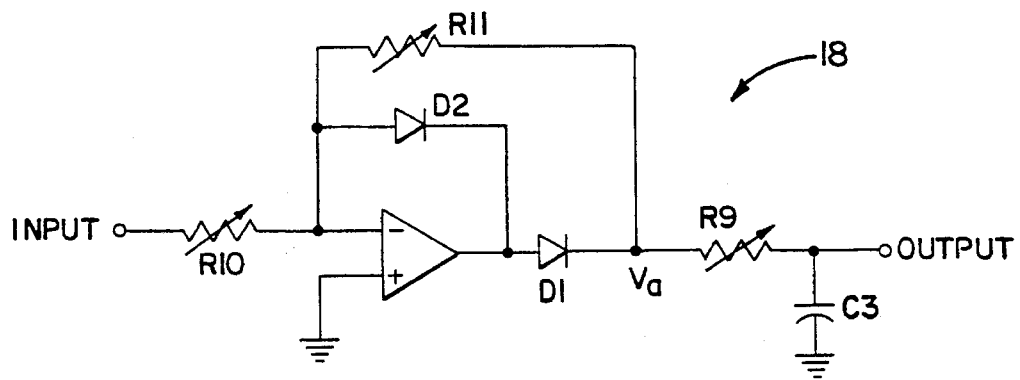
FIGS. 4A and 4B are a schematic diagrams of embodiments of the conditioning circuit of FIG. 3.
Figure 4B:
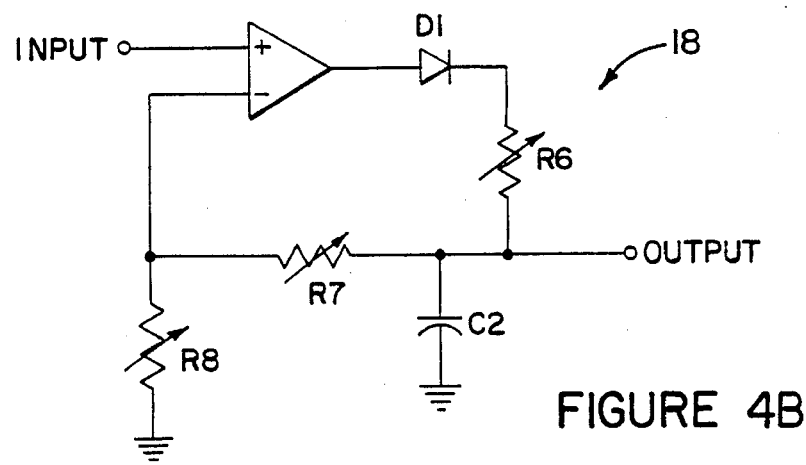

Examples of suitable conditioning circuits are shown in FIGS. 4A and 4B. FIG. 4A shows a half-wave rectifier cascaded with a low pass filter (R9, C3) forming what is commonly known as an average detector.

FIG. 4B shows a conditioning circuit including a plurality of resistors in the feed-back circuitry. If resistor R6 and R7 are very small, and resistor R8 is very large, then the circuit in FIG. 4B acts as a classic peak detector where the output is a constant voltage corresponding in value to the highest voltage spike (the peak) detected at the input. The classic peak detector arrangement is useful for providing a simple detection of the bubble point response or for mapping the maximum amplitude of the pulses received at the input. By increasing the resistances of R6 and R7 and decreasing the resistance of R8, the peak detector can be modified to include finite rise and fall times. In this configuration, the conditioning circuit may average the pulses received at the input signal and/or generate an output which tracks the baseline of the input signal.

The threshold comparator 21 may operate to compare the signal output from the conditioning circuit 18 with the threshold voltage. The threshold voltage may be varied to adjust for the parameters of the test setup, such as microphone position, and/or the characteristics of the porous element. Additionally, the level of the threshold voltage may be adjusted depending on, for example, the level of the applied pressure. Whenever the conditioned signal exceeds the threshold voltage, the threshold comparator 21 outputs a threshold detect signal. The threshold detect signal may be input into a variable pulse width detector 46 which detects whenever the threshold detect signal has been continuously activated for a predetermined time period. The predetermined time period is adjustable, and, in the preferred embodiment, can be adjusted between about 0.01 and about 1.0 second. The variable pulse width detector 46 outputs a pulse width detect signal whenever the pulse width of the threshold detect signal exceeds the predetermined time period. The pulse width detect signal preferably activates the threshold indicator 22 and provides a visual indication whenever the threshold voltage is exceeded for the predetermined time period.

The conditioning circuit 18 and the threshold comparator 21 provide a means for measuring when the average sound pressure level continuously exceeds a threshold level for a predetermined period of time. Detecting the sound pressure level may be implemented in other ways, including, for example, such as an RMS circuit or a low pass filter/integrator circuit.

When an ultrasonic test is initiated, the stabilizing indicator 25 may turn on and remain illuminated for a stabilizing time period determined by the stabilizing time set switch 31. Typically, the stabilizing time set switch 31 is set to indicate a time of about 15–20 seconds. During this time the housing 2 is pressurized and the wetted porous element stabilizes. During the stabilization period, the signal from the threshold comparator 21 is ignored.

Figure 7:
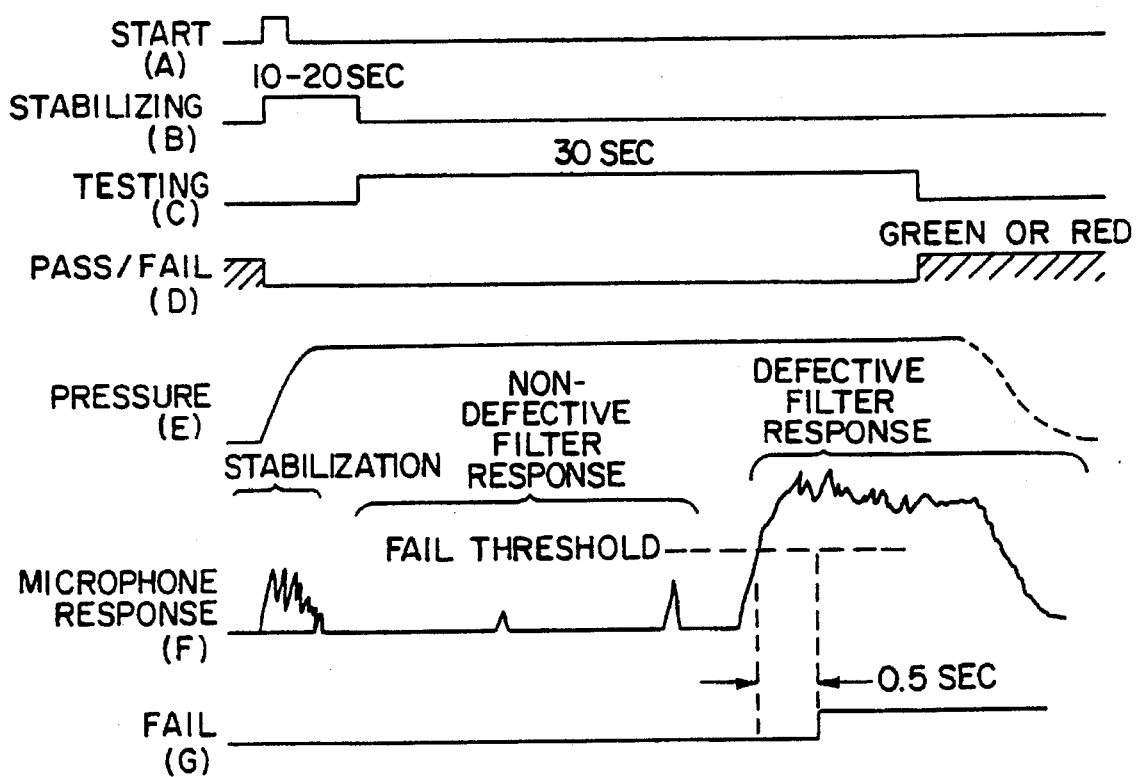
FIGS. 7A–G are graphical representations of a testing cycle according to the first embodiment of the signal processing device illustrated in FIG. 3.

Referring to FIG. 7, following the start input (FIG. 7A), the stabilizing indicator 25 is illuminated (FIG. 7B). The stabilize indicator 25 remains on for the time necessary to increase the pressure in the housing 2 and allow the microphone response to stabilize (stabilization time). An exemplary simplified microphone response is shown in FIG. 7F, with the stabilizing period specifically identified. The stabilizing indicator 25 turns off after the filter has stabilized (typically 15–20 seconds), and the testing indicator 26 may then be illuminated. The testing indicator 26 remains on until the test is complete as determined by the total test time set switch 28. Typically, the testing indicator 26 remains on for a period of about 45–50 seconds. During this period, the threshold detector signal may be examined by the output logic 27.

A porous element which is not defective may nevertheless have a response that includes a number of noise spikes. These noise spikes were found to be present in non-defective porous elements and are believed to be due to a variety of causes, including: (a) liquid dripping from the porous element 3 into the housing 2, into the outlet tube 6, and/or onto the microphone 4; (b) liquid moving on the surface of the porous element, the housing, and/or the microphone, (c) external acoustical noise from outside of the test set-up, (d) self generated electrical noise caused by the electronics of the signal processing device 9, and/or (e) bubbles on the surface of the porous element.

Several measures have been found to reduce this noise and increase overall system sensitivity including:

a) increasing the signal to noise ratio for the microphone 4, pre-amplifier 15, bandpass filter 16, and variable gain amplifier 17;

b) incorporating a high Q bandpass filter optimized to the optimum mechanical to electrical efficiency frequency of the transducer;

c) shielding the microphone 4 from external acoustic noise, e.g., by placing the microphone 4 inside of the elastomeric fitting 43, the housing 2, the inlet and/or the outlet tubes;

d) shielding the preamplifier 15 from external electrical noise, e.g., by placing the preamplifier 15 inside of a conductive enclosure capable of shielding the preamplifier 15 from external electromagnetic radiation and by reducing the electromagnetic radiated emissions from other portions of the circuit;

e) pre-pressurizing the assembly at half the anticipated bubble point test pressure before increasing to the full test pressure (note that small porous elements do not require this pre-pressurization procedure since the pressurization time necessary to remove excess wetting solution is substantially inversely proportional to the surface area of the porous medium);

f) vacuuming excess wetting solution from the surface of the porous medium;

g) shielding the microphone from any contact with the wetting solution by, for example, placing the microphone downstream from the drain;

h) electro-polishing the surface of the microphone to form a hydrophobic surface;

i) incorporating a circuit to de-pressurize the housing 2 before it is opened after the test, preventing the high pressure inlet side from blowing wetting solution into the low pressure outlet side and onto the microphone surface;

j) removing any liquid from the surface of the microphone;

k) using separate analog and digital power supplies or voltage regulators to prevent coupling through the power supply, eliminating ground loops to prevent coupling between the digital and analog portions through the common supply, and using slow CMOS to reduce current modulation; and l) coupling the microphone 4 to the preamplifier 15 using shielded cable.

Despite these efforts, it has been found that some noise spikes or glitches still remain. Consequently, the signal processing device incorporates an arrangement such as the conditioning circuit 18, the pulse width detector 46, a pulse counter and/or other suitable circuitry to discriminate noise spikes present in a non-defective porous element from the noise made by a defective porous element.

For example, a microphone response for a hypothetical defective porous element is illustrated in FIG. 7F. Whenever the pulse width detect signal indicates that the threshold voltage has been continuously exceeded by the conditioned signal for more than a predetermined noise limit period (typically 0.01–1.0 seconds), a failure may be indicated by illuminating the fail indicator 23, as shown in FIG. 7G. If the pulse width detect signal indicates that the threshold voltage has not been continuously exceeded by the conditioned signal for the noise limit time period (typically 0.01–1.0 seconds), the pass indicator 24 may be illuminated.

Throughout the ultrasonic test, the master counter 34 may increment to mark the test time. The master counter 34 typically increments from 1 to about 45–50. The pass indicator 24 or the fail indicator 23 remains on until the start of the next test cycle. In order to calibrate the system response with the physical characteristics of a particular filter to be tested, it may be preferable to adjust the noise limit time, the stabilizing time, the total test time, the bandwidth of the bandpass filter 16, the gain of the variable gain amplifier 17, the rise and fall time of the conditioning circuit 18, the threshold voltage of the threshold detector 21 and the pulse width detected by the pulse width detector 46. However, in some production environments, it may be preferable to fix these values for a single type of porous element and/or test system configuration.

Figure 9:
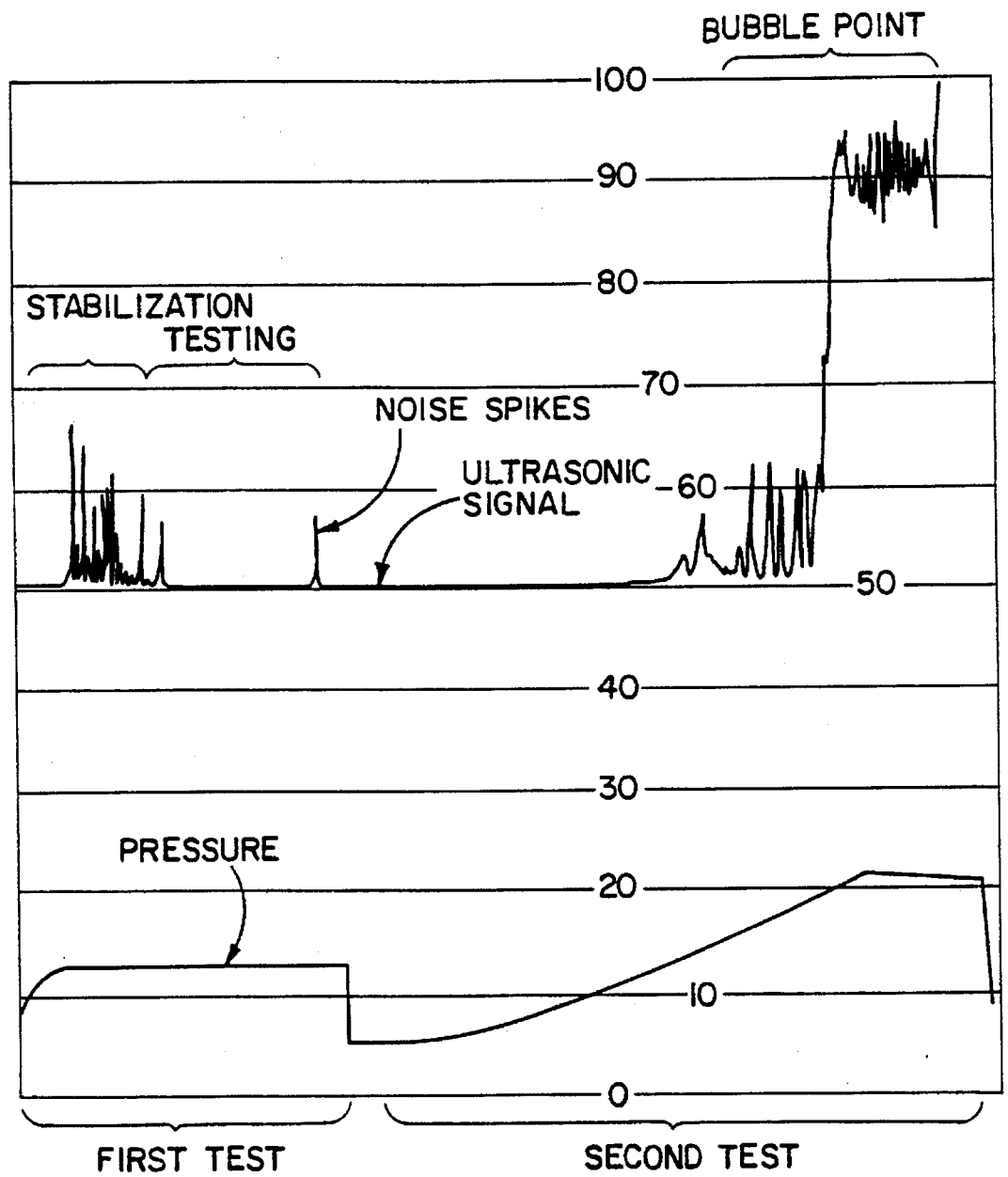
FIG. 9 is a graphical representation of an alternative testing cycle of the apparatus illustrated in FIG. 1.

FIG. 9 illustrates another method for testing a porous element. In this method, a first test is run as described above. This allows the porous element to be characterized as meeting a minimum standard for integrity. Following the first test, a second test is performed to determine the bubble point of the porous element. In the second test the pressure in the housing 2 is slowly increased until the pulse width detect signal indicates that the threshold voltage has been continuously exceeded by the conditioned signal for more than a predetermined noise limit period, indicating that the bubble point has been reached. The pressure at which the porous element reached its bubble point may then be used to calculate the maximum pore diameter for the porous element using well known methods. The second embodiment allows different porous elements to be classified into different grades. It also allows for a quantitative measure of pore size. Pore size characterization is desirable because porous elements may have a bubble point which is too high due to the wrong material, defective materials, or a clogged medium. The measured bubble point can be reported, collected, and analyzed as a check on the manufacturing process.

A sensitivity adjustment is provided which allows the signal processing device 9 to tune from full sensitivity, for example, for ultra porous elements to a reduced sensitivity for macro porous elements. The sensitivity adjustment is typically accomplished by adjusting a combination of the gain on the variable gain amplifier 17 and the threshold voltage value provided to the threshold comparator 21.

Low surface tension liquids can be used with the porous element testing system 1. Because the porous element testing system 1 does not rely on measuring the leak to diffusion ratio, it is relatively unaffected by low surface tension fluids. Low surface tension fluids have the advantage of being superior agents for wetting the porous elements (especially hydrophobic porous elements) and allowing the porous elements to dry quicker once the test has been completed.

In many applications, it may be desirable to perform both forward flow tests, which are well known in the art, and ultrasonic tests embodying the invention on the same porous element. It has also been found to be desirable to perform ultrasonic testing in both the forward and reverse direction. Performing both a forward flow test and ultrasonic tests on the same porous element has been found to provide improved reliability. It has been determined that it is even more effective to conduct both tests simultaneously.

The porous element testing system 1 can be installed in existing forward flow test stands or in on-line testing applications with minimal modification. For on-line applications, it is now practical for a end-user to conduct on-line reverse bubble-point testing of filters without the requirement to visually observe the filter. Conventional bubble point tests required an operator to observe the filter or employ an ultrasonic detector coupled to the filter via a liquid medium. The liquid medium is extremely disadvantageous because the ultrasonic transducer is coupled to noise sources originating down-stream from the filter-under-test as well as noise sources originating in structures adjacent to the fluid filed piping. The signal to noise level masks the defective filter signals. Additionally, during visual reverse bubble testing, an operator can distinguish bubbles resulting from diffusional flow from bubbles caused by defects by prodding the filter with a probe and watching whether the source location of the bubbles moves. However, in on-line testing or automated testing using fluid coupled ultrasonic sensors, it is frequently not possible to distinguish between diffusional flow and true leaks. Because of these problems, conventional fluid coupled ultrasonic testing arrangements are typically limited to laboratory environments, and require extensive insulation. Even with these measures, conventional fluid coupled ultrasonic testing apparatuses are limited to identifying gross sound levels such as the large increase in sound levels that occur at the bubble point. By contrast, embodiments of the present invention are not as susceptible to environmental noise and provide greatly increased discrimination between defective and non-defective filters. It has been found that the use of air or other gaseous phase fluids to couple the microphone to the porous element better insulates the microphone from extraneous noise sources, while still permitting the microphone to detect sounds produced by the filter medium. Thus, the gaseous coupled ultrasonic testing makes reverse bubble testing in operational environments possible.

Forward flow testing and ultrasonic testing can be performed simultaneously, and, generally, performing both tests simultaneously does not require any more time than the time required by a single forward flow test. The housing 2 is preferably pressurized to the same pressure as specified for a forward flow test. The microphone 4 can be placed in the downstream part of the outlet tube 6 and left there, even during sterilization. This is possible because the preferred microphone 4 is capable of operating after exposure to temperatures in excess of 300° F.

Another embodiment of the ultrasonic leak detector employs a sonic test method for assessing the integrity of porous elements. The test method is termed the "pulse count test" and measures the pulse density of sound pressure levels generated by a wetted porous element as a gas pressurizes the up-stream surface of the porous element. It has been found that this testing method is a very effective tool in discriminating properly functioning filters from defective ones.

Wetted filters under pressure produce a number of sound pressure pulses, superimposed on a baseline signal level. FIG. 9 shows a typical response of a filter where the sound pressure has been converted to electrical energy by the microphone 4, amplified, filtered, and conditioned. The graphical representation shown in FIG. 9 is a simplified response. Detailed graphs of the response of typical non-defective and defective filters are respectively shown in FIGS. 13 and 14.

Figure 13:
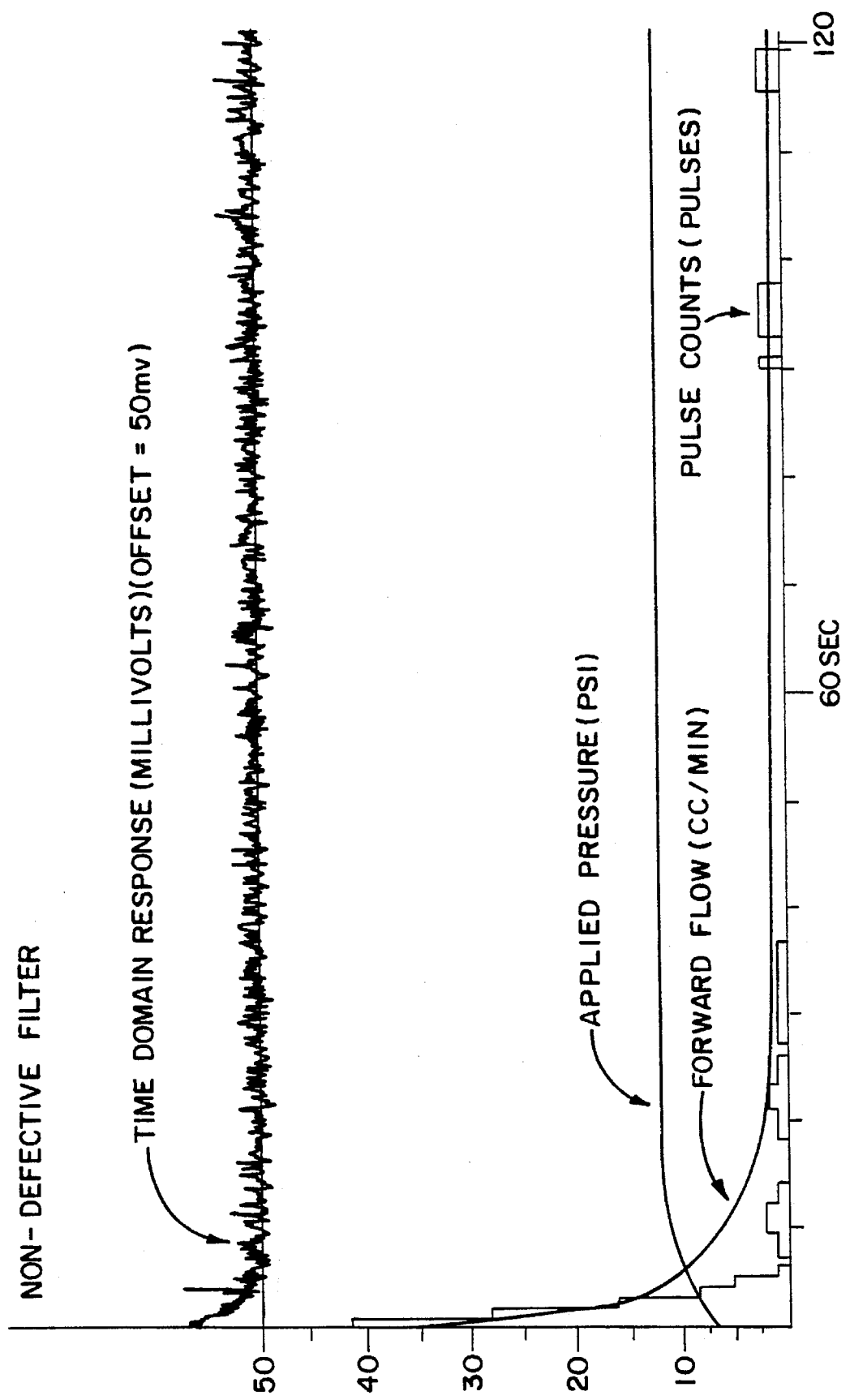
FIG. 13 is a graphical representation of a testing cycle of a non-defective filter according to the embodiment of the testing apparatus illustrated in FIG. 12.

Referring to FIG. 13, the microphone response of a non-defective filter is shown as the applied pressure is increased to a level below the bubble point. As the initial pressure is increased, the forward flow curve shows a higher initial flow followed by a stable flow rate. The higher initial flow results from, for example, flexing of the filter in the down stream direction in response to the applied pressure. The period of time required to reach a stable flow is termed the stabilization time. Similarly, the sound level within the test chamber increases initially as the porous element is pressurized, followed by a relatively stable sound pressure level. Much of the signal activity during the relatively stable portion of the sound pressure level period in FIG. 13 is attributable to noise. The pulse counts per unit time are shown at the bottom of FIG. 13.

Figure 14:
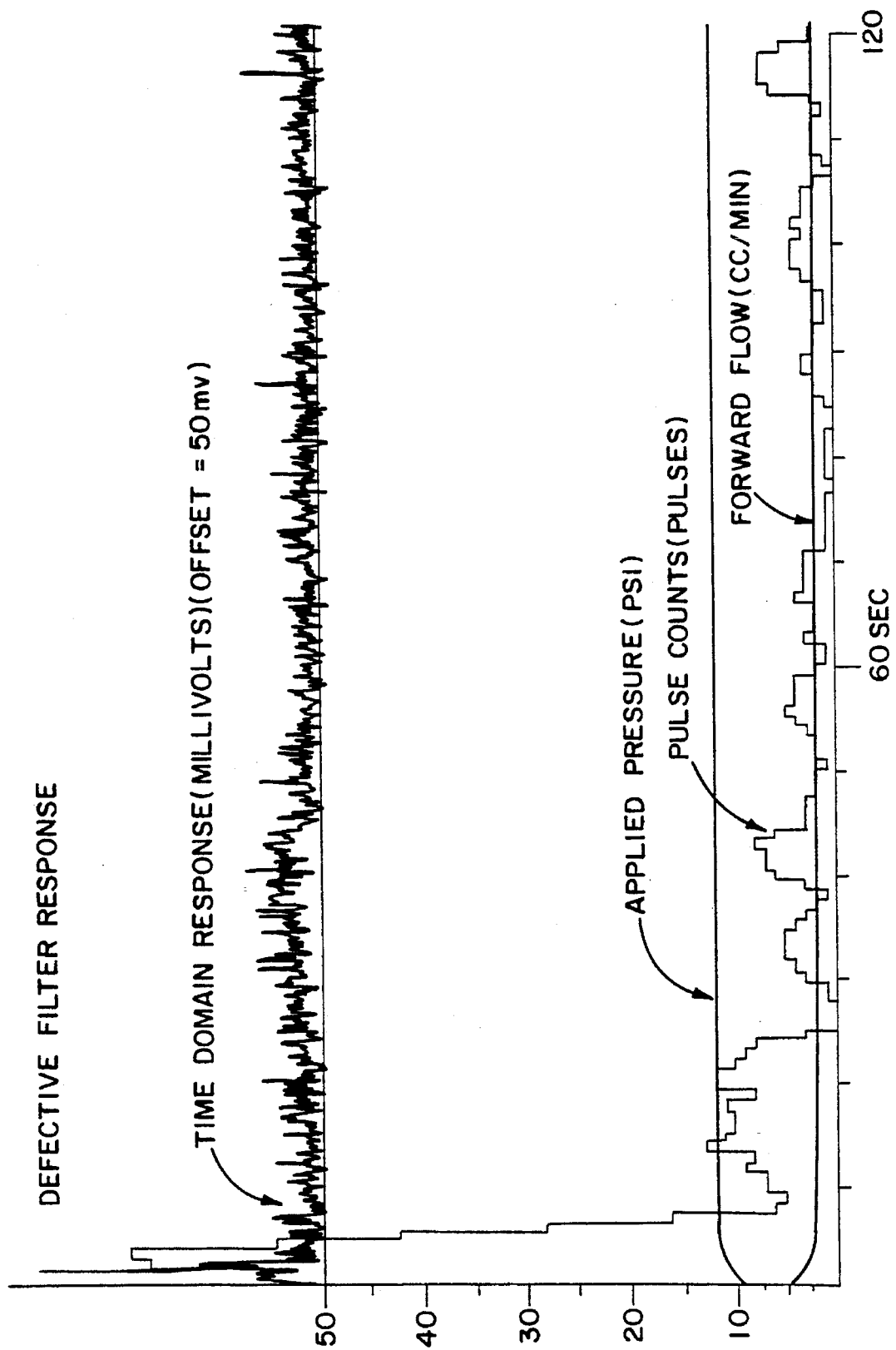
FIG. 14 is a graphical representation of a testing cycle of a defective filter according to the embodiment of the testing apparatus illustrated in FIG. 12.

Referring to FIG. 14, the microphone response of a defective filter is shown as the applied pressure is increased to a level below the specified bubble point of the filter. Various indicators can indicate that a filter is defective. The sound pressure level of the filter during the relatively stable portion of the sound pressure curve is substantially greater in amplitude, on the average, and in pulse density as compared to the sound pressure curve of FIG. 13. The defective filter can be determined from a measure of the amplitude of the pulse (peak detection), a measure of the average energy of the pulses (average energy), a measure of the pulse density, and/or by other suitable mechanisms for measuring sound signal levels and variations.

As the applied pressure reaches the bubble point, or at pressures below the bubble point for defective filters, the number of pulses per unit time (pulse density) increases and the amplitude of the pulses increases. As shown in FIGS. 9, 13, and 14, as the pulses density increases, the pulses begin to merge together. The next pulse begins before the microphone and electronic signal processing circuits have stabilized from the previous pulse. Under these circumstances, the baseline of the pulses rises. By conditioning (averaging or peak detecting) the pulses or groups of closely spaced pulses, the rise in the baseline, for example, can be detected. This information can also be utilized to discriminate between defective and non-defective filters and to determine the bubble point of a filter as described above.

Alternatively, it has been found that by counting the pulses directly, a greater level of discrimination between defective and non-defective filters can be achieved for many porous elements.

The pulse density can be measured directly by counting the number of pulses that occurred within a particular interval in time. The time intervals may be selected to be every fraction of a second, every second, every two seconds, etc. For example, the number of pulses that occurred in the 1st and 2nd seconds after stabilization could form a first pulse count, the number of pulses that occurred in the 3rd and 4th seconds after stabilization could form a second pulse count, etc.

It was found that this technique has a problem in that if a particular cluster of pulses occurs during, for example, the 2nd and 3rd second, the pulse count will be divided between two time intervals and a loss of sensitivity will result. One method of overcoming this loss of sensitivity is to utilize a sliding window technique to measure the pulses. For example, a first pulse count counts all pulses in the 1st to 5th seconds after stabilization, a second pulse count counts all pulses in the 2nd to 6th seconds after stabilization, etc. The sliding window is not limited to operation in increments of one second. Depending on the particular apparatus employed to perform the pulse counting, it is possible to determine the pulse density for any size window with any size increment. The sliding window technique may be performed so that each window has a predetermined duration, and each subsequent window overlaps a previous window by a predetermined amount. If extreme precision is required, a new window pulse count can be calculated each time that an additional pulse is received. It has been found that the use of a sliding window for measuring pulse density provides better discrimination of defective filters than the direct pulse counting per unit time. Regardless of whether the pulses are counted directly or using a sliding window, a failure is indicated if the measured count exceeds a predetermined limit. This limit may be a fixed limit or vary with increasing pressure.

The pulse counting technique may be implemented using a plurality of different apparatuses. FIG. 10 shows a first exemplary embodiment of a pulse counting apparatus. In the apparatus shown in FIG. 10, a sliding window pulse counter is implemented where each window has a duration of five times the clock period and each subsequent window overlaps the previous window by four times the clock period. For example, where a clock frequency of 1 Hz is utilized, then the apparatus shown in FIG. 10 has an individual window duration of 5 seconds and each subsequent 5 second window overlaps the previous window by 4 seconds.

An amplified signal from a microphone may be input into a smoothing circuit 58. The amplified signal, may, for example originate from the output of the variable gain amplifier 17 as shown in FIG. 3. The smoothing circuit 58 is optionally provided for smoothing the pulses to better match the response time of other components in the pulse counting circuitry 60. One example of a suitable smoothing circuit 58 is shown in FIG. 4A. The amplified signal (with or without smoothing) may be input into a first input of a comparator 61.

The second input into the comparator may be a predetermined threshold voltage $V_{Threshold2}$ or a varying threshold voltage $V_{Baseline}$ that varies with the baseline of the microphone signal received depending on the setting of a mode select switch 59. The predetermined threshold voltage $V_{Threshold2}$ provides a constant DC voltage at a predetermined level. The predetermined level may be varied to adjust the for such variables as microphone position, housing type, or the characteristics of the porous element. The varying threshold voltage $V_{Baseline}$ may, for example, originate from the conditioning circuit 18 of FIG. 3 in those embodiments where the conditioning circuit is implemented by a circuit having relatively long rise and fall times. For example, the varying threshold voltage $V_{Baseline}$ may be obtained from the conditioning circuit 18 when the conditioning circuit is implemented using the circuit shown in FIG. 4B and when the resistances R6–R8 are adjusted so that the conditioning circuit 18 tracks the baseline of the amplified signal.

The output of the comparator 61 may be input into a one-shot 62. The one-shot 62 outputs a square wave pulse responsive to pulses received from the comparator 61. The duration of the pulse output from the one-shot 62 is not critical so long as the duration of the pulse is not so long as to mask subsequent pulses. If the porous element produces pulses at a rate of, for example, 100 Hz, then the one-shot 62 is preferably set to have a pulse duration of about 1 milli-second. The output from the one-shot 62 may be input into a single counter for counting the pulses directly, or input into a plurality of counters for implementing the sliding window counting method. In a preferred embodiment of the exemplary apparatus shown in FIG. 10, the output from the one-shot 62 is input into a clock input of counters 63–67. The counters utilized in the pulse count circuitry 60 may comprise any suitable counting mechanism and include any number of counters. In the preferred embodiment, there are 5 counters (counters 63–67), each comprising 8-bit decimal counters for counting between 1 and 100. The 8-bit output from each of the counters 63–67 may be input into a bus multiplexer 72. The bus multiplexer may be implemented, for example, using a plurality of data selector circuits such as a MC14512 manufactured by Motorola. The bus multiplexer 72 may selectively output the results from 1 of the 5 counters to a latch circuit such as 8-it latch 73.

Figure 11:
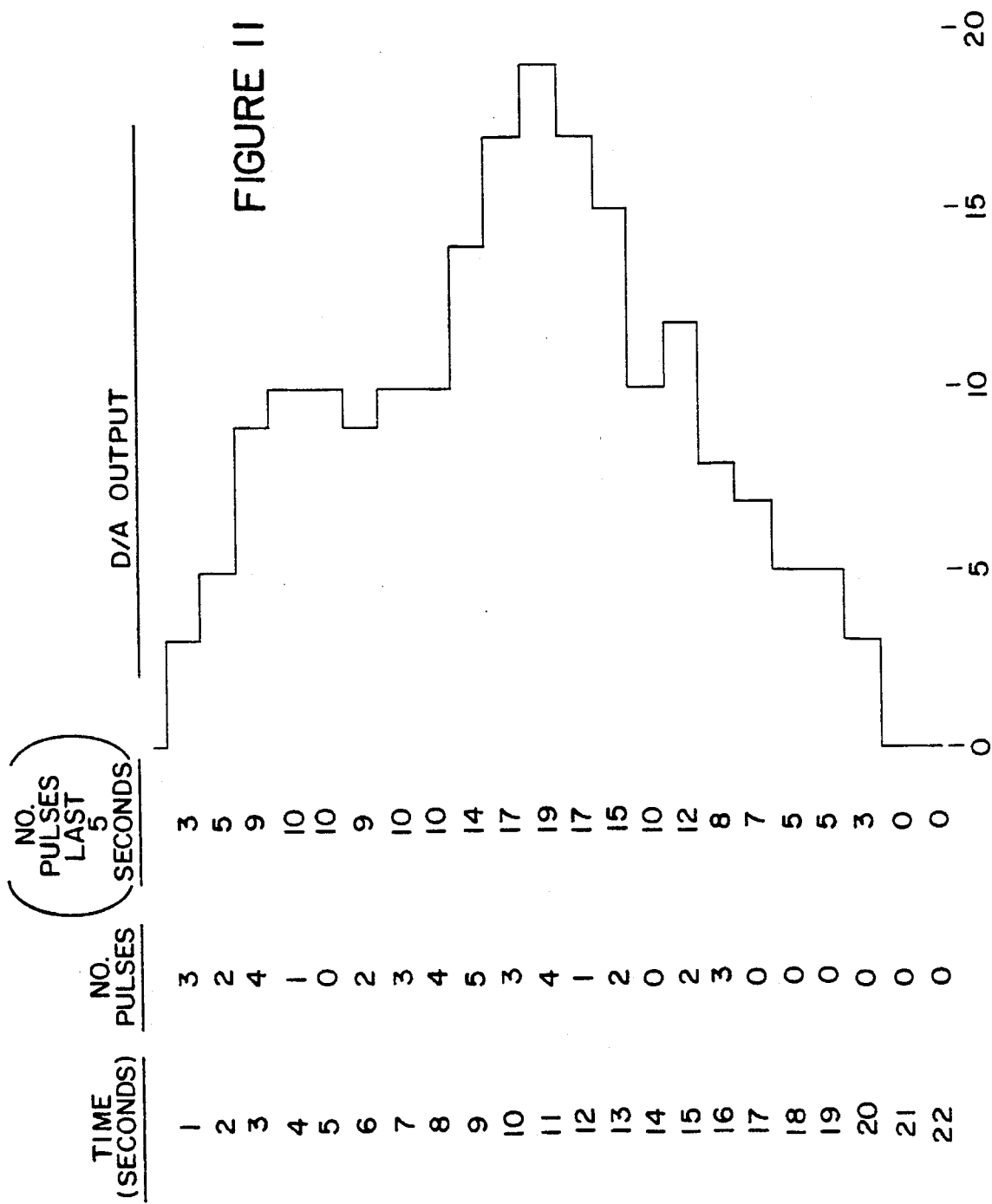
FIG. 11 is a graphical representation of a test cycle according to one configuration of the pulse count circuitry shown in FIG. 10.

The results contained in the 8-it latch 73 may be output to a plurality of output devices for analyzing the results of the test such as a display 75, a D/A converter 77, and/or a comparator 76. The display 75 may be any display capable of visually displaying the current value of the latch 73. The comparator 76 preferably receives an adjustable count limit indicative of the maximum number of pulse counts permitted for a particular porous element. It may be desirable to visually indicate a failure whenever the output from the latch 76 exceeds the count limit. Suitable logic for visually indicating that the pulse count has been exceeded may, for example, be constructed as shown in FIG. 6 with the output from the comparator input into the pulse width exceeded signal. The D/A converter 77 may be coupled to a chart recorder for producing a plot of the pulse count as shown in FIG. 11.

Timing and control for the pulse count circuitry 60 may be provided by any suitable mechanism. In the illustrated embodiment shown in FIG. 10, the timing and control is provided by a clock signal CLK input into an inverter 74, down counter 68, decoder 69, timing control NAND gates 70, and master reset NAND gates 71. The clock signal CLK may be operated at any frequency. In the preferred embodiment, the clock is operated at a frequency of 1 Hz.

In operation, the embodiment illustrated in FIG. 10 provides a sliding window pulse counter where each window has a duration of five times the clock period and each subsequent window overlaps the previous window by four times the clock period. With a 1 Hz clock, this provides a five-second window with one second increments. The apparatus counts the number of pulses in the 5-second window, and updates this count at intervals of one second. The digital display shows the count in the latest 5-second interval, and is updated every second. A failure is indicated if the measured count exceeds a preset limit. In addition, a D/A Converter provides an analog output, suitable for a strip chart recorder. This provides a permanent record, in a graphical bar chart format, of the complete test.

When the mode select switch is set to the threshold voltage $V_{Threshold2}$, pulses received which exceed the threshold voltage $V_{Threshold2}$ trigger the one-shot 62 to produce a pulse. The pulses from the one-shot 62 increment each of the counters 63–67 simultaneously. Reset inputs Reset 1–5, respectively coupled to counters 63–67, provide asynchronous resets to each of the counters so that a different counter is reset on each cycle of clock input CLK. The timing and control circuitry operates so that the rising edge of the clock input CLK controls the multiplexer 72 to select a new counter to output to the latch. The falling edge of the clock input CLK latches the current count of the selected counter into the latch and resets the selected counter. Counting in the reset counter then resumes from an initial value of zero. The down counter 68 sequentially selects each of the counters so that the counters are output and reset in the order R5, R4, R3, R2, R1, R5, ... If a 1 Hz clock is input into the input clock CLK, then each counter will be reset every 5 seconds, and a different counter is reset every second. In this manner, the sliding window described above is implemented.

A sample output from the chart recorder 78 is shown in FIG. 11 for a response to a bubble point such as the one shown in FIG. 9 for the case where the threshold voltage is set to a fixed constant. If, for example, the predetermined count limit input into the comparator 76 had been set at 16 pulses (in 5 seconds), a failure would be indicated at the 10-second point.

Referring to FIG. 9, when the voltage threshold $V_{Threshold2}$ is set to a fixed constant and the one-shot 62 is edge triggered, there will be a large number of pulses prior to reaching the bubble point and then the pulses will cease. This is illustrated, for example, in FIG. 11. Pulse counting ceases because the baseline of the signal response from the microphone exceeds the threshold voltage $V_{Threshold2}$ so that the one-shot 62 is no-longer activated (assuming a one-shot 62 that is edge triggered).

Other circuit arrangements are possible which continue to count pulses even after the bubble point is reached. For example, when the mode switch in FIG. 10 is set to the threshold voltage $V_{Baseline}$, the threshold voltage tracks the baseline. In this arrangement, pulse counting continues even after the baseline voltage increases because the threshold voltage $V_{Baseline}$ is configured to track the baseline. Other circuits can be constructed to provide similar results. For example, a circuit capable of storing the average voltage may be suitable for providing the threshold voltage $V_{Baseline}$.

Although the strip chart recorder 78 provides a useful diagnostic tool, for production testing, only a simple limit setting is required so that there is no interpretation of data by the operator. This is a significant advantage over conventional bubble point testing where operator experience and judgement was a factor in reverse bubble testing.

Figure 12:
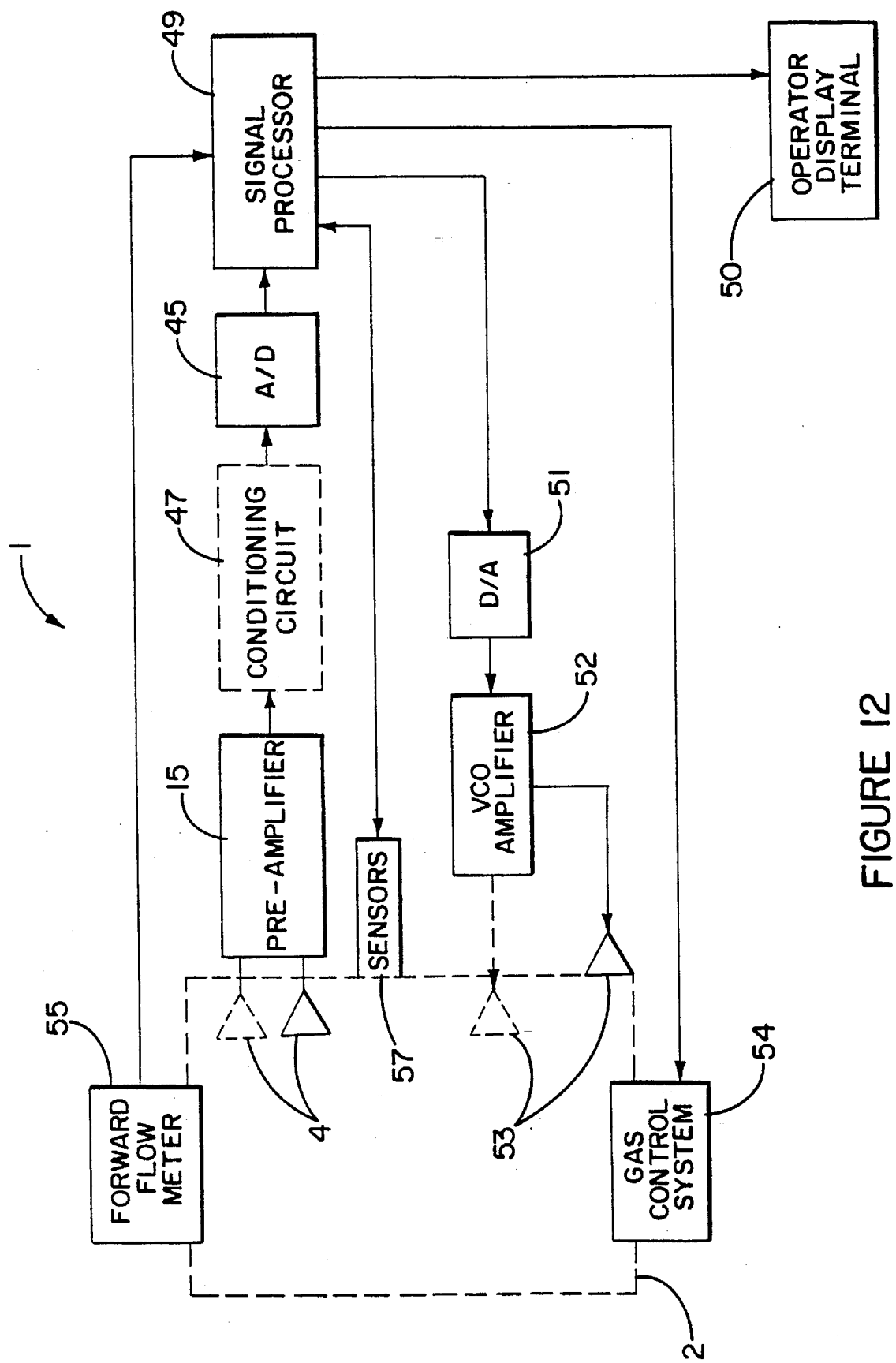
FIG. 12 is a block diagram of an alternative embodiment of the testing system shown in FIG. 1.

A fourth embodiment of the porous element testing system 1 is illustrated in FIG. 12. Components in the fourth embodiment are similar to components in the other embodiments. In the fourth embodiment, the housing 2, containing the porous element, is coupled to a forward flow meter 55, a gas control system 54, a microphone 4, a transducer 53 (coupled either to the inside or the outside of the housing 2), and sensors 57. The microphone 4 detects sound within the housing 2 and outputs a signal indicative of the sound detected.

The signal from the microphone is amplified by the preamplifier 15 which outputs a preamplified signal. The preamplifier 15 is preferably constructed as discussed above with respect to the first embodiment. Alternatively, the preamplifier 15 may be constructed using a standard ultrasonic preamplifier.

In some filtration devices, it may be preferable to include a plurality of microphones 4. The plurality of microphones may be arranged adjacent to a single porous element and coupled together to increase the signal to noise (S/N) ratio. The random noise associated with, for example, electrical noise of the electronic components will not be additive, while sound signals from the filters will be additive, thus increasing the signal to noise ratio. Any method for in-phase coupling the signals from the two microphones may be utilized as is well known in the art. For example, the signals may be added using an analog adding circuit disposed in the system either prior to or after the preamplifier 15. Alternatively, the signals from the microphone may be added digitally. In this arrangement, a plurality of microphones 4 are respectively coupled to separate channels, each channel containing a preamplifier 15 and A/D converter 45 coupled to the signal processor 49. The signal processor may then add the response of each channel digitally.

Conditioning circuit 47 may optionally be provided to provide amplification, filtering, and/or signal conditioning as discussed above relative to the other embodiments. In a preferred embodiment, filtering is provided to limit the bandwidth of the preamplified signal to, for example, the ultrasonic range prior to digital conversion by an A/D converter 45. Alternatively, the A/D converter 45 can receive the signal directly from the pre-amplifier 15. The A/D converter converts the received signal into a digital signal. The digital signal is input into a digital signal processor 49. The digital signal processor 49 may, for example, be a dedicated signal processing device or a programmable computer such that the operator display terminal 50 and the signal processor 49 are combined. In a preferred embodiment, the operator display terminal 50 and the signal processor 49 are implemented in a single programmable computer using LabVIEW For Windows software from National Instruments. FIGS. 16 and 17A–F are graphical representations of embodiments of a LabVIEW For Windows software program for controlling the signal processor 49.

The digital signal processor 49 is coupled: to the forward flow meter 55 for measuring the forward flow of a gas through the housing 2, to the gas control system 54 for controlling the pressure within the housing 2, to an operator display terminal 50 for providing control and input data, to a digital to analog (D/A) converter 51 for outputting built-in-test (BIT) signals, and to a plurality of sensors for monitoring the environment in which the test is conducted. The digital to analog converter 51 is coupled to a voltage controlled oscillator/amplifier 52, which is in turn coupled to transducers 53.

In a preferred embodiment, the transducer 53 is coupled to the outside of the housing 2. Sound imparted to the outside of the housing 2 may be detected by the microphone 4 located on the inside of the housing 2. By coupling the transducer 53 to the outside of the housing 2, the transducer 53 is insulated from the fluid processed by the porous element testing system 1. In a preferred embodiment, the transducer 53 is preferably an ultrasonic transducer and may be the same type of ultrasonic transducer utilized for the microphone 4. Alternatively, the transducer 53 may be a audio speaker, or any other mechanism for converting energy into sound. In an alternative embodiment, the transducer 53 may be coupled to the inside of the housing 2 to provide additional sensitivity for the built-in-test.

It may be possible to couple the VCO/amplifier 52 directly to the microphone 4 so that the microphone 4 serves both as a transducer and a microphone. In this manner, a pulse can be originated by the VCO/amplifier 52, converted to an ultrasonic sound wave by the microphone 4 producing an incident sound wave within the housing 2. A reflected sound wave may then be received by the microphone 4, converted into an electrical signal and received by preamplifier 15. Thus, a BIT may be conducted by a single ultrasonic transducer. However, this method is less preferred since by using a single transducer for both transmit and receive functions, the sensitivity of the transducer for receiving sound signals is reduced.

The signal processor 49 controls the A/D to initiate a built-in-test signal. The voltage controlled oscillator (VCO)/amplifier 52, may for example, be constructed using two cascaded precision wave-form function generators whose output signal is amplified. The precision wave-form generators may be constructed using standard 8038 circuit available from EXAR or Intersil. In a preferred embodiment, a first wave-form generator is set to oscillate at a relatively low frequency such as 100 Hz. The output from the first wave-form generator circuit is used to frequency modulate a second wave-form generator circuit about a fundamental frequency which is set to coincide with the resonance of the transducer 53. In this arrangement, the second wave-form generator circuit outputs a wave-form having a frequency which oscillates between a resonance and non-resonance frequencies in accordance with the output from the first wave-form generator circuit. The output from the second wave-form generator circuit is preferably amplified by an amplifier capable of driving the transducer 53. The transducer outputs a signal in accordance with the frequency of the first wave-form generator circuit.

The signal processor 49 may optionally include a plurality of sensors 57 such as temperature sensors and barometric sensors. Pressure sensors may be useful in providing greater accuracy in the flow meter. Temperature sensors are useful for on-line customer applications where the housing 2 is operated at an elevated temperature due to steam sterilization or process parameters. It is well known that the pores in a porous element may act as capillaries. The pressure required to force fluid through a capillary is related to the surface tension of the fluid in the capillary. Many liquids have a Surface tension that varies greatly with temperature. Thus, in order to ensure reliable operation in on-line testing environments having wide temperature variations, it is desirable to monitor the temperature at which the porous element is tested. The test pressure and defective filter parameters may then be adjusted to correspond to a particular surface tension of the wetting fluid.

In operation, the embodiment shown in FIG. 10 may operate to perform any of the methods and circuit functions hereinbefore discussed for other embodiments of the porous element testing system 1, either individually or in combination. Referring to FIGS. 13 and 14, the signal processor 49 operates to provide a quantitative measure of the signal produced by the sound transducer 4 in order to discriminate between defective and non-defective porous elements. Quantitative measures produced by the signal processor 49 may include:

a) detecting the minimum or maximum peaks of signals (peak detection) to provide a quantitative measure of the peaks of each of the signal pulses;

b) detecting the average signal voltage, current and/or power by any suitable averaging technique including rms, maximum or minimum pulse amplitude averaging, integration, low pass filtering, peak detection having finite rise and fall times, and/or signal averaging;

c) detecting signal density by any suitable technique including: counting pulses relative to a fixed value or a plurality of differing fixed values, variable average value (baseline), and/or previous pulse value (differential amplitude pulse counting), counting frequency shifts, and/or measuring the time between pulses; and/ or d) detecting signal variability by measuring differences in voltage, current, power, and/or frequency.

Each of the quantitative measures can be individually correlated with defective and non-defective filters, and/or processed to provide a confidence index combining a plurality of the quantitative measures. Additionally, each of these quantitative measures can be combined with forward flow measurements and other measurements of filter integrity. In this manner, filters that do not fail individual quantitative measures of integrity but have, for example, values falling at the upper range of a plurality of quantitative measures can be identified for close scrutiny. Additionally, each of the individual quantitative measures can be analyzed statistically to determine the standard deviation, variance, mean, and other statistical attributes. For example, it has been found that the standard deviation for defective porous elements may be higher than the standard deviation for non-defective porous elements.

It has been found that measuring pulses with respect to a plurality of different threshold values provides increased discrimination between defective and non-defective porous elements.

Each of the above mentioned quantitative measures can be calculated for the entire test period, for a particular portion of the test period (quantitative measure per unit time), and/or for sliding windows where each window has a fixed or variable duration and where windows may overlap previous windows by a fixed or variable amount. The windows may be determined using units of time and/or other measures derived from the signal such as pulse counts or frequency shifts.

For on-line applications, the individual performance of each filter element can be saved from each test. This data provides a history of the response of the filter element under previous tests, and alerts the operator to any substantial deviations from previous tests. If a substantial increase in, for example, the forward flow value or the pulse count value is detected, then the porous element testing apparatus 1 signals the operator that additional off-line testing may be desirable.

In one mode of operation, the embodiment of the porous element testing system 1 shown in FIG. 12 can be used as a diagnostic tool. This allows certain kinds or sizes of defects to be "finger printed" by their signal characteristics such as frequency. The term finger printed may be variously defined to include any means of comparing one pattern with another and includes such techniques as pattern recognition techniques and signature analysis techniques. The digital signal processor 49 compares the signal received from the microphone 4 with a number of finger print signatures stored in memory to identify the existence and/or type of filter defect.

Figure 8:
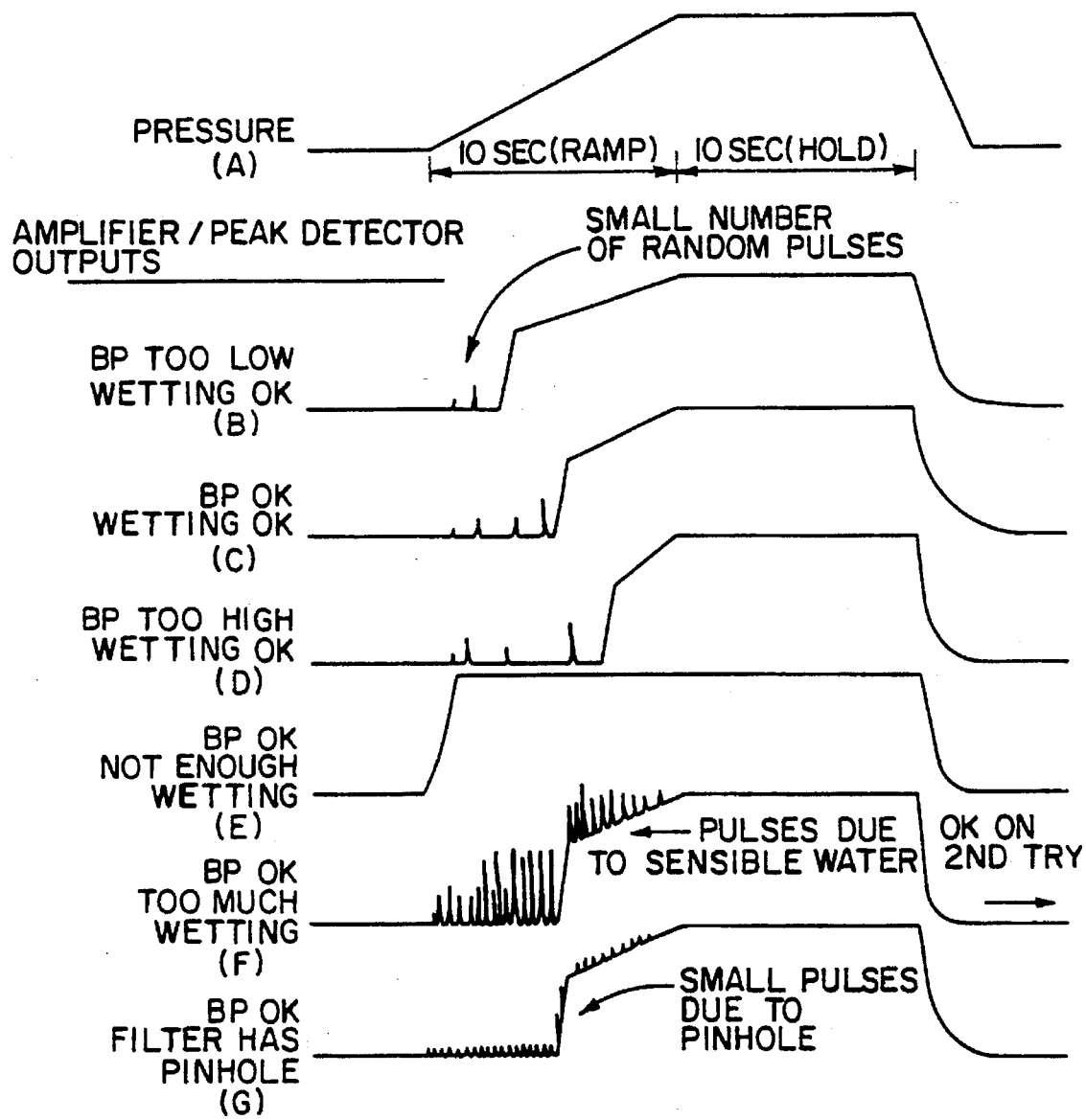
FIGS. 8A–G depict simplified graphical representations of the responses of the apparatus of FIG. 1 to various filter conditions.

Referring to FIG. 8, several examples are illustrated showing various finger prints. The finger prints illustrated in FIG. 8 represent the simplified time domain response input into the signal processing device 49 for various conditions of the porous element. FIG. 8A shows an example of a test pressurization curve having a 20 second ramp and a 10 second hold period. FIGS. 8B–8G illustrate simplified drawings of various fingerprints which result from the pressurization curve shown in FIG. 8A being applied to porous elements having various conditions. For example, FIG. 8B shows the finger print that results when the wetting solution is correctly applied, but the bubble point is too low. FIG. 8C shows the case where the wetting solution is correctly applied, and the bubble point is within a permissible range. FIG. 8D shows the finger print which results from a bubble point being too high.

FIG. 8E illustrates the case where an insufficient amount of wetting solution is applied to the porous element, even though the bubble point is within the permissible range. One problem that may be encountered when testing filters using forward flow test methods is that a false indication of a faulty filter may result from insufficient wetting of the filter. By combining forward flow tests with the porous element testing apparatus 1, an improper wetting can be detected, and an operator can be informed that the filter may have been improperly wetted. Under these circumstances, the operator can re-wet the filter and begin the test again. Depending on the degree to which the filter is improperly wetted, too little wetting may often be detected by a steeply rising baseline. For example, if a large number of pores remain unwetted, the signal response may appear as though there were a large hole in the porous element and rise steeply.

FIG. 8F shows the finger print associated with a bubble point within the permissible range, but where too much wetting solution has been applied. It has been found that is difficult to discriminate a condition of too much wetting from real failures. Therefore, once the signal processor 40 detects that too much wetting may have occurred, it is desirable to have the signal processor 40 either extend the testing time by maintaining the gas control system at the predetermined pressure, e.g., 80% of the bubble point or conduct a second test. FIG. 8F shows the finger print associated with a filter having a pin hole. A small pinhole may, for example, appear as small pulses superimposed on the correct output, assuming the porous element is good other than having a pinhole.

Some ultrafiltration porous elements have pores that are too small to be tested using bubble point techniques. This may occur when, for example, the bubble point pressure is prohibitively high because of limitations of the test apparatus. These ultrafiltration porous elements typically include a membrane and a structure, such as an end cap, mounted to the membrane. Ultrasonic testing can be used to test for defects in the membrane mounting structure, defects in mounting the membrane to the membrane mounting structure, and gross defects in the membrane. The same finger print techniques described above can be used to classify the various defects in ultrafiltration porous elements as a diagnostic mechanism.

Preferably, the digital signal processor 49 classifies the type of defect, and then displays an indication to the user on the operator display terminal 50 indicative of the type of defect detected. In this embodiment, it may be desirable for the band-pass filtering, half-wave rectification, signal integration, threshold detection, pulse width detection, stabilization time, and total test time functions to be performed by the digital signal processor 49. Each of the functions of the digital signal processor 49 are user programmable via the operator display terminal 50. This allows the functions to be tailored to a particular porous element. For example, large porous elements typically have noise spikes of a greater duration. Thus, it is particularly advantageous to be able to vary the predetermined noise limit time period.

Figure 15:
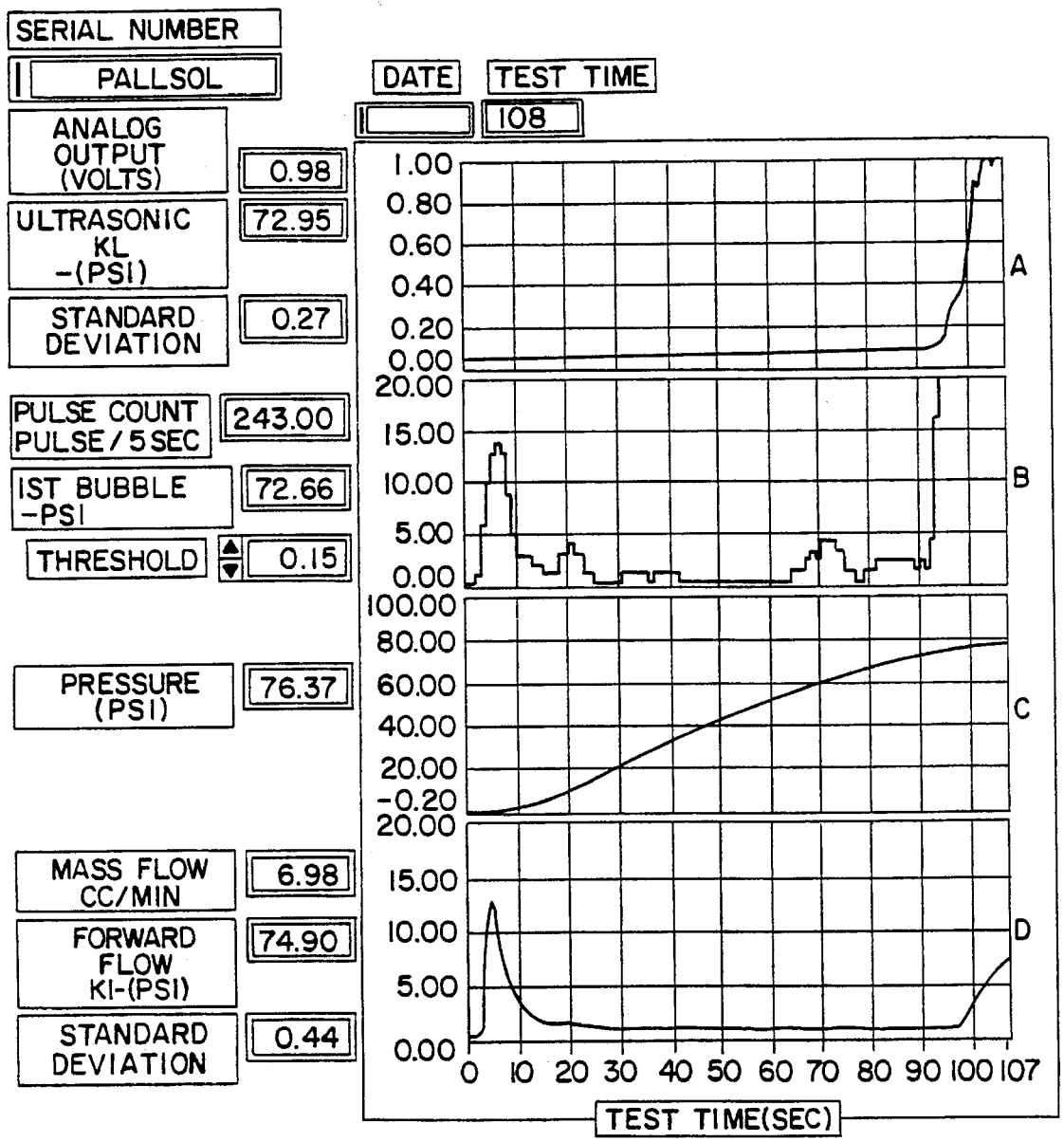
FIG. 15 is a graphical representation of a typical front panel screen displayed during a testing cycle of a filter according to the embodiment of the testing apparatus illustrated in FIG. 12.
Figure 16A:
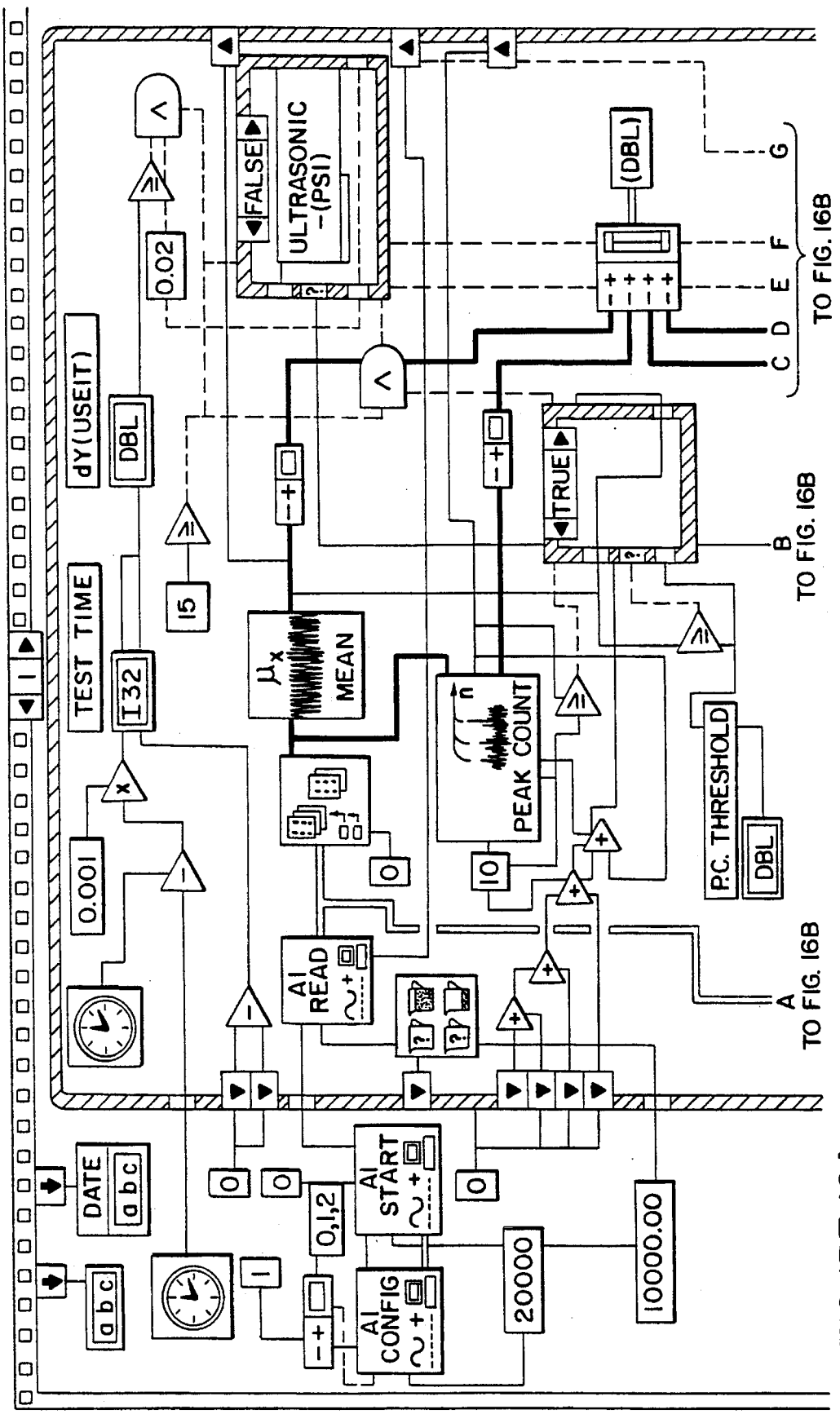
Figure 16B:
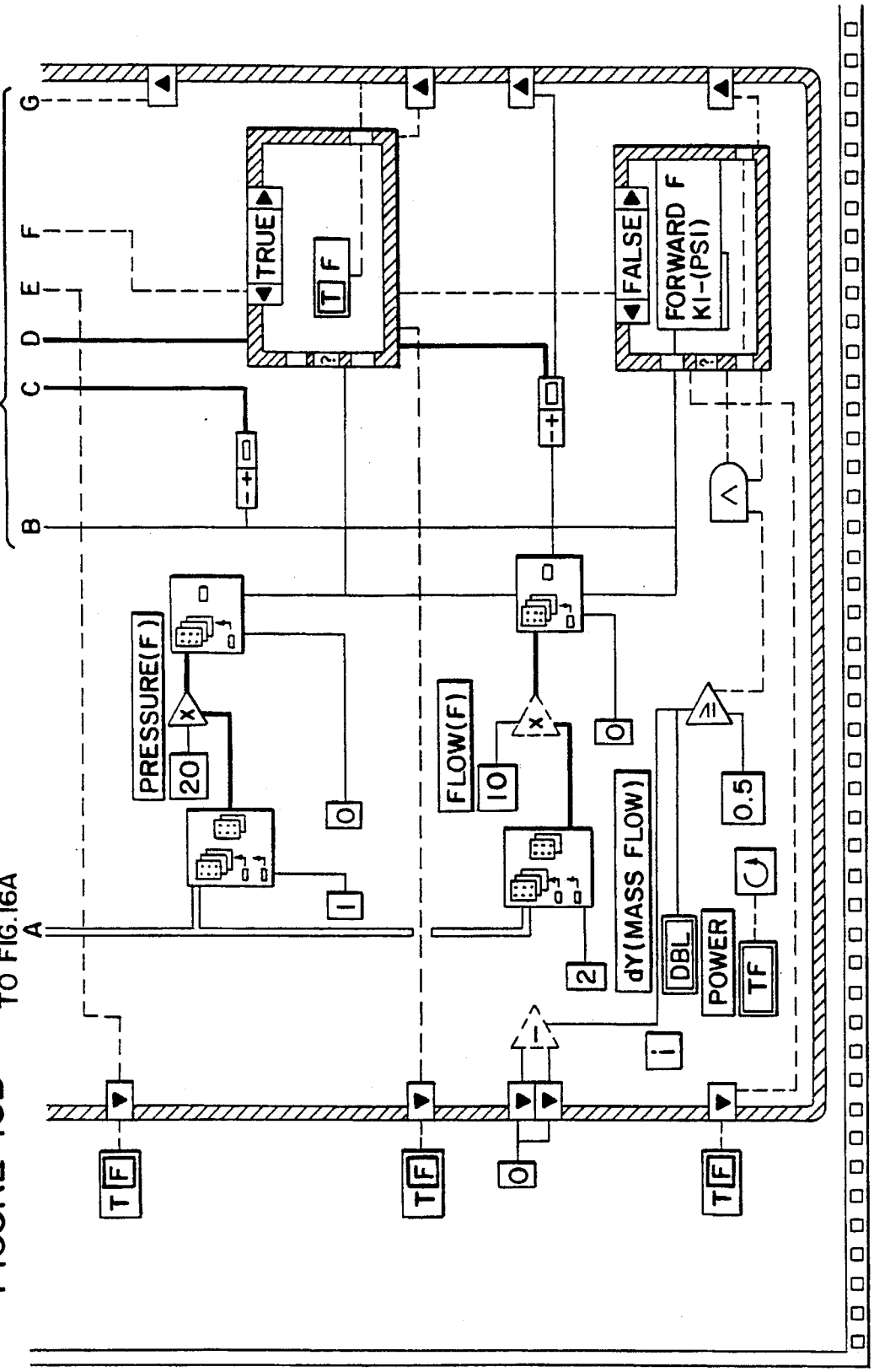
Figure 17A:
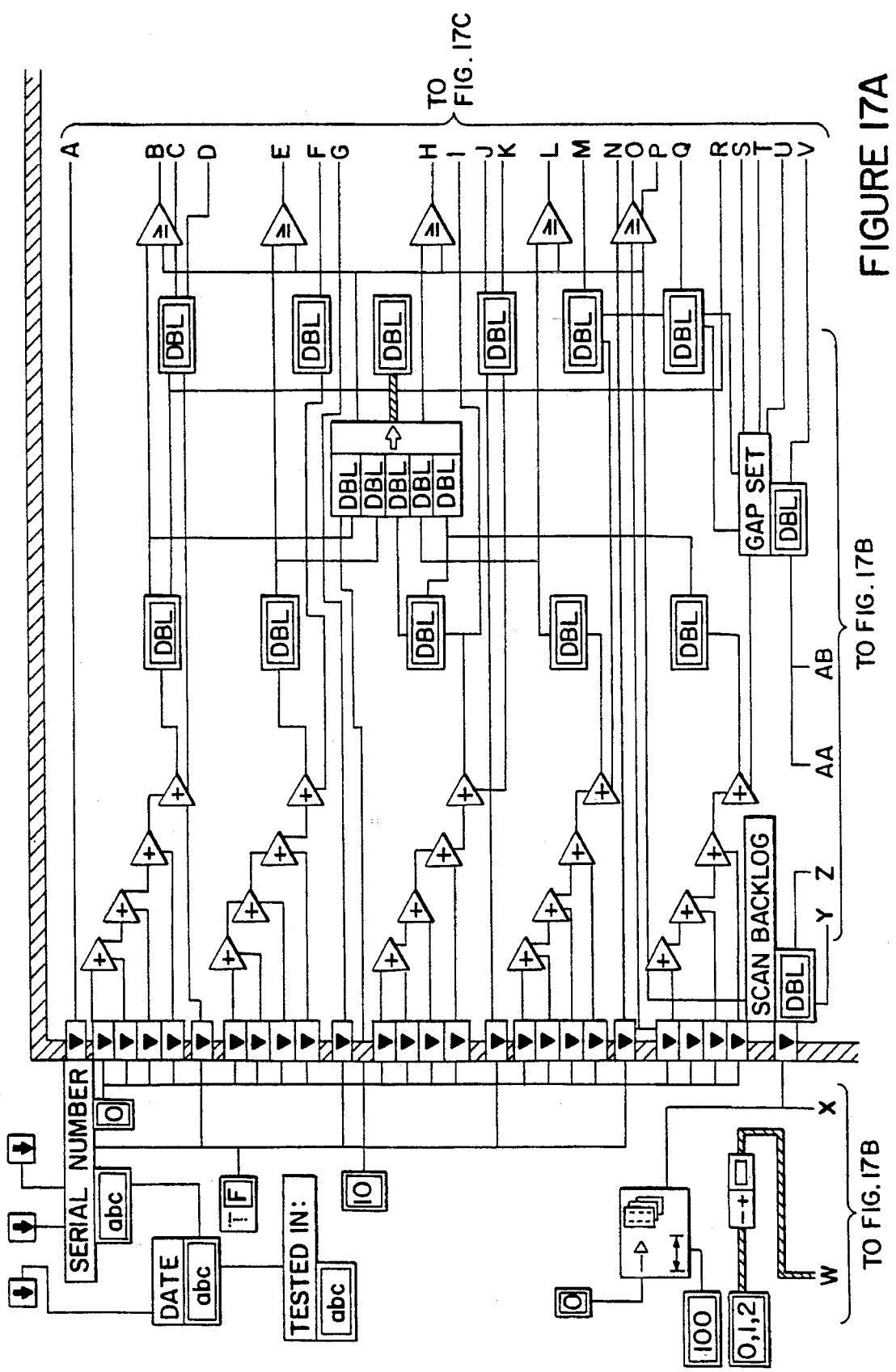
Figure 17C:
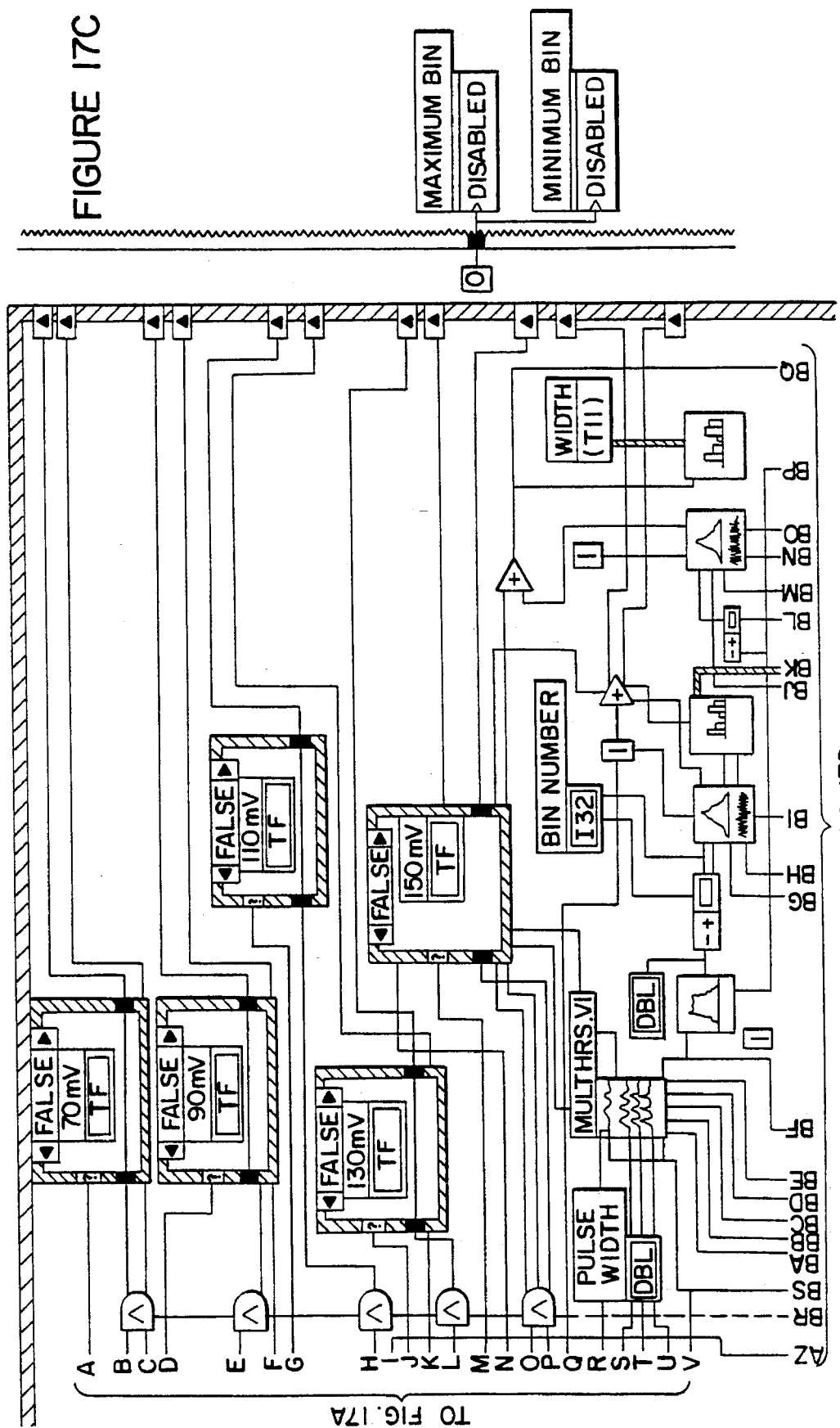
Figure 17D:
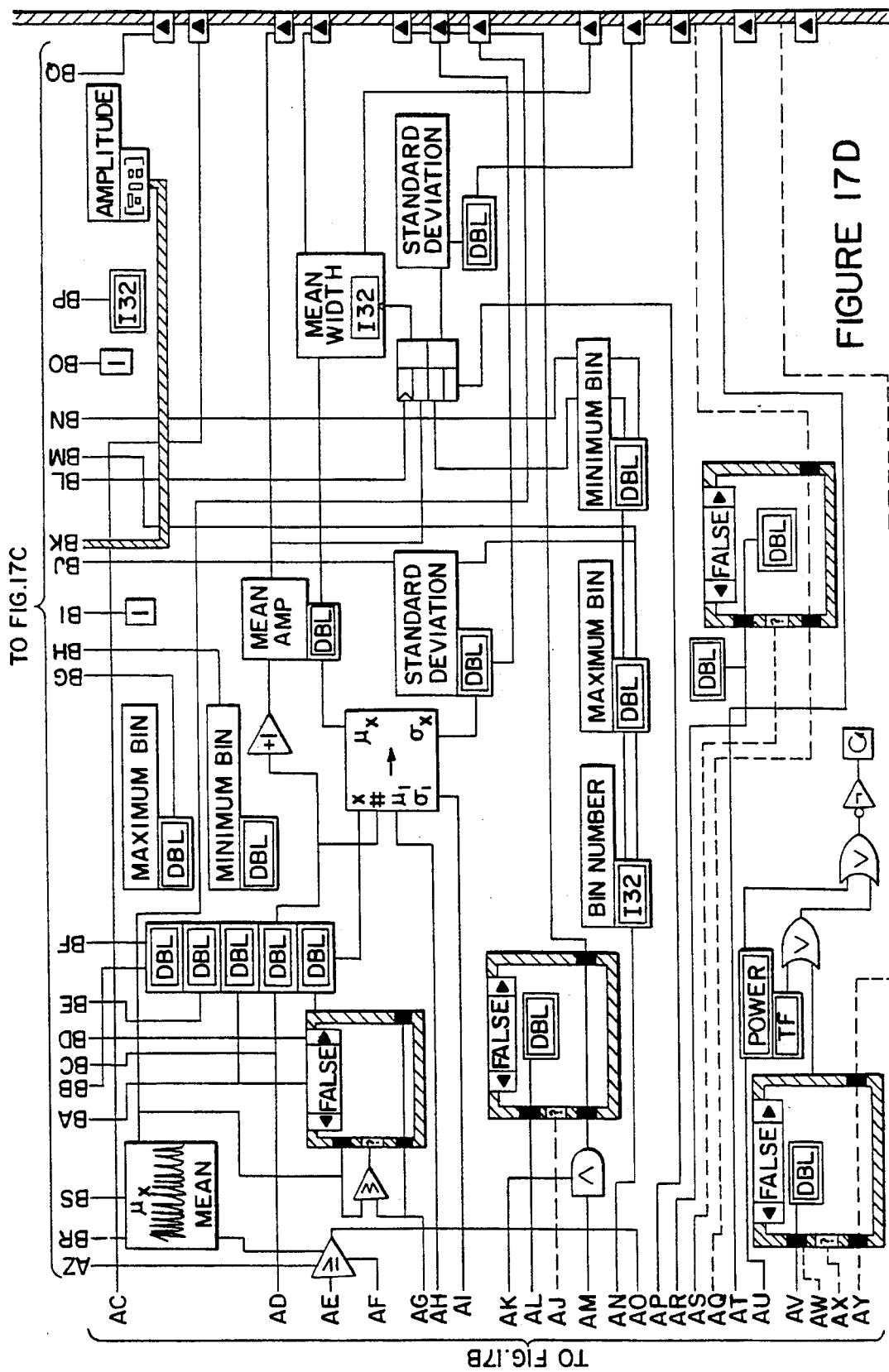
Figure 17E:
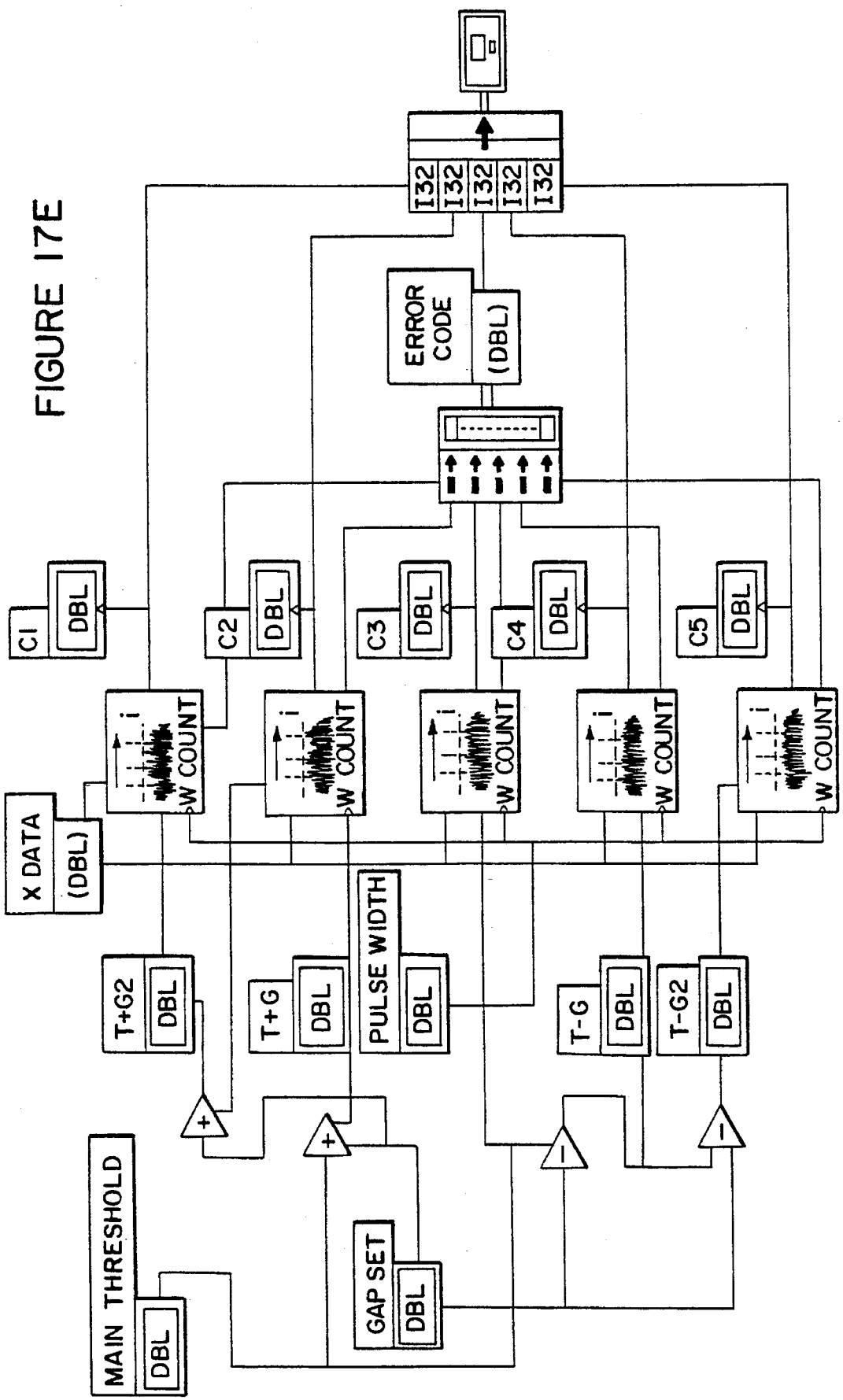
Figure 17F:
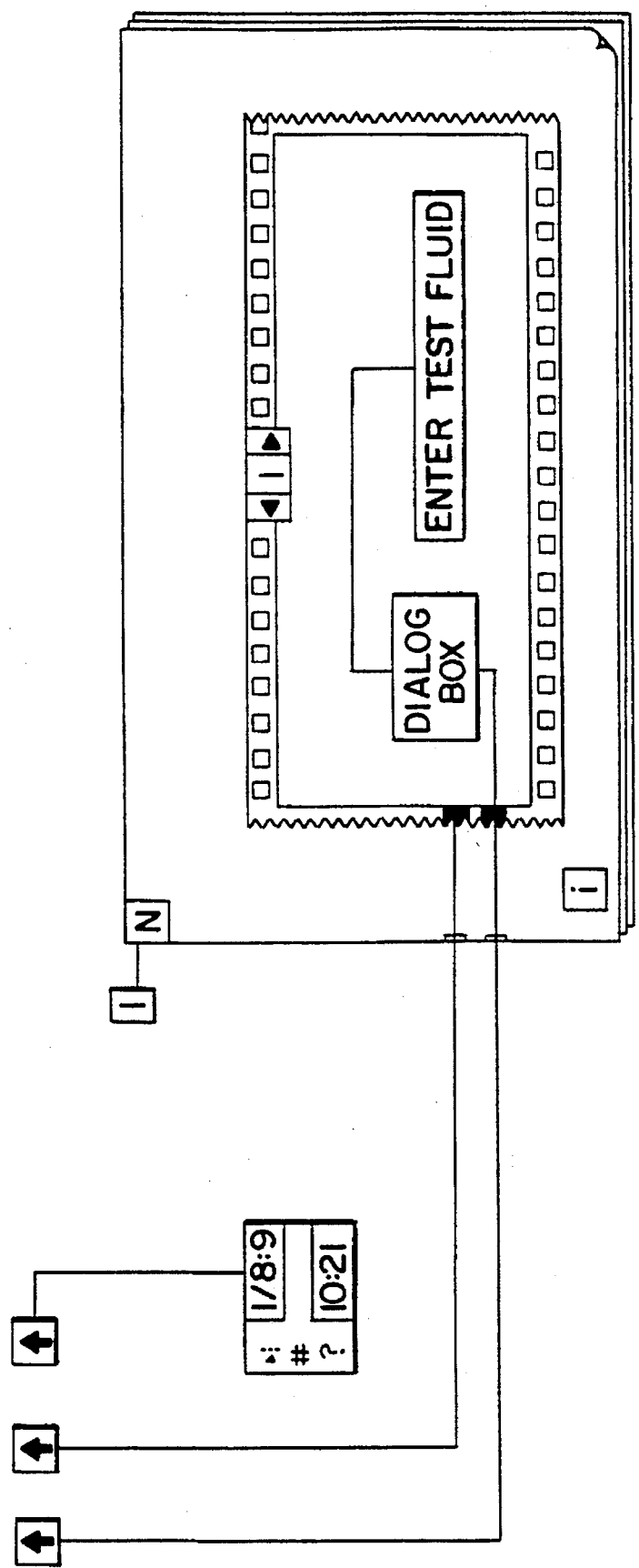

Typical outputs from the operator display terminal 50 are shown in FIGS. 13–15. FIGS. 13 and 14 are discussed above. FIG. 15A shows a graphical illustration of an average of the analog signal sampled at a rate of 20 KHz and averaged using a one second window. The left hand portion of the output screen shown in FIG. 15A displays the current analog output voltage, the bubble point $K_L$ determined from the averaged sound signal, and the standard deviation. FIG. 15B displays a graphical representation of the pulse count, the 1st bubble point (as determined by the pulse count), the current pulse count, the standard deviation, and the pulse count error threshold for the particular filter element under test. FIG. 15C shows the pressure applied to the porous element under test. FIG. 15D displays a graphical representation of the mass flow, the current mass flow, the bubble point $K_L$ as determined from mass flow, and the standard deviation of the mass flow.

The digital signal processor 49 may also be programmed so that it can dynamically set the adjustable bandpass filter's characteristics, variable gain characteristics, pressure level, microphone position selected, total test time, stabilization time, low pass filter parameters, noise limit time and threshold value in response to a code input by the user and indicative of the type of porous element being tested, the type of wetting solution applied to the filter, etc. It should also be noted that the functions of the circuitry illustrated in FIG. 3 may be performed directly by the signal processor 49.

When used in conjunction with a forward flow test meter 55, the signal processor is capable of inputting information received from the forward flow test and displaying this information on the display terminal 50. Ultrasonic testing is particularly advantageous for detecting some types of defects such as defects in extremely thin membrane filters that rely on pore size as the filtration mechanism and not on membrane thickness. Additionally, ultrasonic testing is compatible with simultaneous forward flow tests, and with reverse flow testing the porous element. When testing the porous element in the reverse direction, both a gas control system 54 and a forward flow meter 55 can be provided on both sides of housing 2.

It has been found that defects in porous elements occur over a particular pressure range. Thus, in a preferred embodiment, it is desirable to slowly ramp the pressure while monitoring the acoustic output from the porous element to increase discrimination between defective and non-defective porous elements. Alternatively, the applied pressure may be stepped in discrete increments to provide increased discrimination and detect defects which occur only at particular pressures.

The digital signal processor 49 also preferably stores a series of test calibration patterns that are associated with certain types of porous element defects to test and calibrate the porous element testing system. These calibration patterns are utilized to test the microphone 4 and other circuitry to ensure operability and to provide a fail-safe fault detection mechanism that can be actuated, for example, before and after each test sequence.

In operation, the signal processor 49 outputs a digital test signal to the digital to analog converter 51. The digital to analog converter 51 converts the digital calibration signal to an analog calibration signal. The analog calibration signal may, for example, be converted into a signal for driving the transducer 53 by VCO/amplifier 52. Transducer 53 converts the test signal into sound pressure levels within the housing 2. These sound pressure levels are received via microphone 4 and input into digital signal processor 49 via pre-amplifier 15, conditioning circuit 47 and analog to digital converter 48. The signal processor 49 can compare the received test signal with the calibration signal sent and thereby verify the operation of the porous element testing system 1.

The operator display terminal 50 may optionally contain a data base program which automatically receives test data from a particular manufacturing lot of porous elements. In this manner, it can be determined whether an entire lot is within manufacturing specifications when a predetermined percentage of the porous elements under test fail to pass. The operator display terminal 50 may also be utilized by an operator to grade a particular lot of porous elements so as to certify its applicability to a particular type of application based quantitative measurements and the average failure rate of the manufacturing lot.

In certain applications, a plurality of filter devices are tested in parallel. This may occur, for example, in a distillation application where a requirement for a low pressure drop across the filter elements dictates that an extremely large number of filter elements be coupled in parallel. Under these circumstances, it may be difficult to adequately test these filters using forward flow, and further it may be difficult or impossible to isolate a particular faulty filter element from the plurality of filter elements. Using the present test method, it may be possible to include a different microphone in close proximity to each filter element, or group of filter elements. The sound signal from a particular microphone can then be utilized to isolate the failure to a single filter or group of filters.

Exemplary Methods For Evaluating Porous Elements

A plurality of methods and systems have been developed for collecting and analyzing data generated by the porous element testing system 1 to discriminate between defective and non-defective filters. Some of these discrimination methods and systems have already been discussed. For example, the circuit in FIGS. 3 and 10 may discriminate between defective and non-defective filters by a) operator observations of a filtered and conditioned signal on a chart recorder, b) detecting when a conditioned signal has exceeded a predetermined threshold for a predetermined period of time, and/or c) counting the number of pulses that exceed a threshold during a predetermined time period or a plurality of time periods which may or may not overlap. The porous element testing system 1 collects data, analyzes or summarizes the data, and presents the data to an operator. In some embodiments, the porous element testing system 1 may process the data to determine whether the filter is defective. In the case of a chart recorder, the interpretation of the data is performed manually by the operator.

Figure 23:
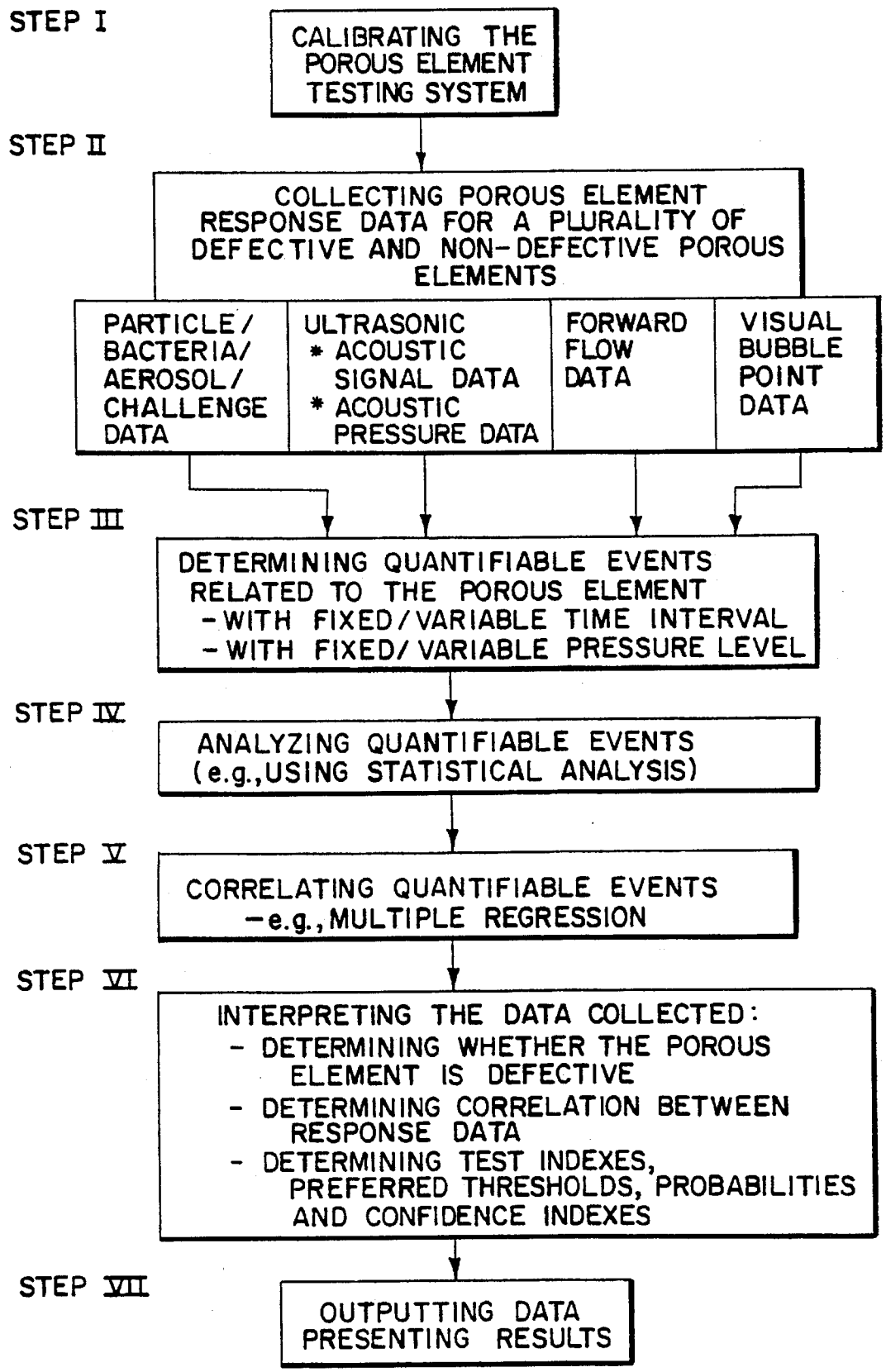
FIG. 23 is a flow chart of an exemplary method of operating the porous element testing system.

The porous element testing system 1 may perform any of the methods and circuit functions hereinbefore discussed either individually or in combination. Further, in operation, the porous element testing system 1 may I) perform an initial calibration, II) collect data representative of physical conditions in and around the porous element, III) quantify characteristics of the data collected, IV) analyze and summarize the data collected, V) determine correlations between the data, VI) interpret the data to render a determination of whether the porous element under test is suitable for a particular application, i.e., is non-defective, and/or VII) output the data in a comprehensible and understandable format. An exemplary flow chart of one method of operating the porous element testing system 1 is shown in FIG. 23. The flow chart in FIG. 23 may be variously arranged. Steps may be omitted in whole or in part, added, or rearranged.

For example, FIGS. 24 and 25 show exemplary test sequences for determining whether a porous element is defective. In FIG. 24, steps I, III, and V have been omitted, and steps II, IV, VI, and VII are partially omitted. FIG. 24 shows one method of employing only a single test parameter from the porous element testing system 1 to determine whether a porous element is defective. In FIG. 25, steps I, IV, and V have been omitted, and steps II, III, VI, and VII are partially omitted. FIGS. 24 and 25 show methods employing only a single test parameter from the porous element testing system 1 to determine whether a porous element is defective. Of course, many other permutations are possible. The exemplary steps outlined in FIG. 23 are discussed in detail below.

Step I: System Calibration

In the embodiments shown, it may be desirable to calibrate the porous element testing system to optimize the system for operation with various porous elements, housing configurations, differential pressure levels, wetting solutions, microphone positions, temperatures, background noise levels, and other environmental factors. For example, large porous elements such as, for example, large flat sheets of porous media tested on a manufacturing line, typically have noise spikes of a greater size and duration. Additionally, various housings, porous elements, microphones and microphone positions may require system calibration for consistent results.

In each of the functions and components of the porous element testing system are user programmable using an operator interface such a the operator display terminal 50. For example, it may be desirable allow the system to dynamically adjust the characteristics of the band-pass filter, half-wave rectification, low-pass filter, signal integration, threshold detection, pulse width detection, stabilization time, noise limit time period, variable gain characteristics, pressure level, microphone position selected, and total test time functions to be performed by the digital signal processor 49. Additionally, each of these parameters may be adjusted individually by an operator. The digital signal processor 49 may also be programmed so that it can dynamically adjust these parameters in response to a calibration input. In a preferred embodiment, the parameters may be adjusted by the digital signal processor 49 in response to a code, such as a serial number and/or test stand identification code, and the code may be input by the user and indicative of the type of porous element being tested, the type of wetting solution applied to the filter, etc.

The digital signal processor 49 also preferably stores or has access to a series of test calibration patterns that are associated with certain types of porous element defects. These calibration patterns may be utilized to test and calibrate the porous element testing system 1 to ensure operability and to provide a fail-safe fault detection mechanism. A calibration operation may, for example, be actuated before and after each test sequence.

Figure 18:
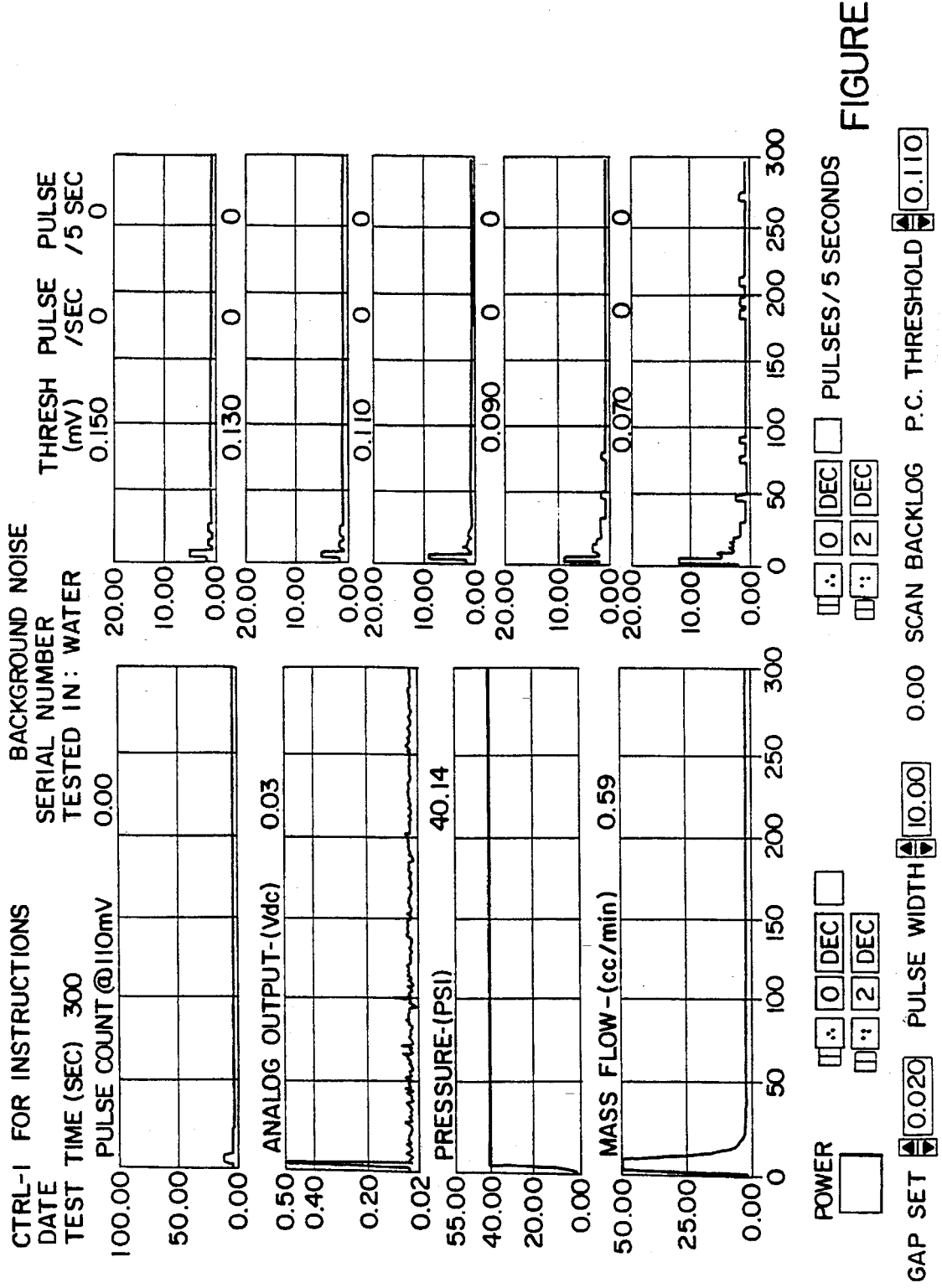
FIG. 18 is a graphical representation of a typical front panel screen displayed during a background noise calibration cycle according to the embodiment of the testing apparatus illustrated in FIG. 12.

In some embodiments, it may be preferable to determine background noise by sampling the system noise without any pressurization, or at a low pressurization such as, for example, up to about 70 percent of the bubble point pressure. The background noise can be obtained by monitoring the system parameters with and/or without a filter. A background noise measure allows the system to determine whether there is an anomaly that has caused the system to function improperly, or whether the system requires re-calibration. For example, if the noise signal consistently exceeds a predetermined threshold, then the operator may be notified that it is likely that a re-calibration operation should be performed or that extraneous noise causes should be isolated. Additionally, the background noise level may be utilized in the data quantifying, analyzing, and interpreting steps. FIG. 18 shows a exemplary front panel screen showing the background noise level.

Step II: Data Collection

In some embodiments, a plurality of different transducers are included for measuring various system parameters around the porous element such as differential pressures, temperatures, forward flow rates, acoustic energy, and other environmental conditions. The output of each of these transducers may be sampled and converted into digital values. The samples may be taken at any point in the test, e.g., at the beginning and end of the test, or continuously throughout the test. Data collection may, for example, be performed by a the signal processor 49 monitoring system parameters including signals received from microphone 4, sensors 57, and forward flow meter 55. The system parameters may be sampled and converted into a number of discrete acoustic data samples. For example, one or more A/D converters may be utilized to convert the system parameters into a plurality of digital values by sampling the sensors, microphones, and other signals indicative of system parameters at a plurality of discrete intervals.

The rate at which the system parameters are sampled may for example, range from a sample every few seconds up to millions of samples per second. In preferred embodiments, the sampling rate may vary between 5 KHz and 100 KHz, or preferably between 10 KHz and 70 KHz, or more preferably the sampling rate may be about 20 KHz. The frequency of the sampling rate is limited by various system constraints including the ability of the signal processor 49 to analyze the digital data effectively. The sampling rate may be variously configured in accordance with the system parameter being sampled. For example, the forward flow rate may be sampled at a relatively slow rate (e.g., 5 Hz) while the acoustic energy may be sampled at a higher rate (e.g., 20 KHz).

The precision of each of the digital samples may vary in accordance with the precision of the sampling system and with the system parameter being sampled. In preferred embodiments, one or more A/D converters are utilized to sample system parameters. In typical embodiments, binary digits or bits are utilized to represent each of the discrete values. The number of binary digits used to represent each of the sampled system parameters typically ranges between 8 and 24 bits.

In some embodiments, it may be preferable to condition an analog signal before sampling by the system. Conditioning of the analog signal may include, for example, a preamplifier 15 and/or a conditioning circuit 47. Additionally, other types of conditioning may occur after sampling by utilizing digital filter algorithms.

In one embodiment, each of the digital A/D values is identified with a time interval in which the digital values were sampled. For example, each digital sample may be stored in sequential order in memory. Accordingly, the storage location of the data, the sampling rate, and the precision of each sample may be utilized by the porous element testing system 1 to determine the value of the system parameters for any given time interval after initiation of the testing sequence. Thus, both the value of the system parameters and the time at which the values occurred may be stored by the signal processor 49.

The forward flow rates and differential pressures are preferably sampled throughout the test, stored in time order, and correlated with the digital values responsive to the acoustic signal. In this manner, for any given sampling period during the porous element test cycle, the signal processor 49 can determine the differential pressure, the mass flow rate, the acoustic sound level, the temperature, and other environmental factors. To facilitate identification of the particular time interval within the signal processor 49, the digital sample values may be stored in sequential order in memory so that the value of all the system parameters for any given time interval may be determined. When a plurality of microphones are utilized, digital samples may be collected simultaneously for each microphone.

Step III: Quantifying System Response Data

Once collected as outlined above, the system response data may be analyzed in accordance with a number of methods. In the simplest configuration, system response data may be collected and displayed for analysis by an operator in, for example, a chart recorder format. However, operator analysis of the data is difficult, requires highly trained and experienced operators, and is subject to operator error. Additionally, in many cases, it may be impossible for even an experienced operator to visually distinguish between good and defective filters without the assistance of quantitative measures. Accordingly, methods and apparatuses have been developed to quantify and analyze the data collected to provide quantitative measures of the system response. These quantitative measures may be easily presented to the operator and interpreted to draw inferences concerning the integrity of the porous element under test.

Figure 26:
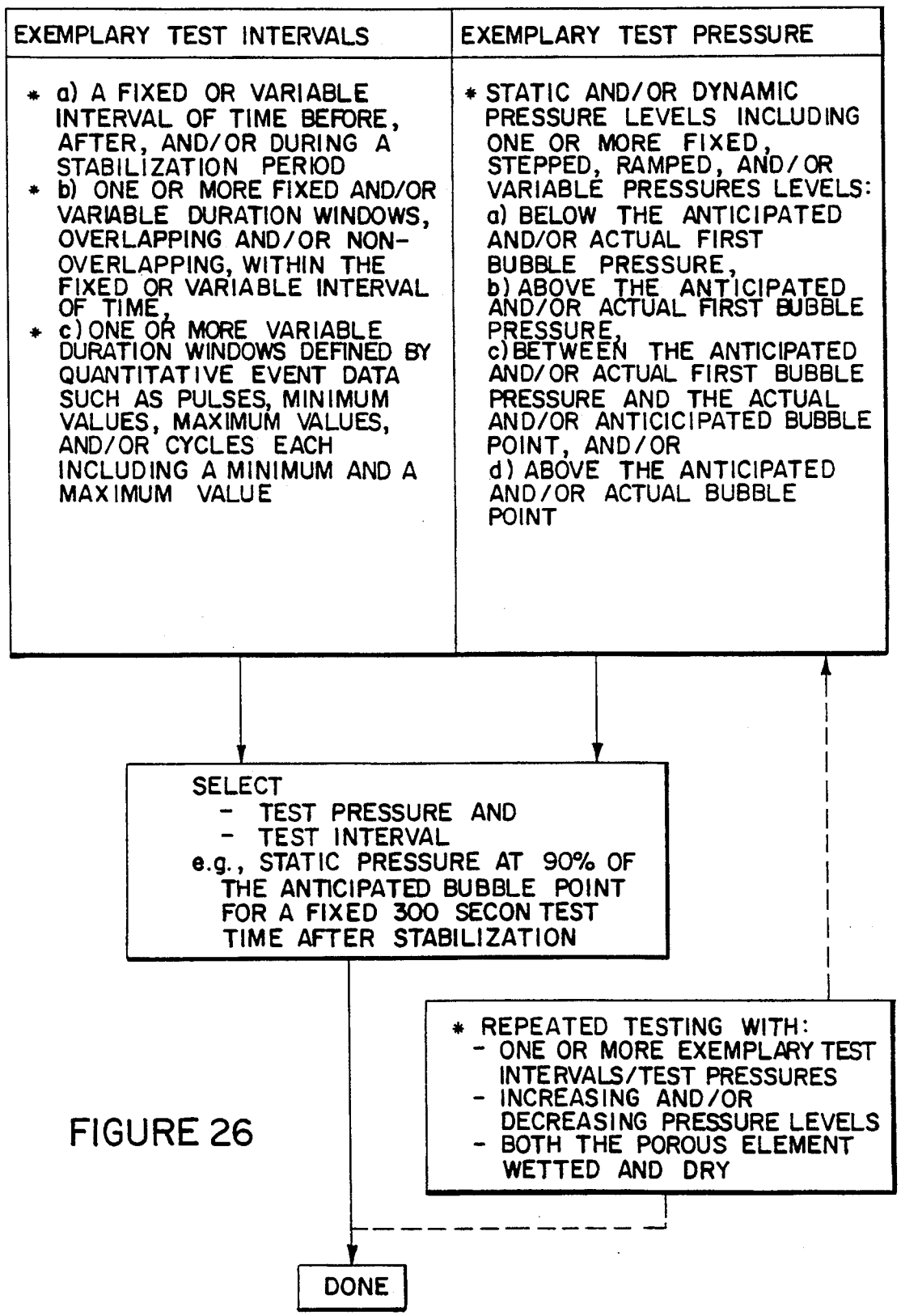
FIG. 26 is flow chart for selecting quantitative and/or statistical measures for one or more test intervals using under either a static or a dynamic differential pressure.

Referring to FIG. 26, each of the quantitative and/or statistical measures can be determined for one or more test intervals using either a static or dynamic pressure. Exemplary test intervals may, for example, include:

a) a fixed or variable interval of time before, after, and/or during a stabilization period, b) one or more fixed or sliding windows within a fixed or variable interval of time, c) one or more variable duration windows defined by pulses, minimum values, and/or maximum values, and/or d) one or more variable duration windows defined by cycles, each including a minimum and maximum value. Typical test intervals include fixed and/or variable time intervals, an entire predetermined test period, a particular portion of the test period (e.g., measures of system parameters within a window of time), and/or sliding windows where each window has a fixed or variable duration and where windows may overlap previous windows by a fixed or variable amount. The windows may be determined using units of time and/or other measures derived from the signal such as pulse counts, minimum values, and/or maximum values. It may be desirable to determine the time interval after which stabilization occurs and to only monitor system response data after a stabilization period. Limiting the analysis to an appropriate time interval prevents the data from being skewed by the strong response generated by the porous element during, for example, stabilization.

Each of the quantitative and/or statistical measures may also be determined at static and/or dynamic pressure levels. Exemplary static and/or dynamic pressure levels may, for example, include a fixed, stepped, ramped, and/or variable pressure established at one or more pressure levels:

a) below the anticipated and/or actual first bubble pressure, b) above the anticipated and/or actual first bubble pressure, c) between anticipated and/or actual first bubble pressure and the actual and/or anticipated bubble point, and/or d) above the anticipated and/or actual bubble point.

In exemplary embodiments, the differential pressure applied to the porous element may be steadily increased (i.e., ramped upward) until the first bubble is detected or until the bubble point is reached. It may be desirable to determine the first bubble and the bubble point pressure. Additionally, it may be desirable to separate the quantitative system response data from different pressure intervals so that the data is not skewed by, for example, the strong response which occurs at the bubble point.

In other embodiments, it may be desirable to sharply increase the differential pressure continuously or in a stepwise fashion to a predetermined pressure and then maintain the predetermined pressure throughout the test. If a static pressure is utilized, the static pressure is preferably below the anticipated first bubble pressure and/or bubble point. If the static pressure is below the anticipated bubble point, the static pressure is preferably between 30 and 95%, and more preferably between 50 and 90%, and even more preferably between 70 and 85%, and most preferably about 80% of the anticipated bubble point.

Further, tests on the porous element may be repeated with either static and/or dynamic pressure levels, with multiple pressure levels, with increasing and/or decreasing pressure levels, with different time intervals and/or with the porous element both wet and dry. For example, the use of wet and dry test cycles may provide a measure of pore size distributions. Additionally, for on-line applications, the individual performance of each filter element can be saved from each test. This data provides a history of the response of the filter element under previous tests and alerts the operator to any substantial deviations from previous tests. For example, if a substantial increase in, e.g., the forward flow value or the pulse count value is detected, then the porous element testing apparatus 1 signals the operator that additional off-line testing may be desirable.

Exemplary quantitative measures of system response data are outlined below.

A) Quantifying Acoustic Signal Data

Referring to FIGS. 13 and 14, the signal processor 49 may quantify various acoustic signal characteristics which may be useful in discriminating between defective and non-defective porous elements. Measures of acoustic data may be performed on both wetted porous elements and dry porous elements. In some preferred embodiments the acoustic data acquisition is performed on wetted porous elements. Exemplary Acoustic signal characteristics are outlined below.

a) Acoustic Sample Data In Time Sequential Order

One acoustic signal characteristic is the sampled time domain response of the microphone 4 defined by each of the discrete A/D sample values. For a large number of A/D samples, additional computational analysis may be performed on the A/D samples to enable interpretation of the results. In exemplary embodiments, each of the A/D values may be analyzed using various statistical measures including averages, dispersions, and distributions.

b) Identifiable Acoustic Signal Features

In some embodiments, it may be desirable to identify various acoustic signal features such as minimum voltage values, peak voltage values, and acoustic pulses.

Minimum voltage values in the acoustic signal data may be variously defined. In one exemplary embodiment, minimum voltage values are defined as those A/D output values in which both the N previous and M subsequent A/D output values are greater than the minimum voltage value, where N and M are integers. In a simplified version, N and M may be defined as 1. In this manner, minimum voltage values are defined as those samples having a preceding and succeeding sample of a greater amplitude. Alternatively, a minimum voltage value may be defined as the smallest voltage value that occurred over a defined interval.

As with minimum voltage values, peak or maximum voltage values may also be variously defined. In exemplary embodiments, peak voltage values may be defined as those A/D output values in which both the N previous and M subsequent A/D output values are less than the peak voltage value, where N and M are integers. In a simplified version, N and M may be defined as 1. In this manner, peak voltage values may be defined as those samples having a preceding and succeeding sample of a smaller amplitude. Alternatively, a peak voltage value may be defined as the largest voltage value that occurred over a defined interval.

For example, it may be desirable to only register those voltage values having voltages above and/or below a fixed or variable threshold. The defined interval may be either a fixed or variable interval including one or more windows. A filter and/or smoothing algorithm may optionally be included to filter-out various voltage values (e.g., noise spikes) by employing a digital or analog filtering or smoothing function. Exemplary filtering algorithms which may be employed include Butterworth, Chebyshev, Chebyshev II, Inverse Chebyshev, Elliptic, Cauer, and/or Bessel filters. Exemplary smoothing functions which may be employed include Hanning, Hamming, Triangular, Blackman, Exact Blackman, Blackman-Harris, Kaiser-Bessel, Flat Top, General Cosine, Cosine Tapered, Force, and/or Exponential Windows.

Acoustic pulses may also be variously defined. In exemplary embodiments, acoustic pulse may be defined as the acoustic signals occurring between successive minimum or peak voltage values, acoustic signals which exceed one or more fixed or variable threshold values, and/or acoustic signals which exceed one or more fixed or variable threshold values for one or more predetermined periods of time. In one preferred embodiment, acoustic pulses are defined as those signals which exceed a fixed or variable threshold value for a predetermined period of time. Defining acoustic pulses in accordance with the preferred embodiment provides an inherent filtering mechanism which may have a tendency to remove or filter low amplitude and/or short duration acoustic energy spikes such as those attributable to noise.

Acoustic pulses may be defined using either a single threshold or multiple amplitude and width thresholds. For example, a first set of acoustic pulses can be defined as those pulses exceeding 100 mV, a second set of acoustic pulses can be defined as those pulses exceeding 120 mv, etc. Similarly, multiple pulse width thresholds can be defined. For example, a first set of acoustic pulses may be defined as those pulses exceeding 100 mv for 50 ms, a second set of pulses can be defined as those pulses exceeding 100 mv for 70 ms, etc. Additionally, pulses may be defined using a hysteresis where the predetermined threshold on the rising edge of the pulse differs from the voltage threshold on the falling edge of the pulse. Various features of acoustic pulses or spikes may be determined such as a) the undershoot under, for example, an average minimum or baseline minimum value, b) the overshoot over, for example, an average peak value, and c) the time delay before, for example, 50% of the pulse peak is reached.

The acoustic signal features may be classified in other ways such as by identifying an acoustic signal oscillation cycle. Each oscillation cycle may be variously defined. In exemplary embodiments, an oscillation cycle may include a peak voltage value and a minimum voltage value.

c) Acoustic Energy Variations

It may be desirable to determine the extent of voltage variations produced by the acoustic signal as an approximation of the acoustic energy variations produced in the vicinity of the porous element. Exemplary variations which may be desirable to identify include the amount of change in the acoustic signal 1) between a minimum voltage value and the next successive peak voltage value, 2) between a peak voltage value and the next successive minimum voltage value, 3) between a peak and/or minimum voltage value and a fixed or variable threshold, a baseline voltage, background noise level, and/or average voltage, 5) between successive peak voltage values, 6) between successive minimum voltage values, and/or 7) between two or more successive A/D sample values including A/D sample values within a fixed or variable window. It may also be desirable to identify signal variations over any suitable fixed or variable interval using, for example, various statistical techniques such as standard deviation, variance, total variance above or below a fixed or variable value, a background noise value, a variable baseline value, and/or an average value.

d) Rate of Change Of Acoustic Energy

The rate at which the acoustic signal changes may be variously identified and quantified. For example, the average slope of the rising edge of each voltage pulse or spike may be defined by the amount the peak voltage value exceeds the immediately preceding minimum voltage value, divided by the time interval between the peak voltage value and the immediately preceding minimum voltage value. Similarly, the average slope of the falling edge of each voltage pulse or spike may be defined by subtracting the peak voltage value from the next minimum voltage value and dividing by the time interval between the minimum voltage value and the preceding peak voltage value. In some embodiments, it may be desirable to determine the average rise/fall time between two or more arbitrary points along the edge of the pulse. For example, a commonly defined value is the slew rate which is the ratio between (90% amplitude–10% amplitude) and the time interval between these two values.

The instantaneous rate of change of, for example, each successive A/D sample, may be defined by the voltage change between successive A/D samples divided by the time interval between the samples. The instantaneous rate of change values may be utilized to quantify the amount of change in, for example, the acoustic noise signal over a particular interval or between individual samples. Additionally, the total or average of the magnitudes of all rates of change may be determined for any suitable interval including over a pulse, a fixed window, and/or a variable window. Alternatively, a differentiator circuit or algorithm may be included to provide a measure of the instantaneous rate of change of the signal.

The rate of change of the time domain response is related to the various frequency domain components of the acoustic signal. In some embodiments, it may be desirable to transform the acoustic signal to the frequency domain using well known transformations. Exemplary transformations include Fourier transforms, Fast Fourier Transforms, and Discrete Fourier Transforms. The Fourier transforms may be useful in determining a power spectrum.

Other transforms, such as Hilbert Transforms and/or Fast Hilbert Transforms, may also be utilized. The Hilbert transforms may be useful detecting echos within the porous element test system 1.

An important interval may be the time period after the first bubble is reached. If the bubble point is not reached for a substantial period of time after reaching the first bubble pressure, a defective and/or non-homogeneous pore structure or a pin hole defect may be indicated. Thus, the rate of increase and/or variability after the first bubble pressure and before the bubble point is a desirable quantitative measure. Another important interval may be the time period after the bubble point is reached. As the pressure increases above the bubble point pressure, the liquid is forced from more and more pores, resulting in an increased acoustic energy. Accordingly, measuring the rate of change after the bubble point is an desirable quantitative measure. A measure of the rate of change of the acoustic energy may be obtained by quantifying the shape of the knee of the curve of the acoustic energy signal by, for example, determining the radius of the bend in the acoustic energy signal after the first bubble point is reached. As substantially all of the wetting solution is forced from the porous element, the rate of change in the acoustic energy may stabilize and approximate the acoustic energy generated by a dry porous element. The pressure at which the acoustic energy from a wetted filter approximates the acoustic energy from a non-wetted filter may be an important quantitative measure.

f) Total/Average Acoustic Energy Generated Over An Interval

It may be desirable to obtain a measure of the total acoustic energy generated over a various intervals such as, for example, each acoustic pulse, or during a fixed or variable window. One technique developed to provide a measure of the total acoustic energy is to sum or average all A/D sample values over the interval. Alternative measures of acoustic energy include multiplying the average and/or total voltage of the successive A/D samples by the time period of the interval selected. In some embodiments, an integrator circuit or algorithm may be utilized to provide a measure of the total acoustic energy that occurred over a particular interval.

In addition to the total acoustic energy, it may be desirable to measure the average acoustic energy over a given interval. Average acoustic energy may be measured by any suitable averaging or trend fitting techniques including RMS, arithmetic mean, least squares, etc.

e) Frequency/Duration of Identifiable Acoustic Signal Features

The rate at which the certain identifiable acoustic events occur and/or the time between acoustic events may be of interest. For example, it may be desirable to identify the time between successive peak voltages, the time between successive minimum voltages, the time between a minimum voltage and a successive peak voltage, the time between a peak voltage value and the next minimum voltage, the width of an acoustic pulse, and/or the time between A/D sample values which exceed a one or more predetermined thresholds. The width or duration of an acoustic pulse may be determined at one or more arbitrary values such as, for example, at 80% of the pulse peak or at a fixed value such as 100 mV.

Similarly, it may be desirable to determine the rate of occurrence of pulses, minimums, maximums, pulses over a predetermined threshold, pulses over a predetermined threshold for a predetermined period of time, rates of change over a predetermined level, pulses defining a area over a predetermined level, and/or rates of occurrence of other identifiable events.

In preferred embodiments, the rate of occurrence of pulses are determined for a plurality of windows within a fixed or variable interval. One preferred embodiment measures the number of pulses that occur in sliding windows having a duration of 5 seconds.

In some embodiments, it may be desirable to view the acoustic energy generated by both defective and non-defective filters as being formed by a plurality of spikes or pulses. Each pulse or spike may have one or more minimum values and a peak value. For example, the quantitative acoustic signal characteristics defined above may be applied to an interval defined as each pulse.

Figure 27:
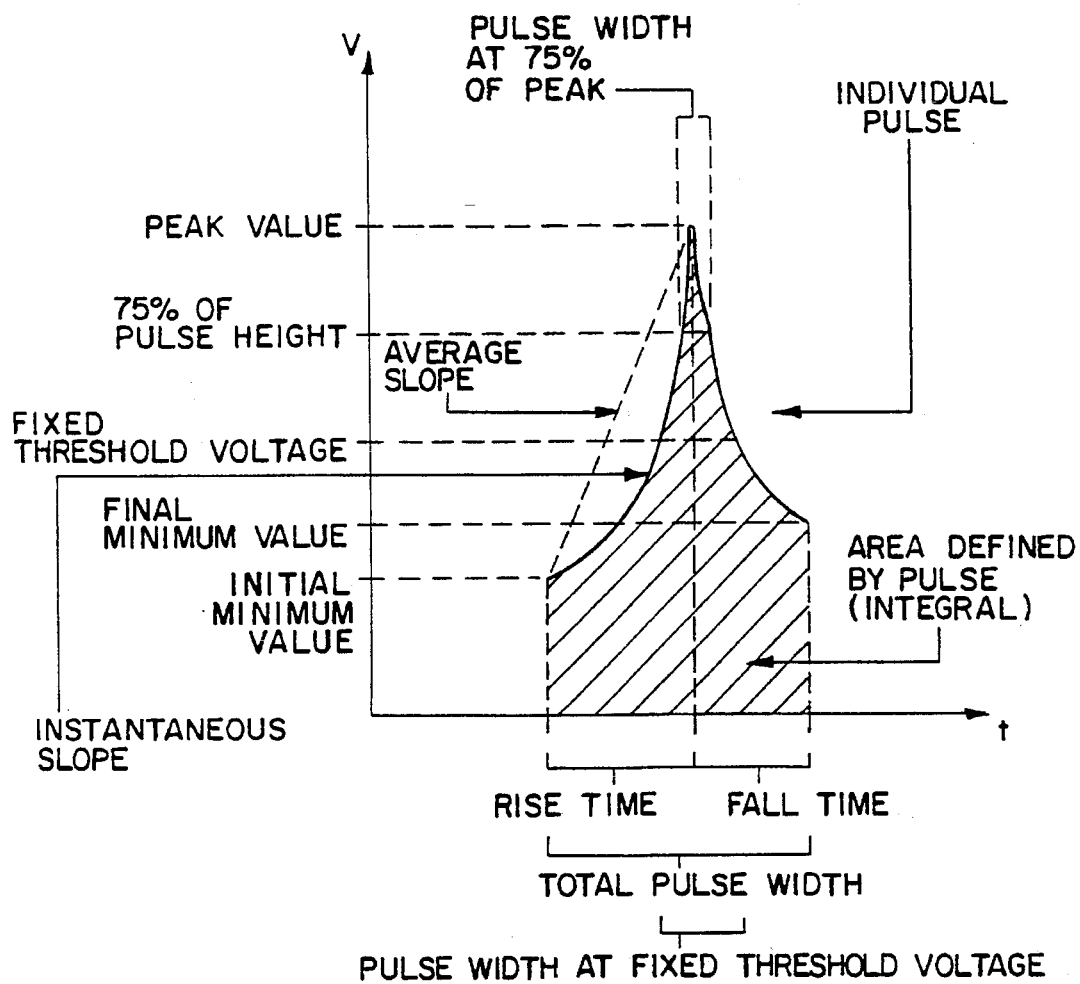
FIG. 27 is a diagram of various parameters which may be utilized to characterize an acoustic pulse or spike.

Referring to FIG. 27, an acoustic pulse or spike may be variously defined. For example, each spike or pulse has an initial minimum value or starting value, rises rapidly to a peak value, and then falls rapidly back to a final minimum value or ending value. The final minimum value may differ from the initial starting value. The width of each pulse may be measured in seconds, or any arbitrary unit such as the number of A/D samples per pulse.

It may be desirable to process or filter the acoustic signal to simplify the analysis. For example, digital or analog filters may be implemented to, for example, smooth the output. Additionally, each spike may be defined using a hysteresis (or Schmitt trigger) so that a peak must exceed the initial minimum value by a predetermined amount before a pulse is registered. Additionally, it may be desirable to have the final minimum value be less than the peak value by a predetermined amount before a final minimum value is established. The use of a hysteresis or filter may optionally be employed to simplify the characterization of acoustic pulses.

Each pulse can be characterized by a plurality of different measures. For example, an initial minimum value, final minimum value, peak value, and width of each spike may be recorded. Other measures may also include: determining the amount the peak voltage of each spike exceeds a minimum voltage value or a baseline voltage determined using any suitable averaging technique; determining an integral of each spike or a plurality of successive spikes (e.g., the area under each spike); determining an amount by which each spike differs from a baseline voltage or average voltage; determining a width between peaks of successive spikes or between initial/final minimum values of each spike; determining a width of each spike at arbitrary values along the pulse such as, for example, at 80% of the pulse peak;

determining a width of each spike at a predetermined threshold voltage value; determining rise and fall times of each spike; and/or determining an instantaneous or average slope of the rising and/or falling edge of each spike. Some of the quantitative measures which may be used to characterize acoustic pulses are outlined in FIG. 28.

B) Quantitative Acoustic Pressure Data

The acoustic energy generated by the porous element in conjunction with a variable pressure may be utilized to determine the differential pressure at which the ultrasonic first bubble and the ultrasonic bubble point occur.

a) Ultrasonic First Bubble Pressure

The differential pressure at which the wetting solution is forced out of the largest pore or defect in a wetted porous element may be considered to be the first bubble pressure. For homogeneous, non-defective membranes, the first bubble pressure may be relatively easy to detect and appears as an acoustic sound pressure which suddenly increases either continuously or discontinuously. However, for pin-hole defects, the signal produced by the first bubble may be difficult to discriminate from ambient noise. The first bubble pressure of a small pin hole defect may occur at pressures far below the bubble point pressure. Pin hole defects typically result in an ultrasonic signal that has only slightly greater variations in the acoustic signal than would be attributable to noise produced by a non-defective filter. Thus, application of the quantitative analysis techniques described herein are particularly useful for discriminating between defective filters having pin-hole defects and non-defective filters. In a preferred embodiment, the porous element testing system 1 provides a measure of the first bubble pressure by identifying the pressure at which a pulse count exceeds a predetermined limit. Alternatively, the first bubble may be variously identified. For example, the first bubble pressure may be defined as an acoustic signal having an amplitude, rate of change, minimum voltage, peak voltage, acoustic pulse, acoustic energy variation, total/average acoustic energy and/or frequency/duration which exceeds one or more fixed or variable thresholds.

It has been found that the ultrasonic first bubble pressure (even for pin-hole defects) correlates well with manually performed visual reverse bubble tests.

b) Ultrasonic $K_L$

A differential pressure at which the gas is able to force the wetting solution from a plurality of the largest pores in a relatively homogeneous pore structure may be defined as the bubble point. A common measure of the bubble point, is the quantity "$K_L$". In a preferred embodiment, the porous element testing system 1 provides a measure of the bubble point pressure $K_L$ by identifying the pressure at which an acoustic sound pressure suddenly increases either continuously or discontinuously. The ultrasonic bubble point or $K_L$ may be variously defined. In a preferred embodiment, the ultrasonic $K_L$ is defined by the intersection of a line drawn along the slop of an arithmetic average of two successive large blocks of A/D acoustic data samples. For example, when the system detects a sudden increase either continuously or discontinuously, a first group of consecutive A/D samples (e.g. 5000) are averaged with a succeeding second group of consecutive A/D samples (e.g., 5000). The average value of the second group of samples is subtracted from the average value of the first group of samples and divided by the time between the medium sample of the first group and the medium sample of the second group. In exemplary embodiments, the ultrasonic $K_L$ may be determined when the average of the first group of A/D samples exceeds the average of a second group of samples by a predetermined threshold.

Alternatively, the ultrasonic bubble point may be variously defined. For example, the ultrasonic bubble point may be defined as an acoustic signal having an amplitude, rate of change, minimum voltage, peak voltage, acoustic pulse, acoustic energy variation, total/average acoustic energy and/or frequency/duration which exceeds one or more fixed or variable thresholds, or more preferably which exceeds a fixed or variable threshold for a predetermined period of time. In one exemplary embodiment, the ultrasonic $K_L$ is determined to be the point where the pulse counts established using a plurality of variable thresholds (e.g., variable thresholds dynamically adjusted in accordance with an increasing baseline) converge to substantially a single value or a relatively narrow range of values.

C) Quantifying Measures of Flow Data

The forward flow test quantitatively measures the sum of diffusive flow and flow through any pores larger than a predetermined size. In forward flow testing, a differential pressure is created across a wetted porous element. At low pressures with a non-defective filter, the differential pressure is unable to force the liquid from the pores of the filter, so that only diffusive gas flows through the filter. At lower pressures, the flow per unit of applied pressure remains substantially constant and is an important quantitative measure of forward flow.

At a certain higher pressure, known as the forward flow first bubble point, the measurable gas flow through the filter begins to rise rapidly. The pressure at which the first bubble is reached provides one indicator of the maximum pore size of the filter. As the pressure increases above the first bubble, more and more of the liquid is forced from the pores of the filter and the flow of gas through the filter increases. The slope of the curve after reaching the first bubble may provide one quantitative measure of the uniformity of the pore sizes in the filter element. Further, a relative measure of the pore size distribution may be obtained by quantifying the shape of the knee of the curve of the forward flow curve by, for example, determining the radius of the bend in the forward flow curve.

The quantity $K_L$ is commonly used as a measure of the bubble point. The traditional $K_L$ point indicates the pressure at which the mass flow curve in a forward flow test bends and may be determined by the intersection of the lines drawn along the slope of the forward flow curve before and after reaching the $K_L$ point. Other important forward flow quantitative measures may be derived from a wet/dry curve analysis as is well known in the art. For example, the dry flow, maximum pore size, minimum pore size, mean pore size, cumulative flow, and differential flow may be derived from the quantitative measures of flow data.

D) Quantifying Visual Bubble Point Data

A reverse bubble test (sometimes referred to as a first bubble test) detects defects by looking for bubbles while a wetted filter is submersed in a liquid. With the filter wetted and liquid covering one side of the filter, a gas at constant and/or variable pressure is directed against the other side of the filter. At a certain pressure known as the first bubble pressure, the gas is just able to force the liquid from some of the largest pores. Bubbles formed in the liquid are detected. For small pin-hole defects, the bubbles usually must be detected manually since bubbles created by diffusive flow can often mask the bubbles produced by small pin-hole defects. To distinguish between bubbles from diffusive flow and bubbles due to pin-hole defects, the porous element may have to be probed by the observer.

E) Quantifying Destructive Challenge Data

Destructive challenge tests may be used to determine measures of filter integrity by challenging the filter with a large number of extremely small objects and determining the number of objects which are passed through the filter. In some challenge tests, the objects may be in the range of a few nano meters. Destructive challenge tests are well known and include particle challenge, bacteria challenge, and aerosol challenge tests. Destructive challenge tests provide a highly reliable method of discriminating between defective and non-defective filters. Additionally, the degree of defectiveness may be proportional to the number of objects that pass through the filter. Destructive challenge tests have the obvious disadvantage of being destructive. Once tested, the filter cannot be reused. However, the results of destructive tests may be correlated with quantitative system response data from non-destructive tests (e.g., quantitative acoustic signal data and quantitative acoustic flow data).

Step IV: Analyzing System Response Data

Various statistical analysis techniques may be employed to develop quantitative measures of a filter response which can then be utilized to draw inferences about the physical properties of a filter. Statistical analysis techniques may be applied to summarize and analyze the quantitative system response data. Exemplary statistical analysis techniques are described below.

a) Frequency Distribution

A frequency distribution may be constructed which records the number of events which fall within a description of a particular class. The data collected by the systems and methods defined herein may be grouped into different classes. Events or data which fall within a particular class may be variously defined. The number of classes in the frequency distribution may vary and the ranges associated with each class may be of equal or unequal size.

For example, a separate class may be defined for each value produced by the A/D converter. Alternatively, each class may be defined as a range of values. In the case where a large number of samples are obtained, such as in the sampling of acoustic data, the data may be grouped into a few classes having a wide range.

For maximum precision, it may be desirable to define the range of each class very narrowly. For example, if an 8-bit A/D converter is used, then 256 classes may be defined respectively corresponding to the 256 discrete values produced by the A/D converter. In this manner, each class would include a range covering only a single value. The signal processor may implement this classification system by recording the number of samples which have the same discrete A/D output value.

A simplified frequency distribution chart may, for example, contain only two ranges. If the data being analyzed is acoustic data, a first class may be defined as those acoustic signals less than a predetermined threshold value and a second class could be defined as those acoustic signals greater than or equal to the predetermined threshold value. In this example, the frequency distribution could be utilized to compare the number of samples in which the acoustic signal exceeded a predetermined threshold value with the number of samples in which the acoustic signal did not exceed the threshold value.

In preferred embodiments, frequency distributions are calculated for the width and the amplitude of all pulses. Frequency distributions are typically presented using a histogram. A cumulative frequency distribution may provide a useful measure of the quantitative system parameters described herein by enabling an operator to easily determine the number of events that fall above or below one or more values. For example, arranging peak values in a cumulative frequency distribution chart enables an operator to determine the number of pulses above one or more threshold values.

Although a frequency distribution provides an operator with an effective visual representation of the data, in many cases it is desirable to identify more exact characteristics of the distribution then are available from a visual analysis of the frequency distribution chart. A number of analytical measures have been developed to quantify the characteristics of the data such as central tendencies, skewness, and dispersion.

b) Central Tendencies

Averages may provide a measure of the central tendencies or central location of the data. Averages may be variously defined to include, for example, summing quantitative system response data over discrete periods (e.g., every 5 seconds, or every 5000 A/D samples), arithmetic means, RMS values, measures of the total energy, integration values over a defined interval, and/or other well known averaging techniques.

An arithmetic mean calculates the average of a set of data by summing each data item in the set and dividing by the number of data items in accordance with the following equation:

$$\mu = \frac{1}{n} \sum_{i=0}^{n-1} X_i$$

Where $X_i$ is a one or more measures of system response data.

In exemplary embodiments, some quantitative system response data may be skewed as a result of influences from noise and other factors. Accordingly, it may be desirable to calculate the average of quantitative response data which exceeds a predetermined threshold. For example, it may be desirable to only average pulses which have a width or height which exceed a predetermined threshold. It may be desirable to calculate the first or higher order moments of the mean in accordance with the following equation:

$$\mu_x^m = \frac{1}{n} \sum_{i=0}^{n-1} X_i^m$$

Where m is the $m^{th}$ order moment.

Moments of the mean may serve to better enable the average to reflect the presence of relatively large variations as, for example, acoustic spikes or pulses. Where m is a value of two or more, the presence of unusually large pulses may be strongly represented in the mean.

An alternative measure of central tendency is to calculate a root-mean-square (RMS) value. In one exemplary embodiment, a RMS value may be calculated from the voltage, current, or power of the signal received from microphone 4. For example, a RMS voltage value $V_{rms}$ may be calculated by taking the square root of the average (mean) value of the square of the voltage in accordance with the following equation:

$$V_{rms} = \sqrt{\frac{1}{T} \int_0^T v^2 dt}$$

Additionally, a RMS value may be calculated from any of the quantitative system response data in accordance with the following equation.

$$RMS_x = \sqrt{\frac{1}{n} \sum_{i=0}^{n-1} X_i^2}$$

Where $X_i$ is a one or more measures of system response data.

c) Median

The median is used to identify the central most value in a set of values. In exemplary embodiments, the medium is often calculated to be the value below and above which lie an equal number of samples. For example, if the height of acoustic pulses is being sampled, the median sample height would be the pulse height below which and above which an equal number of samples fall within any given interval. The median may be calculated over any of the intervals defined above. For example, if the median were calculated over the duration of a pulse, the A/D samples over the interval may be sorted as an array with the median value being the middle element of the sorted array.

d) Mode

The mode is the value or range of values that occur most frequently. The mode is most useful when the data is grouped into ranges to determine which range occurs most frequently. For example, if the height of acoustic pulse data is sampled using 5 threshold levels, it may be desirable to determine the number of acoustic pulses that fell within the five threshold ranges. The mode could be utilized to determine which of the 5 ranges contained the most number of pulses.

The mode may also be useful in determining whether a particular frequency distribution chart or histogram contains a multi-modal distribution. By multi-modal, it is meant that the data exhibits two (bi-modal) or more peaks in the distribution. Multi-modal distributions may be indicative of physical attributes of the porous element. For example, in analyzing the system response data, some non-defective porous elements may exhibit a substantially single modal distribution, while some defective porous elements may exhibit a substantially multi-modal distribution.

e) Dispersion

Dispersion refers to the spread or variability of a set of data. Although two groups of data may have the same average, elements within the groups may differ greatly with respect to the spread or dispersion of the individual observations.

One measure of dispersion is a simple distance measure or range. For example, the range of a set of data may be a simple measure of the difference between the value of the highest and lowest term. Other ranges may also be of interest. For example, fractiles measure the range of any arbitrary percentage of data samples, such as the range of the center most 80% of the samples. An interquartile range may be defined as the difference between the value in which three quarters of the observations lie below it and a value in which one quarter of the observations lie above it. Thus, the distance between these two numbers measures the spread of the values that span the middle 50% of the distribution. Range measures provide a simplified measure of the dispersion of the samples measured.

More comprehensive methods of measuring dispersion are also available. For example, it may be desirable to measure the average deviation of all the data items from an average. Well known measures of dispersion such as the standard deviation and the variance are preferred and have been found to be excellent measures of the amount of variations in the quantitative acoustic data.

The standard deviation is typically calculated according to the following equation:

$$\sigma_x = \sqrt{\frac{1}{n} \sum_{i=0}^{n-1} (X_i - \mu)^2}$$

Where $X_i$ is a one or more measures of system response data, and $\mu$ is a baseline value, a threshold value, an average value, or a measure of central tendency determined in accordance with the methods discussed above.

For example, it has been found that the standard deviation of the pulse amplitudes for defective porous elements may be higher than the standard deviation of the pulse amplitudes for non-defective porous elements.

A useful formula for measuring dispersion is the moment about the mean calculated in accordance with the following equation:

$$\sigma_x^m = \frac{1}{n} \sum_{i=0}^{n-1} (X_i - \mu)^m$$

Where $\sigma_x^m$ is the mth order moment about the mean, $\mu$ is a measure of central tendency, threshold value, baseline value, or other average value in accordance with one of the methods discussed above.

Where m=1, the above equation provides a measure of the average deviation of one or more of the system response data. For example, it may be desirable to determine the average value by which the peaks of acoustic pulses exceed the threshold value. Similar measures may be made for each of the quantitative system response data. With some quantitative measures such as when m is an odd number, it may be desirable to first take the absolute values of $(X_i - \mu)$.

Increasing the value of m to a value greater than 1 may provide a measure related to various system parameters. For example, where m=2, the above equation generates what is commonly referred to as the variance of the system response data being analyzed; where m=3, the above equation generates what is commonly referred to as the skewness of the system response data being analyzed; where m=4, the above equation generates a measure of what is commonly referred to as the Kurtosis. The Kurtosis may provide a measure of peakedness such as the degree of curvature of the peak of a probability curve.

As the order m of the moment about the mean increases, the above equation has a tendency to strongly reflect the presence of a relatively small number of large variations as with, for example, acoustic spikes or pulses generated by pin-hole defects. Where m is a value of two or more, the presence of large pulses may be strongly represented.

e) Distribution Probabilities

Some system response data for a particular porous element or system response data gathered from a plurality of porous elements may approximate known distributions such as, for example, a normal distribution or an exponential distribution. It may be desirable to calculate from these known distributions the probability that one or more system responses is being produced by either a defective or non-defective porous element. Well known techniques for calculating these probabilities may be utilized to determine the probability that measured system response data is from a defective porous element.

Step V: Data Correlation:

The measures of system response data defined above can be correlated with defective and non-defective filters. In this manner, various confidence indexes and pass-fail determinations can be made concerning a particular filter under test.

In preferred embodiments, one or more measures of system response data are combined to form a pass-fail determination for each porous element under test. Further, if a plurality of system response data are utilized, filters that do not fail individual quantitative measures of integrity, but have values falling within a suspect range of a plurality of quantitative measures, can be identified for close scrutiny.

Correlation analysis provides a measure of the relationships (correlation) between the various system response data. In preferred embodiments, the correlation analysis measures the degree to which two or more measures of the system response data exhibit a tendency to vary together. A correlation analysis may involve testing a number of defective and non-defective porous elements and recording system response data for each porous element. The porous elements may be assigned various levels. For example, level 0 may define a defective porous element and level 1 may define a non-defective porous element. The use of more than two levels is also possible to grade various porous elements. For example, a third level may be included to categorize marginal porous elements for close scrutiny. A defective and non-defective filter may be defined by, for example, particle challenge tests. Next, a correlation analysis may be conducted for each category of system response data to determine which of the system response data discussed above correlates with the particle challenge tests.

The correlation may be performed by an operator by, for example, determining that defective porous elements all have more than 30 pulses for every 5 seconds while all non-defective porous elements have less than 4 pulses for every 5 seconds. System response data from the porous element testing system that has been found to provide excellent correlation between defective and non-defective porous elements includes pulse counting, standard deviation of acoustic signals, average pulse amplitude, average pulse width, and ultrasonic first bubble.

More sophisticated correlation methods are available for correlating system response data to defective and non-defective porous elements provided certain assumptions are made concerning the distributions of the system response data. For example, the correlation coefficient r may be determined for two sets of system response data $(x_i, y_i)$ by dividing the co-variance of x and y by the square root of the product of their variances in accordance with the following equation.

$$r = \frac{\sum_{i=1}^{n}(x_i - \bar{x})(y_i - \bar{y})}{\sqrt{\sum_{i=1}^{n}(x_i - \bar{x})^2 \sum_{i=1}^{n}(y_i - \bar{y})^2}}$$

In other embodiments, an analysis of variance (ANCOVA/MANCOVA) between the two or more sets of system response data may be performed using known techniques. The variance between the system response data may be calculated by any well known technique, including least squares. In exemplary embodiments, the analysis of variance breaks up the total sum of squares tss (a measure of variance) into a number of component sum of squares for each system response data which may correlate to the independent variable. In exemplary embodiments, the independent variable is defined as whether the porous element is or is not defective. Other independent variables are possible including such variables as pore size distribution, maximum pore size, and other physical properties of the porous element. If an analysis of variance between two sets of system response data are performed, then the total sum of squares tss may be defined as follows:

$$tss = ssa + sse.$$

Where ssa is a measure of the variations attributable or correlated with system response data A, and sse is a measure of the variations due to random fluctuations (e.g. error, noise).

Using well known equations, it is possible to calculate the averages msa and mse. If there is a strong correlation between the two sets of system response data, then msa will be larger than mse. When msa is significantly larger than mse, the two sets of system response data strongly correlate. Other methods of correlation analysis, e.g., regression analysis, may also be used in addition to the correlation techniques defined above.

Regression analysis, and in particular, multiple regression analysis, provides a procedure for determining a relationship between a dependent variable, such as the integrity of a porous element, and one or more independent variables, such as the system response data. Multiple regression analysis is an extension of two variable correlation analysis. There are numerous commercially available computer programs which perform a step-wise or multiple regression analysis, such as SPSS (originally written at Stanford University and now available from SPSS), Statistica (available from Statsoft), Systat (available from Systat Inc.), and LabVIEW For Windows (available from National Instruments). Multiple regression analysis may derive appropriate regression equations and models (e.g., linear, curvilinear, non-linear as, for example, Levenberg-Marquardt, exponential, polyfit), using any suitable method, such as, least squares. In one embodiment, the computer program determines which of the independent variables correlates with the dependent variable using the conventional statistical measures for the two variable relationship as, for example, discussed above. Next, the program selects the independent variables which accomplish the greatest reduction in the unexplained variance remaining after the two variable analysis has been completed. The program continues to add additional variables to minimize the amount of unexplained error. Variables can be deleted or added as desired.

An important feature of the present invention includes determining those quantitative system response data which correlate with physical characteristics of the porous element. The quantitative system response data may then be utilized to increase the number of dependent variables for correlation with physical aspects of a porous element to enhance the ability to discriminate between defective and non-defective filters using non-destructive tests. It has been found that the ultrasonic first bubble, ultrasonic bubble point, pulse count data, and pulse amplitude are important quantitative system response data for enhancing the correlation. Additionally, it has been found that the use of forward flow quantitative data in conjunction with ultrasonic quantitative data allows for a greater level of discrimination between defective and non-defective porous elements without any additional testing time.

Figure 29:
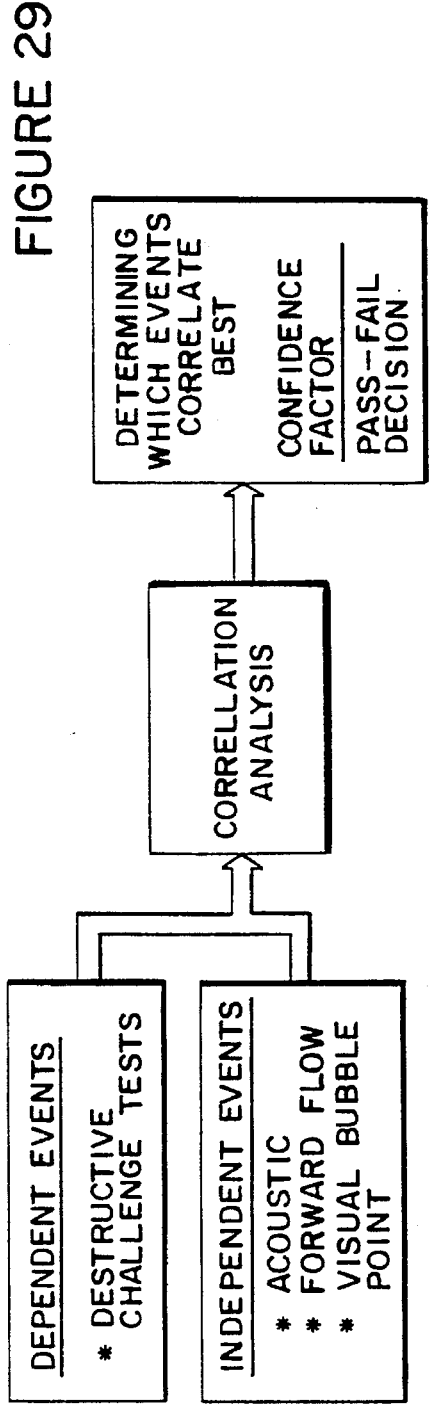
FIGS. 29 and 30 are flow charts illustrating typical correlation analysis.
Figure 30:
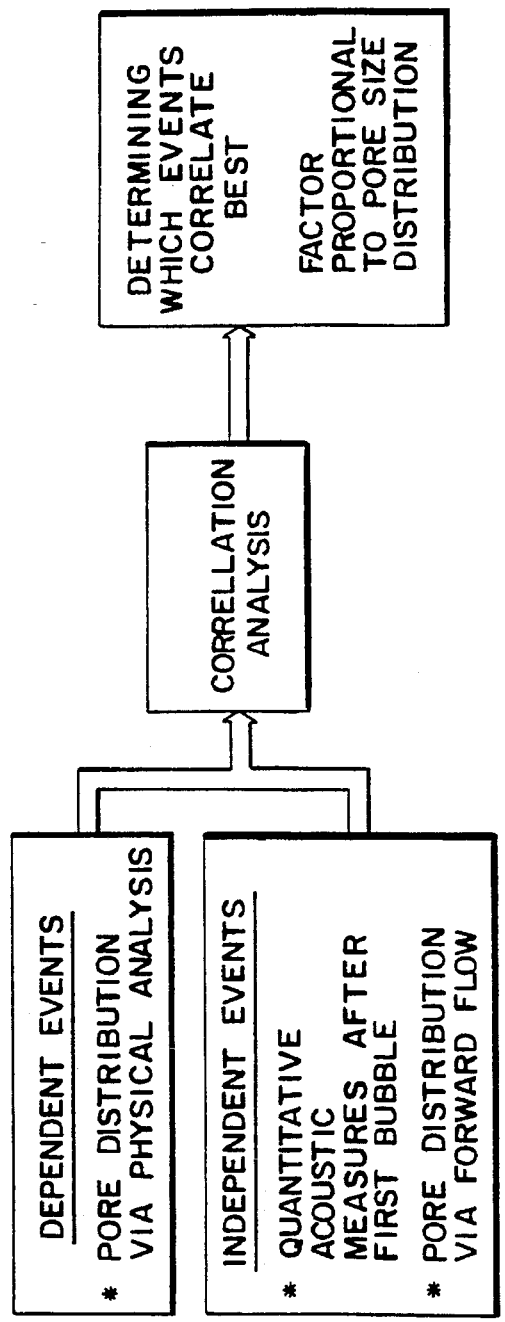

Exemplary methods according to the present invention are shown in FIGS. 29 and 30. FIG. 29 shows a flow chart depicting the correlation of destructive challenge tests with one or more of: ultrasonic, forward flow, and visual bubble point system response data. In exemplary embodiments, quantitative acoustic data is utilized either alone or in conjunction with forward flow or visual bubble system response data to determine which system response data correlates best. In this manner, confidence indexes and/or pass/fail criteria for each type of porous element may be defined. In preferred embodiments, quantitative acoustic system response data (and most preferably quantitative acoustic signal data) are correlated with quantitative measures of flow data to discriminate between defective and non-defective porous elements. FIG. 30 shows correlating pore distribution of a porous element with forward flow data and/or one or more acoustic quantitative measures in an interval after the first bubble is reached. The use of quantitative acoustic data may allow for increased discrimination in determining such measures as: the minimum pore size, the uniformity of the pore sizes, the dry flow, mean pore size, cumulative flow, and differential flow.

Step V: Data Interpretation:

One aspect of the porous element testing system 1 is to provide systems and methods for interpreting one or more of the quantitative measures of system response data or correlation analyses to draw inferences concerning the likelihood that a particular porous element will function according to predetermined parameters. For example, an index can be calculated from system response data for each porous element under test. If the index exceeds a predetermined threshold, then the porous element is considered to be defective. The predetermined threshold is set to ensure, to a very high probability, that the porous element will meet or exceed specified operating parameters. The output to the operator may be variously defined. In some embodiments, the operator may be provided with detailed porous element response data for the element under test. In other embodiments, only a simple pass-fail determination is output to the operator.

As previously discussed, the porous element testing system 1 shown may also be used as a diagnostic tool to allow certain kinds or sizes of defects to be "finger printed" by their system response data characteristics, or as a tool to monitor the manufacturing process to determine whether an entire manufacturing lot is within manufacturing specifications.

Step VII: Data Presentation

Typical outputs from the operator display terminal 50 are shown in FIG. 15 as discussed above, and in FIGS. 19-22. FIGS. 19-22 were selected to contrast the response of defective filters with non-defective filters using the systems and methods disclosed in the present application. These defective and non-defective porous elements are exemplary. Some defective porous elements exhibit either a more subtle or more vigorous response than these exemplary porous element responses. Referring to FIGS. 19-22, Part A of each Figure shows the first bubble and bubble point differential pressure as determined using acoustic data, and the forward flow bubble point. Part B of each Figure shows a graphical illustration of the acoustic energy signal from a non-defective porous element sampled at a rate of 20 KHz. The top of the graphical illustration displays the current analog acoustical signal output voltage. Part C of each Figure shows the pressure applied to the porous element under test with the current pressure displayed at the top of the graphical illustration. Part D of each Figure displays a graphical representation of the mass flow with the current mass flow displayed at the top of the graphical illustration. Part E of each Figure shows a histogram of the amplitude of pulses, the mean pulse amplitude and the standard deviation of the pulse amplitude. Part F of each Figure shows a histogram of the width of the pulses, and the mean pulse width. The current pulse width and height are shown at the top of the graphical portion in Parts E and F, respectively. Part G displays a graphical representation of the pulse count, and the current pulse count using 5 voltage threshold values. Time is shown in the horizontal axis in Parts B, C, D, and G.

Figure 19:
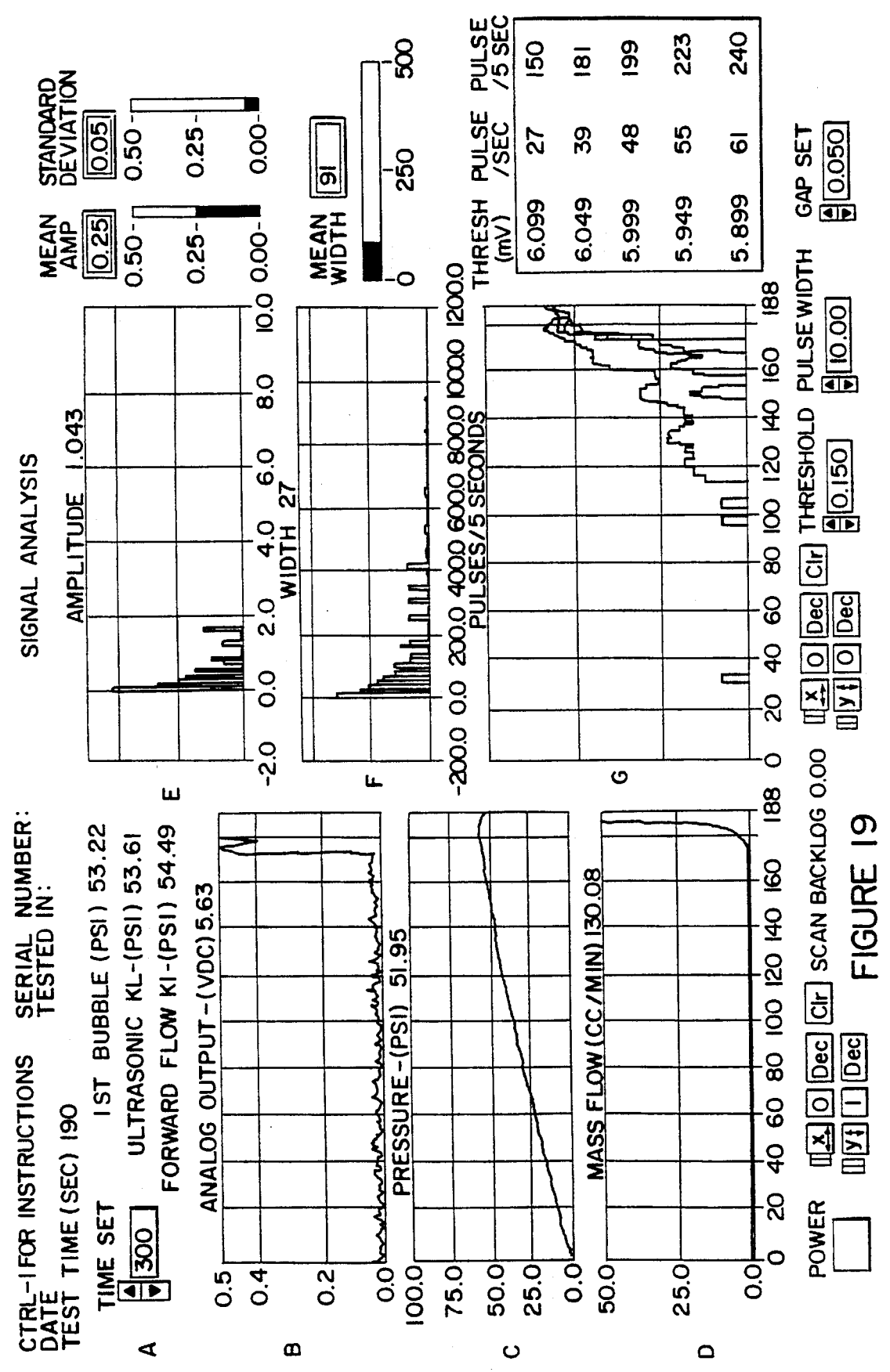

FIG. 19 is a graphical representations of typical front panel screen displayed during a dynamic pressure test of a non-defective porous element. In part A, the ultrasonic first bubble, the ultrasonic bubble point, and forward flow bubble point are closely matched. Referring to Part B, the non-defective porous element has a steep and strong response after reaching the bubble point. Part D has a low initial forward flow rate followed by a steep increase at the bubble point. Referring to part G, the pulse counts start to rise at about 115 seconds into the test, well before the bubble point.

Figure 20:
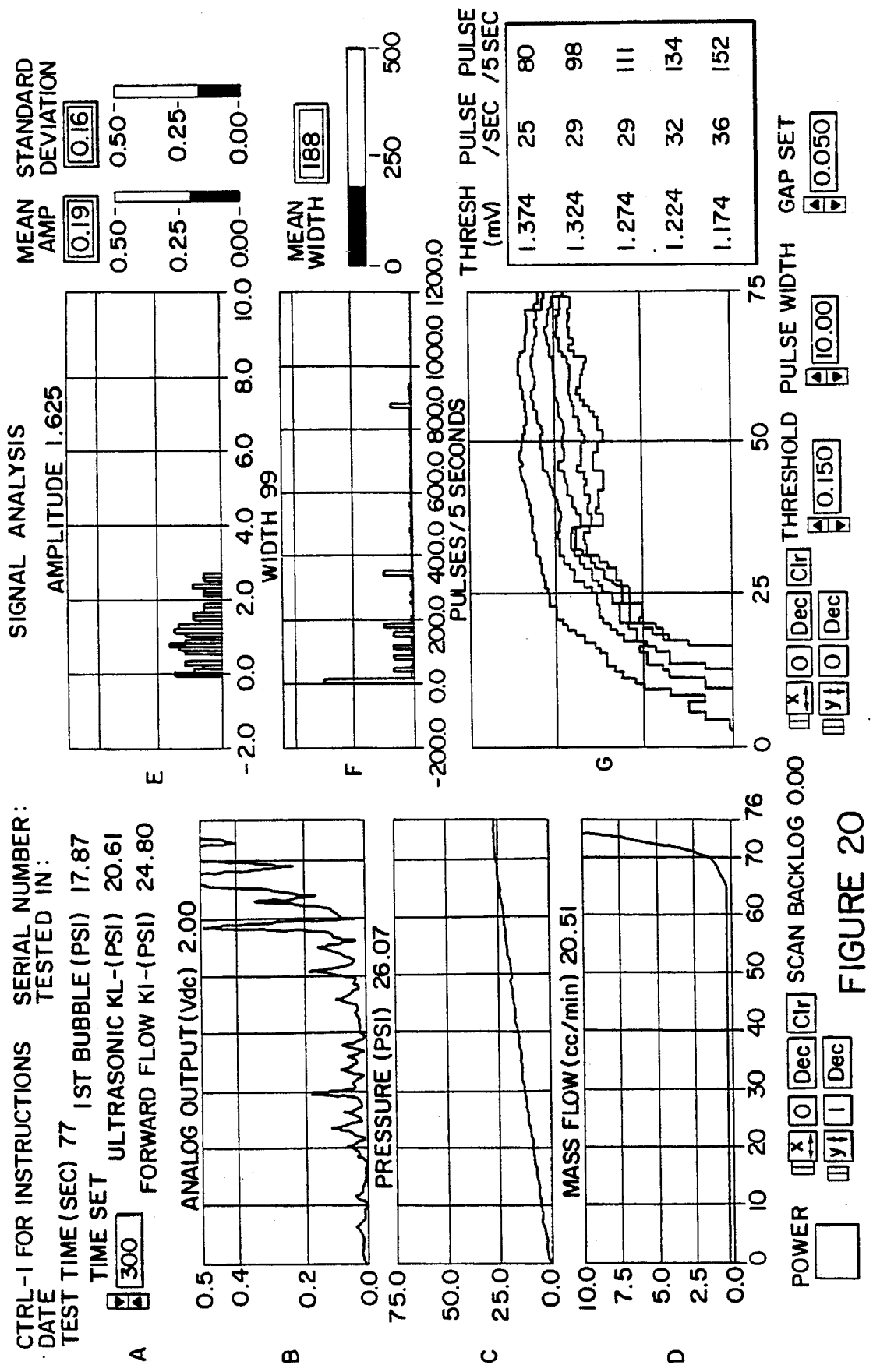
FIG. 20 is graphical representations of typical front panel screen displayed during a dynamic pressure test of a defective porous element according to the embodiment of the testing apparatus illustrated in FIG. 12.

FIG. 20 is graphical representations of typical front panel screen displayed during a dynamic pressure test of a defective porous element. There is a strong contrast between the system response data for the defective porous element in FIG. 20 and the non-defective system response characteristics shown in FIG. 19. In part A, the ultrasonic first bubble, the ultrasonic bubble point, and forward flow bubble point are widely spaced. Referring to Part B, the defective porous element has a gradual, weak, discontinuous response after reaching the bubble point. Additionally, the response after reaching the first bubble is only slightly stronger than the response attributable to noise. Part D has a relatively high forward flow rate followed by a relatively gradual increase in the forward flow rate at the bubble point. In Part G, the pulse counts for the defective filter begin to rise almost from the start of the test time (around 5 seconds after stabilization). In part F and G, the mean amplitude, pulse width, and standard deviation may become skewed upon reaching the bubble point for the dynamic pressure tests in FIGS. 19 and 20.

Figure 21:
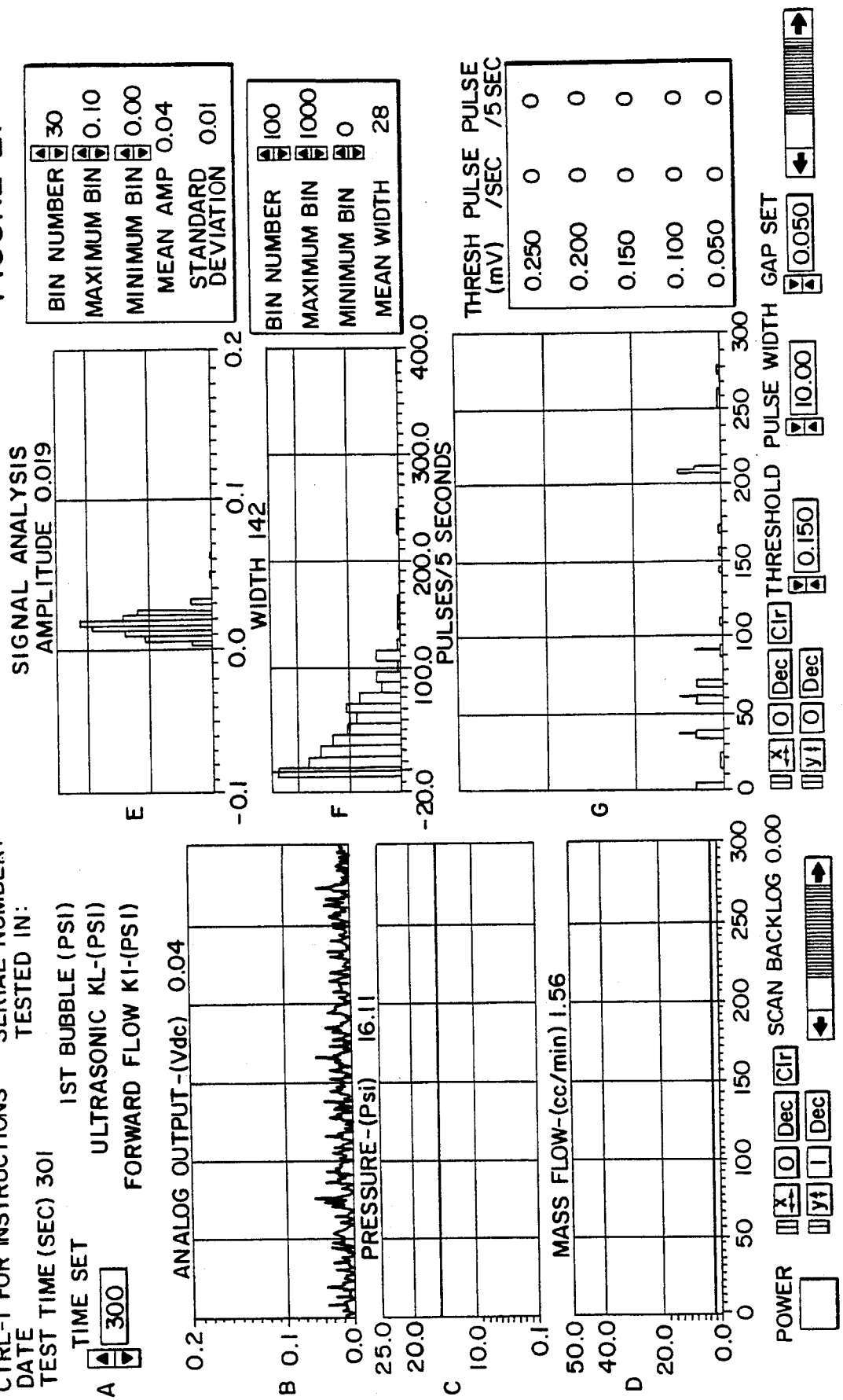
FIG. 21 is graphical representations of typical front panel screen displayed during a static pressure test of a non-defective porous element according to the embodiment of the testing apparatus illustrated in FIG. 12.

FIG. 21 is graphical representations of typical front panel screen displayed during a static pressure test of a non-defective porous element. In FIG. 21, the pulse amplitudes and standard deviation fall within a narrow range. The pulse widths also have a relatively narrow range. Pulse counts displayed in part G are very small.

Figure 22:
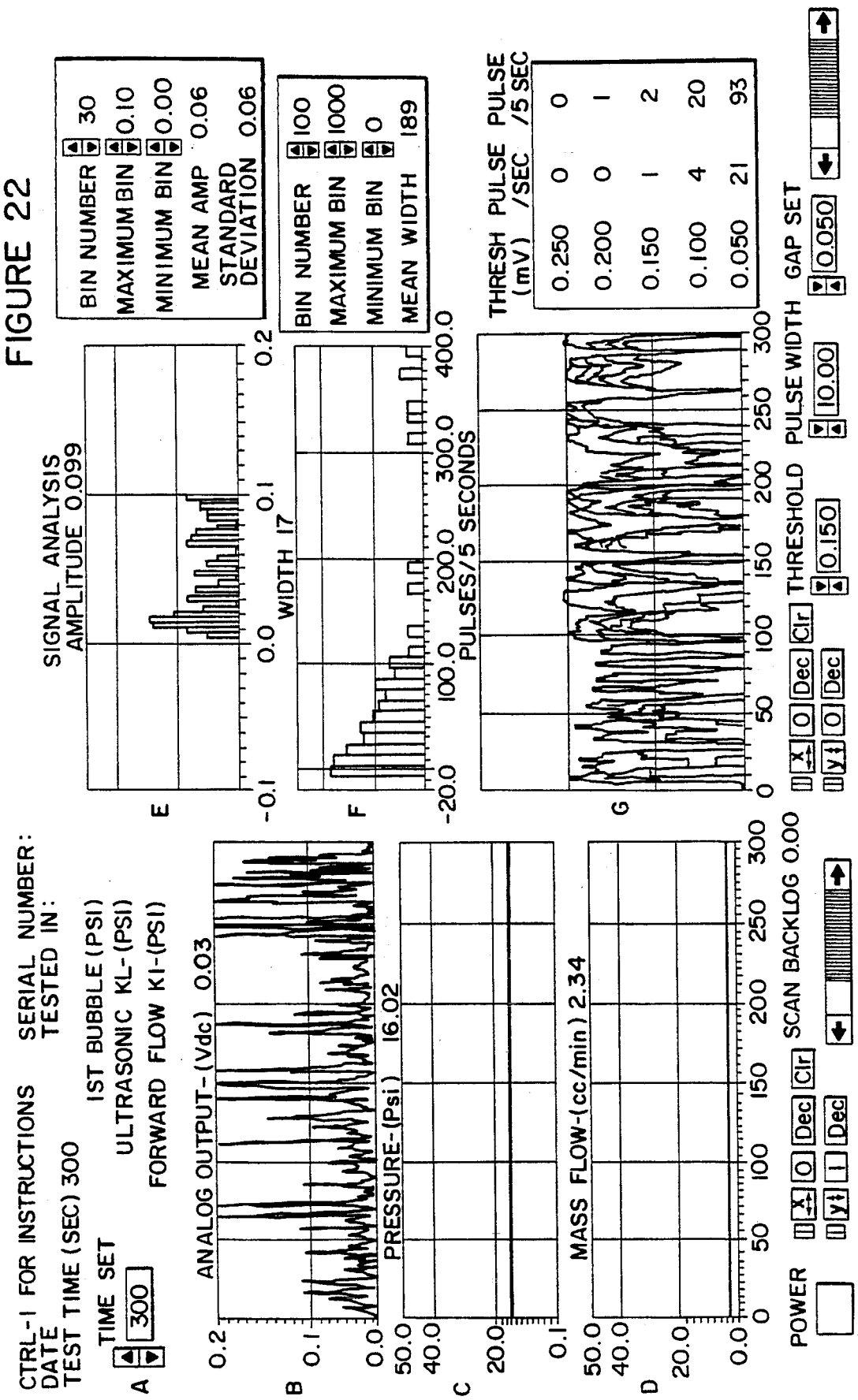
FIG. 22 is graphical representations of typical front panel screen displayed during a static pressure test of a defective porous element according to the embodiment of the testing apparatus illustrated in FIG. 12.

FIG. 22 is graphical representations of typical front panel screen displayed during a static pressure test of a defective porous element. In FIG. 22, the pulse amplitudes and standard deviation fall within a wide range. The pulse widths are also widely distributed. Pulse counts for each of the various threshold levels exhibit a strong response.

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention. For example, it may be possible to utilize the defective porous element identification methods and apparatuses to detect defects in a fluid coupled acoustic testing apparatuses.

What is claimed is:

1. A porous element testing system for testing a porous element wetted with a wetting solution, the porous element testing system comprising:

a housing having a first side and a second side, wherein the first side is divided from the second side by the wetted porous element and wherein the first side and the second side are both filled with a gas;

a differential pressure generator generating a differential pressure across the wetted porous element;

a transducer disposed in the vicinity of the porous element and receiving acoustic signals generated within the housing;

a signal processing device, coupled to the transducer, analyzing the acoustic signals received from the transducer for determining whether the porous element is defective.

2. The porous element testing system of claim 1 including a gas flow meter monitoring gas flow through the porous element.

3. The porous element testing system of claim 1 including a mechanism shielding the transducer from contact with the wetting solution.

4. The porous element testing system of claim 1 including a mechanism for reducing the differential pressure prior to opening the housing.

5. The porous element testing system of claim 1 wherein the differential pressure generator generates a first differential pressure having a first pressure in the first side larger than a second pressure in the second side and a second differential pressure having a third pressure in the first side less than a fourth pressure in the second side, the signal processing device analyzing the acoustic signals received from the transducer while the porous element is exposed to the first and second differential pressures.

6. The system of claim 1 including means for inducing a sonic signal detectable by the transducer.

7. The system of claim 1 wherein the signal processing device includes a discrimination threshold level and is configured for electronically analyzing the acoustic signals by registering variations in the acoustic signals that exceed the discrimination threshold level.

8. The system of claim 7 wherein the signal processing device is configured to vary the discrimination threshold level.

9. The system of claim 7 wherein the signal processing device is configured for counting pulses by determining the number of times the acoustic signals exceed the discrimination threshold during an interval.

10. The system of claim 7 including means coupled to the signal processing device for signalling an operator whenever the variations registered exceed a predetermined value during a particular interval.

11. The system of claim 1 wherein the signal processing device is configured for setting a plurality of discrimination thresholds having differing levels and for registering variations in the acoustic signals that exceed each of the plurality of discrimination thresholds.

12. The system of claim 1 wherein the signal processing device is configured for electronically analyzing the acoustic signals using statistical measures.

13. The system of claim 12 wherein the statistical measures include a frequency distribution.

14. The system of claim 13 including a display coupled to the signal processing device, the display being arranged to display the frequency distribution as a histogram.

15. The system of claim 1 wherein the signal processing device is configured for electronically analyzing the acoustic signals using a measure of minimum sound pressure levels.

16. The system of claim 1 wherein the signal processing device is configured for electronically analyzing the sounds using a measure of signal density.

17. The system of claim 1 wherein the signal processing device is configured for measuring variations in frequencies of the acoustic signals.

18. The system of claim 1 wherein the signal processing device is configured for measuring variability of the acoustic signals.

19. The system of claim 1 wherein the signal processing device is configured for electronically counting pulses in the acoustic signal and for determining whether the porous element is defective in accordance with the pulses counted.

20. The system of claim 19 wherein the signal processing device is configured for counting pulses in accordance with a sliding window technique.

21. The system of claim 1 wherein the differential pressure generator is arranged to generate a substantially constant differential pressure across the wetted porous element, the substantially constant differential pressure having a value less than an anticipated bubble point pressure of the wetted porous element.

22. The system of claim 21 wherein the signal processing device is configured for determining whether the porous element is defective using acoustic signals received after a stabilization period.

23. The system of claim 21 wherein the differential pressure generator is configured for applying a substantially constant differential pressure across the wetted porous element of between 30 and 95 percent of the anticipated bubble point of the wetted porous element.

24. The system of claim 23 wherein the differential pressure generator is configured for applying a substantially constant differential pressure of about 80 percent of the anticipated bubble point.

25. The system of claim 1 wherein the signal processing device is configured for quantifying a characteristic of the acoustic signals into a quantitative value, the quantitative value being indicative of whether the wetted porous element is likely to be defective.

26. The system of claim 25 including a display coupled to the signal processing device, wherein the quantitative value is displayed on the display.

27. The system of claim 25 wherein the signal processing device is configured for determining the quantitative value using a statistical measure of the variability of the acoustic signals.

28. The system of claim 27 wherein the statistical measure includes a standard deviation.

29. The system of claim 27 wherein the statistical measure includes a mean.

30. The system of claim 1 wherein the signal processing device is configured for varying sampling and analysis parameters responsive to a code input by a user indicative of a type of porous element being tested.

31. The system of claim 1 wherein the signal processing device includes a digital filtering algorithm for filtering the acoustic signals.

32. The system of claim 1 wherein the signal processing device is configured for determining a pore size distribution of the porous element using acoustic signals from the porous element generated before and after application of the wetting solution.

33. The system of claim 1 wherein the signal processing device is configured for comparing a first group of acoustic signals with a second group of acoustic signals and for determining a bubble point when the first and second group of acoustic signals differ by a predetermined amount.

34. The system of claim 1 wherein the signal processing device is configured for determining a confidence index indicative of the integrity of the porous element.

35. The system of claim 1 wherein the signal processing device is configured for determining background noise and for calibrating the transducer responsive to the background noise.

36. The system of claim 35 including an alarm coupled to the signal processing device for signalling the operator when the background noise exceeds a predetermined level.

37. The system of claim 1 including an outlet tube disposed down stream of the housing, wherein the transducer is disposed in the outlet tube.

38. A method for determining whether a porous element is defective comprising:

wetting a porous element with a wetting solution;

generating a differential pressure between a gas on a first side of the wetted porous element and a gas on a second side of the wetted porous element;

monitoring sound levels emanating from the vicinity of the porous element; and determining, as a result of the sound levels, whether the porous element is defective.

39. The method of claim 38 including measuring gas flow through the wetted porous element.

40. The method of claim 39 wherein measuring gas flow includes quantifying a rate of gas flow through the wetted porous element and wherein determining whether the porous element is defective includes quantifying the sound levels into acoustic data and determining physical characteristics of the porous element using the acoustic data and the gas flow rate.

41. The method of claim 40 wherein determining whether the porous element is defective further includes formulating a confidence index from both the gas flow rate and from the acoustic data indicative of whether the porous element is defective.

42. The method of claim 40 wherein determining whether the porous element is defective further includes electronically analyzing the acoustic data utilizing statistical measures.

43. The method of claim 38 wherein determining whether the porous element is defective includes electronically analyzing the sound levels by setting a discrimination threshold and registering variations in the sound levels that exceed the discrimination threshold.

44. The method of claim 43 wherein electronically analyzing the sound levels includes varying the discrimination threshold.

45. The method of claim 43 wherein electronically analyzing the sound levels includes counting variations in the sound levels that exceed the discrimination threshold as pulses.

46. The method of claim 43 including electronically analyzing the sound levels utilizing statistical measures.

47. The method of claim 46 including electronically analyzing the sound levels utilizing a measure of signal density.

48. The method of claim 46 including electronically analyzing the sound levels by measuring variability of the sounds.

49. The method of claim 38 wherein generating a differential pressure includes generating a substantially constant differential pressure across the wetted porous element having a value less than an anticipated bubble point pressure of the wetted porous element and wherein monitoring sound levels includes monitoring sound levels while the differential pressure is substantially constant.

50. The method of claim 49 including generating the substantially constant differential pressure of about 80 percent of the anticipated bubble point.

51. The method of claim 49 wherein determining whether the porous element is defective includes quantifying a characteristic of the sound levels into at least one quantitative value and comparing the at least one quantitative value with at least one predetermined value to determine whether the porous element has a particular physical characteristic.

52. The method of claim 51 further including displaying the quantitative value on a display.

53. The method of claim 51 wherein determining whether the porous element is defective includes using a measure of standard deviation of a characteristic of the sound levels.

54. The method of claim 51 wherein determining whether the porous element is defective includes using a measure of variability of a characteristic of the sound levels.

55. The method of claim 51 wherein determining whether the porous element is defective includes using an averaging technique to average a characteristic of the sound levels.

56. The method of claim 10 wherein a differential pressure and monitoring sound levels include measuring a first set of sound levels at a first differential pressure and measuring a second set of sound levels at a second differential pressure and wherein the method further comprises electronically comparing the first set of sound levels with the second set of sound levels and electronically determining a bubble point when the first and second sets of sound levels differ by a predetermined amount.

57. The method of 56 including quantifying the first set of sound levels into a first quantitative value and quantifying the second set of sound levels into a second quantitative value.

58. The method of claim 57 wherein quantifying the first quantitative value includes using an averaging technique to average a characteristic of the first set of sound levels, and quantifying the second quantitative value includes using an averaging technique to average a characteristic of the second set of sound levels.

59. The method of claim 10 including automatically determining whether the wetted porous element is defective by quantifying sounds generated by the porous element into one or more quantitative values and comparing the one or more quantitative values with one or more predetermined values.

60. A system for testing a wetted porous element, the testing system comprising:

a housing having first and second sides, wherein the first side is dividable from the second side by the wetted porous element;

differential pressure generator creating a differential pressure between the first and second sides of the housing;

a sound transducer receiving acoustic signals generated within the housing; and a gas flow meter arranged to monitor gas flow between the first and second sides of the housing.

61. The system of claim 60 including means for inducing a sonic signal detectable by the transducer.

62. The system of claim 60 including a signal processor coupled to the sound transducer, wherein the signal processor includes a discrimination threshold level and is configured for electronically analyzing the acoustic signals by registering variations in the acoustic signals that exceed the discrimination threshold level.

63. The system of claim 62 wherein the signal processor is configured to vary the discrimination threshold level.

64. The system of claim 62 wherein the signal processor is configured for counting variations in the acoustic signals that exceed the discrimination threshold as pulses.

65. The system of claim 64 wherein the signal processor is configured for counting pulses using a sliding window technique.

66. The system of claim 60 including a signal processor coupled to the sound transducer and configured for electronically analyzing the acoustic signals using statistical measures.

67. The system of claim 66 wherein the statistical measures include a measure of signal density.

68. The system of claim 66 wherein the statistical measures include a measure of variability of the acoustic signals.

69. The system of claim 60 including a signal processor coupled to the gas flow meter and the sound transducer for inputting and quantifying data related to the gas flow and to the acoustic signals.

70. The system of claim 69 wherein the signal processor is coupled to the differential pressure generator for controlling and monitoring the differential pressure to determine a bubble point of the porous element.

71. The system of claim 60 wherein the differential pressure generator is arranged to generate a substantially constant differential pressure across the wetted porous element, the substantially constant differential pressure having a value less than an anticipated bubble point pressure of the wetted porous element.

72. The system of claim 71 wherein the substantially constant differential pressure is between about 30 and 95 percent of an anticipated bubble point of the wetted porous element.

73. The system of claim 72 wherein the substantially constant differential pressure is about 80 percent of the anticipated bubble point.

74. The system of claim 60 including a signal processor coupled to the sound transducer for quantifying a characteristic of the acoustic signals into a quantitative value, the quantitative value being indicative of whether the wetted porous element is likely to be defective.

75. The system of claim 60 including a signal processor coupled to the sound transducer for adjusting test parameters responsive to a code indicative of a type of porous element under test.

76. The system of claim 60 including a signal processor coupled to the sound transducer for conditioning the acoustic signals according to a digital filtering algorithm.

77. The system of claim 60 including an outlet tube disposed downstream of the housing, wherein the sound transducer is disposed in the outlet tube.

78. A method for determining whether a porous element is defective, comprising:

wetting a porous element with a wetting solution;

creating a differential pressure across the wetted porous element;

monitoring acoustic signals generated in the vicinity of the wetted porous element; and measuring gas flow through the wetted porous element.

79. The method of claim 78 further comprising:

quantifying the acoustic signals into acoustic data;

quantifying a rate of gas flow through the wetted porous element;

determining physical characteristics of the porous element using the acoustic data and the gas flow rate.

80. The method of claim 79 further comprising formulating a confidence index from both the gas flow rate and the acoustic data indicative of whether the porous element is defective.

81. The method of claim 79 including utilizing a signal processor to analyze the acoustic data and to control the differential pressure.

82. The method of claim 79 wherein quantifying the acoustic signals includes electronically analyzing the acoustic signals by setting a discrimination threshold and registering variations in the acoustic signals that exceed the discrimination threshold.

83. The method of claim 78 further comprising electronically analyzing the acoustic signals to determine a characteristic of the porous element utilizing statistical measures.

84. The method of claim 78 further comprising electronically analyzing the acoustic signals to determine a characteristic of the porous element utilizing a measure of signal density of the acoustic signals.

85. The method of claim 78 further comprising electronically analyzing the acoustic signals to determine a characteristic of the porous element using a measure of variability of the acoustic signals.

86. The method of claim 78 wherein creating a differential pressure includes generating a substantially constant differential pressure across the wetted porous element, the substantially constant differential pressure having a value less than an anticipated bubble point pressure of the wetted porous element and wherein analyzing acoustic signals includes analyzing the acoustic signals generated while the differential pressure is substantially constant.

87. The method of claim 86 including generating the substantially constant differential pressure at about 80 percent of the anticipated bubble point.

88. A porous element testing system for testing a wetted porous element, the porous element testing system comprising:

a differential pressure generator arranged to generate a differential pressure across the wetted porous element;

a transducer disposed in the vicinity of the wetted porous element to receive acoustic signals;

a signal processing device coupled to the transducer to analyze the acoustic signals received from the transducer wherein the differential pressure generator generates a differential pressure by applying a gas having a first pressure to a first surface of the wetted porous element and a gas having a second pressure different than the first to a second surface of the wetted porous element.

89. The porous element testing system as claimed in claim 88 including a gas flow meter arranged to monitor gas flow through the wetted porous element.

90. The system of claim 88 wherein the differential pressure generator is controlled by the signal processing device to generate a substantially constant differential pressure across the wetted porous element, the substantially constant differential pressure having a value less than an anticipated bubble point pressure of the wetted porous element.

91. The system of claim 90 wherein the substantially constant differential pressure is about 80 percent of the anticipated bubble point.

92. The system of claim 90 wherein the signal processing device is configured for determining when an initial stabilization period has ended and for thereafter quantifying a characteristic of the acoustic signals into a quantitative value, the quantitative value being indicative of whether the wetted porous element is likely to be defective.

93. The system of claim 88 including an outlet tube disposed downstream from the porous element, wherein the sound transducer is disposed in the outlet tube.

94. A porous element testing system for testing a wetted porous element, the porous element testing system comprising:

a differential pressure generator arranged to generate a differential pressure across the wetted porous element;

a transducer disposed in the vicinity of the wetted porous element to receive acoustic signals;

a signal processing device coupled to the transducer to analyze the acoustic signals received from the transducer; and means for inducing a sonic signal detectable by the transducer.

95. The system of claim 94 including fault detection circuitry adapted for detecting the sonic signal.

96. The system of claim 94 wherein the signal processing device is configured for performing a calibration responsive to the sonic signal.

97. A method for determining whether a porous element is defective comprising:
   wetting porous element with a wetting solution;
   exposing first and second sides of the porous element to a differential pressure;
   monitoring sounds adjacent to the porous element; and
   electronically analyzing the sounds; and
   measuring gas flow through the wetted porous element.

98. The method of claim 97 wherein the sounds are monitored in an outlet tube downstream of the porous element.

99. The method of claim 97 including monitoring sounds while exposing the first and second sides of the porous element to a substantially constant differential pressure having a value less than an anticipated bubble point pressure of the wetted porous element.

100. The method of claim 99 including exposing the first and second sides of the porous element to a substantially constant differential pressure at about 80 percent of the anticipated bubble point.

101. The method of claim 99 wherein electronically analyzing the sounds includes quantifying a characteristic of the sounds into a quantitative value, the quantitative value being indicative of whether the wetted porous element is likely to be defective.

102. A method for determining whether a porous element is defective comprising:
   wetting a porous element with a wetting solution;
   exposing first and second sides of the porous element to a differential pressure;
   monitoring sound adjacent to the porous element using a transducer;
   determining, as a result of the sound, whether the porous element is defective; and
   inducing a sonic signal detectable by the transducer.

103. The method of claim 102 including performing a calibration responsive to the induced sonic signal.

104. The method of claim 102 wherein the sound is monitored in an outlet tube downstream of the porous element.

105. The method of claim 102 including monitoring the sound while exposing the first and second sides of the porous element to a substantially constant differential pressure having a value less than a predetermined anticipated bubble point pressure of the wetted porous element.

106. A method for determining whether a porous element is defective comprising:
   wetting a porous element with a wetting solution;
   exposing first and second sides of the porous element to a differential pressure;
   monitoring sounds adjacent to the porous element; and
   electronically analyzing the sounds by setting a discrimination threshold and registering variations in the sound levels that exceed the discrimination threshold.

107. The method of claim 106 including counting variations in the sounds that exceed the discrimination threshold as pulses.

108. The method of claim 107 including counting the pulses that occur over a predetermined time period.

109. The method of claim 108 wherein the predetermined time period is determined in accordance with a sliding window technique.

110. The method of claim 107 wherein electronically analyzing the sounds includes measuring the time between pulses.

111. The method of claim 106 wherein electronically analyzing the sounds includes setting a plurality of discrimination thresholds having differing levels and registering variations in the sound levels that exceed the each of the plurality of discrimination thresholds.

112. The method of claim 106 wherein electronically analyzing the sounds includes varying the discrimination threshold level.

113. The method of claim 112 including counting variations in the sounds that exceed the discrimination threshold as pulse.

114. The method of claim 106 wherein electronically analyzing the sounds includes measuring widths of the pulses.

115. The method of claim 106 wherein electronically analyzing the sounds includes measuring amplitudes of pulses of sounds that exceed the discrimination threshold for a predetermined time period.

116. The method of claim 106 wherein electronically analyzing the sounds includes measuring a standard deviation of a characteristic of the sounds.

117. The method of claim 116 wherein electronically analyzing the sounds includes measuring variability of a characteristic of the sounds.

118. The method of claim 117 including using an averaging technique to average a characteristic of the sounds.

119. The method of claim 106 wherein exposing the porous element to a differential pressure and monitoring sounds include measuring a first set of sounds at a first differential pressure and measuring a second set of sounds at a second differential pressure different from the first differential pressure and wherein the method further comprises electronically comparing the first set of sounds with the second set of sounds and determining a bubble point when the first and second set of sounds differ by a predetermined amount.

120. The method of claim 106 further comprising automatically determining whether the wetted porous element is defective in accordance with the analyzed sounds.

121. A method for determining whether a porous element is defective comprising:
   wetting a porous element with a wetting solution;
   exposing first and second sides of the porous element to a differential pressure;
   monitoring sounds adjacent to the porous element; and
   electronically analyzing the sounds utilizing statistical measures.

122. The method of claim 121 wherein utilizing statistical measures includes utilizing a measure of standard deviation of a characteristic of the sounds.

123. The method of claim 121 wherein utilizing statistical measures includes utilizing a measure of variance of a characteristic of the sounds.

124. The method of claim 121 wherein utilizing statistical measures includes utilizing an averaging technique to average a characteristic of the sounds.

125. The method of claim 121 further comprising inducing a sonic signal detectable by the transducer.

126. The method of claim 121 wherein electronically analyzing the sounds includes setting a discrimination threshold and registering variations in the sound levels that exceed the discrimination threshold.

127. The method of claim 126 wherein electronically analyzing the sounds further includes counting variations in the sounds that exceed the discrimination threshold as pulses.

128. The method of claim 126 wherein electronically analyzing the sounds further includes counting variations in the sounds that exceed the discrimination threshold for a predetermined period of time as pulse.

129. The method of claim 121 wherein exposing the porous element to a differential pressure and monitoring sounds include measuring sounds at a substantially constant differential pressure having a value less than an anticipated bubble point pressure of the wetted porous element.

130. The method of claim 129 including exposing first and second sides of the porous element to a substantially constant differential pressure of between 30 and 95 percent of the anticipated bubble point pressure of the wetted porous element.

131. The method of claim 130 including exposing first and second sides of the porous element to a substantially constant differential pressure of about 80% of the anticipated bubble point pressure of the wetted porous element.

132. The method of claim 121 wherein electronically analyzing the sounds includes quantifying a characteristic of sounds generated by the porous element into at least one quantitative value and comparing the at least one quantitative value with a at least one predetermined value to determine whether the porous element has a particular physical characteristic.

133. The method of claim 132 wherein the sounds are monitored in an outlet tube disposed downstream of the porous element.

134. The method of claim 132 wherein electronically analyzing the sounds includes ascertaining one or more values indicative of a confidence index related to the integrity of the porous element.

135. The method of claim 121 wherein the statistical measures include a measure indicative of pulse widths.

136. The method of claim 121 wherein the statistical measures include a measure of indicative pulse amplitudes.

137. The method of claim 121 including displaying a frequency distribution of a characteristic of the sounds generated by the porous element on a display as a histogram.

138. The method of claim 121 including adjusting sound acquisition parameters responsive to a code input by a user indicative of a type of porous element under test.

139. The method of claim 121 wherein electronically analyzing the sounds includes electronically conditioning a signal produced responsive to the sounds using a digital filtering algorithm.

140. The method of claim 121 including comparing a first group of sounds generated by the porous element at a first differential pressure with a second group of sounds generated by the porous element at a second differential pressure, greater than the first, and determining a bubble point when statistical measures associated with the first and second groups of sounds differ by a predetermined amount.

141. The method of claim 121 further comprising inducing a sonic signal detectable by the transducer.

142. A method for determining whether a porous element is defective comprising:

wetting a porous element with a wetting solution;

exposing first and second sides of the porous element to a differential pressure;

monitoring sounds adjacent to the porous element; and electronically analyzing the sounds using a measure of minimum sound pressure levels.

143. The method of claim 142 including electronically analyzing the sounds by setting a discrimination threshold level and registering variations in the sound levels that exceed the discrimination threshold.

144. The method of claim 143 wherein electronically analyzing the sounds includes counting variations in the sounds that exceed the discrimination threshold for a predetermined period of time as pulses.

145. The method of claim 142 wherein exposing the porous element to a differential pressure and monitoring sounds include measuring sounds at a substantially constant differential pressure having a value less than an anticipated bubble point pressure of the wetted porous element.

146. The method of claim 142 including comparing sounds generated by the porous element at a first differential pressure with sounds generated by the porous element at a second differential pressure, greater than the first, and determining a bubble point when the first and second group of sounds differ by a predetermined amount.

147. A method for determining whether a porous element is defective comprising:

wetting a porous element with a wetting solution;

exposing first and second sides of the porous element to a differential pressure;

monitoring sounds adjacent to the porous element; and electronically analyzing the sounds by measuring a signal density.

148. The method of claim 147 including electronically analyzing sounds by setting a discrimination threshold level and registering variations in the signal density that exceed the discrimination threshold level.

149. The method of claim 148 including registering variations in the sounds that exceed the discrimination threshold level for a predetermined period of time.

150. The method of claim 148 including measuring sounds at a substantially constant differential pressure having a value less than an anticipated bubble point pressure of the wetted porous element.

151. The method of claim 147 including comparing sounds generated by the porous element at a first differential pressure with sounds generated by the porous element at a second differential pressure, greater than the first, and determining a bubble point when the signal density of sounds at the first and second differential pressures differ by a predetermined amount.

152. A method for determining whether a porous element is defective comprising:

wetting a porous element with a wetting solution;

exposing first and second sides of the porous element to a differential pressure;

monitoring sounds adjacent to the porous element; and electronically analyzing the sounds by measuring variations in frequencies of the sounds.

153. The method of claim 152 wherein exposing the porous element to a differential pressure and monitoring sounds include measuring sounds at a substantially constant differential pressure having a value less than an anticipated bubble point pressure of the wetted porous element.

154. The method of claim 152 including comparing sounds generated by the porous element at a first differential pressure with sounds generated by the porous element at a second differential pressure, greater than the first, and determining a bubble point when the frequency of sounds at the first and second differential pressures differ by a predetermined amount.

155. A method for determining whether a porous element is defective comprising:

wetting a porous element with a wetting solution;

exposing first and second sides of the porous element to a differential pressure;

monitoring sounds adjacent to the porous element; and electronically analyzing the sounds by measuring variability of the sounds.

156. The method of claim 155 including electronically analyzing sounds generated by the porous element to determine a characteristic of the porous element by setting a discrimination threshold level and registering variations in the sounds that exceed the discrimination threshold level.

157. The method of claim 156 including registering variations in the sounds that exceed the discrimination threshold level for a predetermined period of time.

158. The method of claim 157 including measuring sounds at a substantially constant differential pressure having a value less than an anticipated bubble point pressure of the wetted porous element.

159. The method of claim 158 including generating the substantially constant differential pressure across the wetted porous element at between about 30 and 95 percent of the anticipated bubble point of the wetted porous element.

160. The method of claim 159 including determining background noise and calibrating the acoustic sensor responsive to the background noise.

161. The method of claim 159 including generating the substantially constant differential pressure at about 80 percent of the anticipated bubble point.

162. The method of claim 155 including using the variability of the sounds generated by the porous element to determine a confidence index indicative of whether the porous element is defective.

163. The method of claim 155 including comparing sounds generated by the porous element at a first differential pressure with sounds generated by the porous element at a second differential pressure, greater than the first, and automatically determining a bubble point when the signal variability of sounds at the first and second differential pressures differ by a predetermined amount.

164. The method of claim 163 including determining background noise and calibrating the electronic analysis of the sounds responsive to the background noise.

165. The method of claim 163 including conditioning signals responsive to the sounds according to a digital filtering algorithm.

166. Apparatus for testing a wetted porous element comprising:

a transducer positionable in the vicinity of the wetted porous element to receive acoustic signals and a signal processing device coupled to the transducer to count pulses in the acoustic signal and determine whether the porous element is defective in accordance with the pulses counted.

167. A method for testing a wetted porous element comprising:

counting acoustic pulses emanating from the wetted porous element and determining whether the porous element is defective in accordance with the acoustic pulses counted.

168. The method of claim 167 including electronically analyzing sounds generated by the porous element to determine a characteristic of the porous element by setting a discrimination threshold level and registering pulse counts which exceed the discrimination threshold level for any interval.

169. The method of claim 168 including registering pulses using a sliding window technique.

170. The method of claim 168 including counting pulses at a substantially constant differential pressure having a value less than an anticipated bubble point pressure of the wetted porous element.

171. The method of claim 170 including determining background noise and calibrating the acoustic sensor responsive to the background noise.

172. The method of claim 170 including generating the substantially constant differential pressure at about 80 percent of the anticipated bubble point.

173. The method of claim 170 including using the pulse counts to determine a confidence index indicative of whether the porous element is defective.

174. The method of claim 167 including comparing acoustic pulses generated by the porous element at a first differential pressure with acoustic pulses generated by the porous element at a second differential pressure, greater than the first, and determining a bubble point when the pulse counts at the first and second differential pressures differ by a predetermined amount.

175. The method of claim 174 including determining background noise and calibrating an electronic analysis of the sounds responsive to the background noise.

176. A porous element testing system for testing a wetted porous element comprising:

a differential pressure generator arranged to generate a substantially constant differential pressure across a wetted porous element, the substantially constant differential pressure having a value less than a predetermined anticipated bubble point pressure of the wetted porous element;

a transducer disposed in the vicinity of the wetted porous element to receive acoustic signals; and a signal processing device coupled to the transducer and receiving signals indicative of the sounds.

177. The testing system of claim 176 wherein the signal processing device analyzes the acoustic signals.

178. The testing system of claim 177 wherein the signal processing device quantifies a characteristic of the acoustic signals into a quantitative value indicative of a physical characteristic of the wetted porous element, and thereby facilitates a determination of whether the wetted porous element is defective.

179. The testing system of claim 178 wherein the signal processing device automatically determines whether the wetted porous element is defective.

180. The system of claim 176 wherein the signal processing device includes means for automatically determining whether the porous element is likely to be defective.

181. The system of claim 176 wherein the signal processing device includes means for quantifying the acoustic signal data in time sequential order.

182. The system of claim 176 wherein the signal processing device is configured to include means for quantifying identifiable acoustic signal features of the acoustic signal data.

183. The system of claim 176 wherein the signal processing device includes means for quantifying acoustic energy variations.

184. The system of claim 176 wherein the signal processing device includes means for quantifying a rate of change of acoustic energy generated by the porous element.

185. The system of claim 176 wherein the signal processing device includes means for quantifying total/average acoustic energy generated over an interval.

186. The system of claim 176 wherein the signal processing device includes means for quantifying frequency/duration of identifiable acoustic signal features.

187. A porous element testing system for testing a wetted porous element comprising:
- a differential pressure generator arranged to generate a differential pressure across a wetted porous element;
- a transducer disposed in the vicinity of the wetted porous element to receive acoustic signals;
- a signal processing device, coupled to the transducer, for quantifying a characteristic of the acoustic signals into a quantitative value, the quantitative value being indicative of whether the wetted porous element is likely to be defective.

188. The system of claim 187 wherein the signal processing device includes means for automatically determining an ultrasonic first bubble pressure.

189. The system of claim 187 wherein the signal processing device includes means for automatically determining an ultrasonic $K_L$.

190. The system of claim 187 wherein the signal processing device includes means for quantifying the acoustic signal data in time sequential order.

191. The system of claim 187 wherein the signal processing device includes means for quantifying identifiable acoustic signal features of the acoustic signal data.

192. The system of claim 187 wherein the signal processing device includes means for quantifying acoustic energy variations.

193. The system of claim 187 wherein the signal processing device includes means for quantifying a rate of change of acoustic energy generated by the porous element.

194. The system of claim 187 wherein the signal processing device includes means for quantifying total/average acoustic energy generated over an interval.

195. The system of claim 187 wherein the signal processing device includes means for quantifying frequency/duration of identifiable acoustic signal features.

196. A system for testing a porous element comprising:
- a housing having a first side and a second side, wherein the first side is divided from the second side by the porous element;
- a differential pressure generator for generating a differential pressure across the porous element;
- a transducer disposed in the vicinity of the porous element for receiving acoustic signals generated within the housing;
- a signal processing device, coupled to the transducer, receiving non-acoustic system response data and acoustic data, quantifying the acoustic data, and determining physical characteristics of the porous element responsive to the acoustic data and to the non-acoustic system response data.

197. The system of claim 196 wherein the non-acoustic system response data is obtained using a forward flow test apparatus.

198. A method for testing a porous element comprising:
- quantifying acoustic data related to the porous element;
- quantifying non-acoustic system response data related to the porous element;
- determining physical characteristics of the porous element using the acoustic data and the non-acoustic data.

199. The method of claim 198 wherein quantifying the non-acoustic system response data includes using a forward flow test.

200. A method for determining whether a porous element is defective comprising:
- wetting a porous element with a wetting solution;
- exposing first and second sides of the porous element to a differential pressure;
- monitoring sounds adjacent to the porous element;
- quantifying a characteristic of the sounds into a at least one quantitative value;
- comparing the at least one quantitative value with a at least one predetermined value to determine whether the porous element has a particular physical characteristic.

* * * * *